(12) United States Patent
Pruzanski et al.

(10) Patent No.: US 12,337,003 B2
(45) Date of Patent: *Jun. 24, 2025

(54) PHARMACEUTICAL COMPOSITIONS FOR COMBINATION THERAPY

(71) Applicant: Intercept Pharmaceuticals, Inc., Morristown, NJ (US)

(72) Inventors: Mark Pruzanski, New York, NY (US); Luciano Adorini, Milan (IT)

(73) Assignee: Intercept Pharmaceuticals, Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/700,317

(22) Filed: Mar. 21, 2022

(65) Prior Publication Data

US 2022/0280533 A1 Sep. 8, 2022

Related U.S. Application Data

(63) Continuation of application No. 15/548,537, filed as application No. PCT/US2016/016694 on Feb. 5, 2016, now Pat. No. 11,311,557.

(60) Provisional application No. 62/113,134, filed on Feb. 6, 2015.

(51) Int. Cl.
| | | |
|---|---|---|
| *A61K 31/575* | (2006.01) | |
| *A61K 31/192* | (2006.01) | |
| *A61K 31/216* | (2006.01) | |
| *A61K 31/366* | (2006.01) | |
| *A61K 31/40* | (2006.01) | |
| *A61K 31/451* | (2006.01) | |
| *A61K 31/56* | (2006.01) | |
| *A61K 45/06* | (2006.01) | |

(52) U.S. Cl.
CPC .......... *A61K 31/575* (2013.01); *A61K 31/192* (2013.01); *A61K 31/216* (2013.01); *A61K 31/366* (2013.01); *A61K 31/40* (2013.01); *A61K 31/451* (2013.01); *A61K 31/56* (2013.01); *A61K 45/06* (2013.01)

(58) Field of Classification Search
CPC .................................................. A61K 31/575
See application file for complete search history.

(56) References Cited

U.S. PATENT DOCUMENTS

| | | |
|---|---|---|
| 3,262,580 A | 7/1966 | Markowitz |
| 3,369,025 A | 2/1968 | Bolhofer |
| 3,674,836 A | 7/1972 | Creger |
| 3,716,583 A | 2/1973 | Nakamura et al. |
| 3,723,446 A | 3/1973 | Scherm et al. |
| 3,781,328 A | 12/1973 | Witte et al. |
| 3,869,477 A | 3/1975 | Shindo et al. |
| 3,948,973 A | 4/1976 | Phillips |
| 3,971,798 A | 7/1976 | Humbert et al. |
| 3,984,413 A | 10/1976 | Metz et al. |
| 4,058,552 A | 11/1977 | Mieville |
| 5,023,252 A | 6/1991 | Hseih |
| 5,532,371 A | 7/1996 | Komoto et al. |
| 6,187,814 B1 | 2/2001 | Elias et al. |
| 6,384,062 B1 | 5/2002 | Ikeda et al. |
| 7,119,198 B2 | 10/2006 | Lohray et al. |
| 7,138,390 B2 | 11/2006 | Pellicciari et al. |
| 7,259,186 B2 | 8/2007 | Cink et al. |
| 7,932,244 B2 | 4/2011 | Pellicciari et al. |
| 8,772,342 B2 | 7/2014 | Darteil et al. |
| 9,238,673 B2 | 1/2016 | Steiner et al. |
| 11,311,557 B2 | 4/2022 | Pruzanski et al. |
| 2002/0025981 A1 | 2/2002 | Buch et al. |
| 2002/0120137 A1 | 8/2002 | Houze et al. |
| 2002/0132223 A1 | 9/2002 | Forman et al. |
| 2003/0003520 A1 | 1/2003 | Shan et al. |
| 2003/0109467 A1 | 6/2003 | Monia et al. |
| 2003/0130296 A1 | 7/2003 | Bauer et al. |
| 2004/0009961 A1 | 1/2004 | Borody |
| 2004/0176426 A1 | 9/2004 | Houze et al. |

(Continued)

FOREIGN PATENT DOCUMENTS

| | | |
|---|---|---|
| BE | 884722 A | 1/1980 |
| EP | 0607536 B1 | 1/2001 |

(Continued)

OTHER PUBLICATIONS

Aktories/Foerstermann/Hofmann/Starke, "Allgemeine und spezielle Pharmakologie und Toxikologie" Muenchen: Elsevier GmbH, 2005 ISBN: 978-3-437-44490-6; p. 609-616 (English translation of pp. 615-616 is attached).

Communication of a Notice of Opposition dated Aug. 18, 2022, issued for Application No. EP16747312.3 (Patent EP3253382), Patentee: Intercept Pharmaceuticals, Inc; Opponent: Stada Arzneimittel AG, 18 pages.

Cuperus, Frans J.C. et al. "Fibrate treatment for primary biliary cirrhosis" Current Opinion in Gastroenterology, 2014, vol. 30, No. 3, p. 279-286.

(Continued)

*Primary Examiner* — Yong S. Chong
(74) *Attorney, Agent, or Firm* — Hoxie & Associates LLC

(57) ABSTRACT

The present invention relates to a pharmaceutical composition comprising a combination of an FXR agonist and at least one lipid lowering agent (e.g., PPAR-alpha agonist, PPAR-delta agonist, PPAR-alpha and delta dual agonist, and/or statin). Also disclosed is use of the combination for the treatment or prevention of a FXR mediated disease or condition, such as primary biliary cirrhosis (PBC), primary sclerosing cholangitis (PSC), portal hypertension, bile acid diarrhea, NAFLD (nonalcoholic fatty liver disease), NASH (non-alcohol-induced steatohepatitis), and other chronic liver diseases. The combination of the present invention is useful for the treatment or prevention of conditions related to elevated lipid and liver enzyme levels. The present invention also relates to packs or kits including the pharmaceutical combination.

18 Claims, 14 Drawing Sheets

(56) References Cited

U.S. PATENT DOCUMENTS

| | | |
|---|---|---|
| 2005/0080064 A1 | 4/2005 | Pellicciari |
| 2006/0069070 A1 | 3/2006 | Fiorucci et al. |
| 2006/0252670 A1 | 11/2006 | Fiorucci et al. |
| 2007/0142340 A1 | 6/2007 | Pellicciari |
| 2007/0197606 A1 | 8/2007 | Burczynski et al. |
| 2007/0203155 A1 | 8/2007 | Epple et al. |
| 2008/0039435 A1 | 2/2008 | Pellicciari |
| 2008/0096921 A1 | 4/2008 | Navas, III et al. |
| 2008/0182832 A1 | 7/2008 | Pellicciari et al. |
| 2008/0286354 A1 | 11/2008 | Borody |
| 2008/0299118 A1 | 12/2008 | Hartman et al. |
| 2008/0300235 A1 | 12/2008 | Harnish et al. |
| 2009/0062526 A1 | 3/2009 | Yu et al. |
| 2009/0093524 A1 | 4/2009 | Bell et al. |
| 2009/0105343 A1 | 4/2009 | Campbell et al. |
| 2009/0131395 A1 | 5/2009 | Antonelli et al. |
| 2009/0163474 A1 | 6/2009 | Zhang et al. |
| 2009/0215748 A1 | 8/2009 | Harnish |
| 2009/0270460 A1 | 10/2009 | Bell et al. |
| 2009/0312297 A1 | 12/2009 | Hotamisligil et al. |
| 2010/0022498 A1 | 1/2010 | Pellicciari |
| 2010/0063018 A1 | 3/2010 | Pellicciari et al. |
| 2010/0069367 A1 | 3/2010 | Boren et al. |
| 2010/0152166 A1 | 6/2010 | Genin et al. |
| 2010/0172870 A1 | 7/2010 | Kremoser et al. |
| 2010/0184809 A1 | 7/2010 | Kremoser et al. |
| 2010/0210660 A1 | 8/2010 | Kremoser et al. |
| 2011/0105475 A1 | 5/2011 | Roche et al. |
| 2012/0053163 A1 | 3/2012 | Pellicciari |
| 2012/0232116 A1 | 9/2012 | Kremoser et al. |
| 2012/0283234 A1 | 11/2012 | Pellicciari et al. |
| 2014/0371190 A1 | 12/2014 | Pellicciari |
| 2016/0376279 A1 | 12/2016 | Evans et al. |
| 2022/0226350 A1 | 7/2022 | Macconell et al. |
| 2022/0280534 A1 | 9/2022 | Pruzanski et al. |

FOREIGN PATENT DOCUMENTS

| | | |
|---|---|---|
| GB | 860303 A | 1/1961 |
| WO | WO 2000/037057 | 6/2000 |
| WO | WO 2000/037077 A1 | 6/2000 |
| WO | WO 00/49992 A2 | 8/2000 |
| WO | WO 01/80852 A1 | 11/2001 |
| WO | WO 2002/024632 | 3/2002 |
| WO | WO 2006/044391 A1 | 4/2006 |
| WO | WO 2006/122977 A2 | 11/2006 |
| WO | WO 2008/039829 A2 | 4/2008 |
| WO | WO 2013/192097 A1 | 12/2013 |
| WO | WO 2014/066819 A1 | 5/2014 |
| WO | WO 2014/184271 A1 | 11/2014 |
| WO | WO 2016/127019 A2 | 8/2016 |

OTHER PUBLICATIONS

Flores Avegail et al., "Primary biliary cirrhosis in 2014" Current Opinion in Gastroenterology, 2014, vol. 30, No. 3, p. 245-252.

Lefebvre al., "Role of Bile Acids and Bile Acid Receptors in Metabolic Regulation" Physiol. Rev., 2009, vol. 89, p. 147-191.

Poupon et al. "Evidence-Based Treatment of Primary Biliary Cirrhosis" Digestive Diseases, 2014, vol. 32, p. 626-630.

Sorokin et al., "Primary biliary cirrhosis, hyperlipidemia, and atherosclerotic risk: A systematic review" Atherosclerosis, 2007, vol. 194, p. 293-299.

Yiman et al., "Obeticholic acid for treatment of primary biliary cirrhosis" Expert Opinion on Orphan Drugs, 2014, vol. 2, No. 12, p. 1351-1358.

Anders, S. et al., "Count-based differential expression analysis of RNA sequencing data using R and Bioconductor," Nature Protocols, vol. 8, Issue 9 (2013): 1765-86.

CAS No. 475479-34-6, Dec. 9, 2002, 2 pages.
CAS No. 331741-94-7, Apr. 18, 2001, 2 pages.
CAS No. 251565-85-2, Dec. 22, 1999, 2 pages.
CAS No. 495399-09-2, Feb. 27, 2003, 2 pages.
CAS No. 459789-99-2, Oct. 8, 2002, 2 pages.

Chen, W. et al. "Peroxisome Proliferator-Activated Receptor δ-Agonist, GW501516, Ameliorates Insulin Resistance, Improves Dyslipidaemia in Monosodium L-Glutamate Metabolic Syndrome Mice", Basic & Clinical Pharmacology & Toxicology, 2008, vol. 103, pp. 240-246.

Cipriani S. et al: "FXR Activation Reverses Insulin Resistance and Protects Against NASH Development", Gastroenterology, vol. 136, No. 5, Suppl. 1, 2009, pp. A420-A421.

Farrell G. "Should we lower lipids in nonalcoholic fatty liver disease?", Clinical Gastroenterology and Hepatology, 2014, vol. 12, No. 1, p. 152-155.

Fiorucci et al. "Targeting farnesoid X receptor for liver and metabolic disorders", Trends in Molecular Medicine, vol. 13, No. 7, 2007, pp. 298-309.

Fiorucci S. et al. "Cross-Talk between Farnesoid-X-Receptor (FXR) and Peroxisome Proliferator-Activated Receptor y Contributes to the Antifibrotic Activity of FXR Ligands in Rodent Models of Liver Cirrhosis", Journal of Pharmacology and Experimental Therapeutics, vol. 315, No. 1, 2005, pp. 58-68.

Folch, N. et al., "Metabolic response to a large starch meal after rest and exercise: comparison between men and women," European Journal of Clinical Nutrition, vol. 57, Issue 9 (2003): 1107-15.

Gadaleta, R. et al., "Farnesoid X receptor activation inhibits inflammation and preserves the intestinal barrier in inflammatory bowel disease," Gut, vol. 60, Issue 4 (2011): 463-72.

Ghonem and Boyer "Fibrates as Adjuvant Therapy for Chronic Cholestatic Liver Disease: Its Time Has Come", Hepatology, 2013, vol. 57, No. 5, p. 1691-1693.

Hanley, Karen et al. Activators of the Nuclear Hormone Receptors PPARa and FXR Accelerate the Development of the Fetal Epidermal Permeability Barrier. The Journal of Clinical Investigation vol. 100, No. 3, 1997, p. 705-712. Retrieved from the Internet. URL: http://contentassets.jci.org/manuscripts/119000/119583/JCI97119583.pdf.

Hirschfield et al. "Efficacy of Obeticholic Acid in Patients with Primary Biliary Cirrhosis and Inadequate Response to Ursodeoxycholic Acid", Gastroenterology, 2015, vol. 148, No. 4, p. 751-761.

Kanda et al. "Bezafibrate treatment: a new medical approach for PBC patients?", Journal of Gastroenterology, 2003, vol. 38, No. 6, p. 573-578.

Kattan E. et al. "Efficacy and safety of the farnesoid X receptor agonist obeticholic acid in patients with type 2 diabetes and non-alcoholic fatty liver disease" Gastroenterol. Latinoam, vol. 25, No. 1, p. 50-54 (2014).

Kim, I. et al., "Spontaneous hepatocarcinogenesis in farnesoid X receptor-null Mice," Carcinogenesis, vol. 28, Issue 5 (2007): 940-946.

Kleiner, D. et al, "Design and validation of a histological scoring system for nonalcoholic fatty liver disease," Hepatology, vol. 41, Issue 6 (2005): 1313-21.

Komoto et al. "New Strong Fibrates with Piperidine Moiety" Chem. Pharm. Bull. vol. 48, 12, 2000, p. 1978-1985.

Kostapanos, M. S. et al., Current role of fenofibrate in the prevention and management of nonalcoholic fatty liver disease. World Journal of Hepatology, Sep. 27, 2013, vol. 5, No. 9, p. 470-478.

Kramer, A. et al., "Causal analysis approaches in Ingenuity Pathway Analysis," Bioinformatics, vol. 30, Issue 4 (2014): 523-530.

Landrier J.F. et al. "Statin induction of liver fatty acid-binding protein (L-FABP) gene expression is peroxisome proliferator-activated receptor-alpha-dependent", The Journal of Biological Chemistry, 2004, vol. 278, No. 44, p. 45512-45518.

Langhi C. et al. "Activation of the farnesoid X receptor represses PCSK9 expression in human hepatocytes", FEBS Letters, 2018, vol. 582, p. 949-955.

Lee J. M. et al. "Nutrient-sensing nuclear receptors coordinate Autophagy", Nature, 2014, vol. 516, p. 112-115.

Levy, C. et al. Pilot study: fenofibrate for patients with primary biliary cirrhosis and an incomplete response to ursodeoxycholic acid. Alimentary Pharmacology and Therapeutics, 2010, vol. 33, No. 2, pp. 235-242.

(56) References Cited

OTHER PUBLICATIONS

Li, Y. et al., "Farnesoid X Receptor Ligands Inhibit Vascular Smooth Muscle Cell Inflammation and Migration," Arteriosclerosis, Thrombosis, and Vascular Biology, vol. 27 (2007): 2606-2611.

Liang, W. et al., "Establishment of a General NAFLD Scoring System for Rodent Models and Comparison to Human Liver Pathology," PlosOne, vol. 9 (2014): 1-17.

Mohamed D. et al. "Fenofibrate A peroxisome proliferator activated receptor-[alpha] agonist treatment ameliorates Concanavalin A-induced hepatitis in", European Journal of Pharmacology, vol. 721, No. 1, 2013, pp. 35-42.

Ohmoto, K. et al. "Long-term effect of bezafibrate on parameters of hepatic fibrosis in primary biliary cirrhosis", Journal of Gastroenterology, 2006, vol. 41, pp. 502-503.

Pellicciari et al. "6α-Ethyl-chenodeoxycholic acid (6-ECDCA), a potent and selective FXR agonist endowed with anticholestatic activity", Journal of Medicinal Chemistry, 2002, vol. 45, No. 17, p. 3569-3572.

Smets et al. "LBO-05: Bezafibrate improves the effect of obeticholic acid on cholestasis in patients with primary biliary cholangitis", Journal of Hepatology, 2019, vol. 70, p. e130.

Staels et al. "Therapeutic Roles of Peroxisome Proliferator-Activated Receptor Agonists" Diabetes, vol. 54, p. 2460-2470 (2005).

Stojakovic, T. et al. Low-dose atorvastatin improves dyslipidemia and vascular function in patients with primary biliary cirrhosis after one year of treatment. Atherosclerosis, 2010, vol. 209, No. 1, p. 178-183.

Tanabe J. et al. "Effects of Combined PPARy and PPARa Agonist Therapy on Reverse Cholesterol Transport in the Zucker Diabetic Fatty Rat" Diabetes, Obesity and Metabolism, vol. 10, Issue 9, p. 772-779 (2008).

Tanaka et al., "Biochemical responses to bezafibrate improve long-term outcome in asymptomatic patients with primary biliary cirrhosis refractory to UDCA", J Gastroenterol (2015), vol. 50, p. 675-682.

Trebicka J. et al. "Atorvastatin attenuates hepatic fibrosis in rats after bile duct ligation via decreased turnover of hepatic stellate cells", Journal of Hepatology, vol. 53, No. 4, 2010, pp. 702-712.

Verschuren, L. et al., "A systems biology approach to understand the pathophysiological mechanisms of cardiac pathological hypertrophy associated with rosiglitazone," BioMed Central Medical Genomics, vol. 7 (2014): 35.

Wang, X. et al., "The farnesoid X receptor modulates renal lipid metabolism and diet-induced renal inflammation, fibrosis, and proteinuria," American Journal of Physiology Renal Physiology, vol. 297, Issue 6 (2009): F1587-1596.

Wang, X. et al., "Diabetic Nephropathy Is Accelerated by Farnesoid X Receptor Deficiency and Inhibited by Farnesoid X Receptor Activation in a Type 1 Diabetes Model," Diabetes, vol. 59, Issue 11 (2010): 2916-2927.

Yang, F. et al., "Spontaneous Development of Liver Tumors in the Absence of the Bile Acid Receptor Farnesoid X Receptor," Cancer Research, vol. 67, Issue 3 (2007): 863-867.

Endocrinology & Diabetology, 2001, vol. 12, No. 2, p. 119-128.

Vascular Biology & Medicine, 2003, vol. 4, No. 4, p. 92-101.

Wei, Jia et al., "Progress on the development of farnesoid X receptor agonists", Chinese Journal of Medicinal Chemistry, 2010, vol. 20, No. 1, p. 64-69 (English summary included).

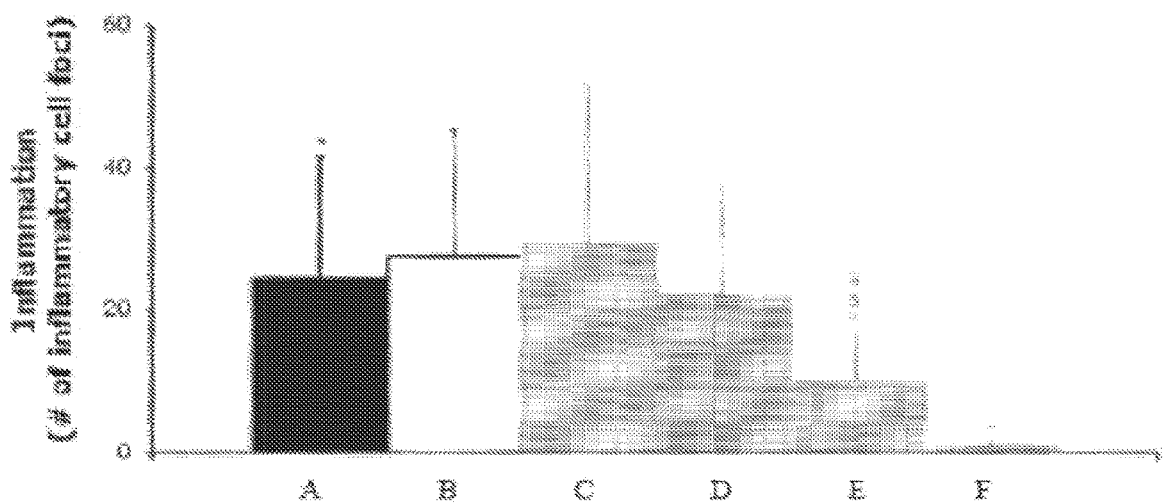

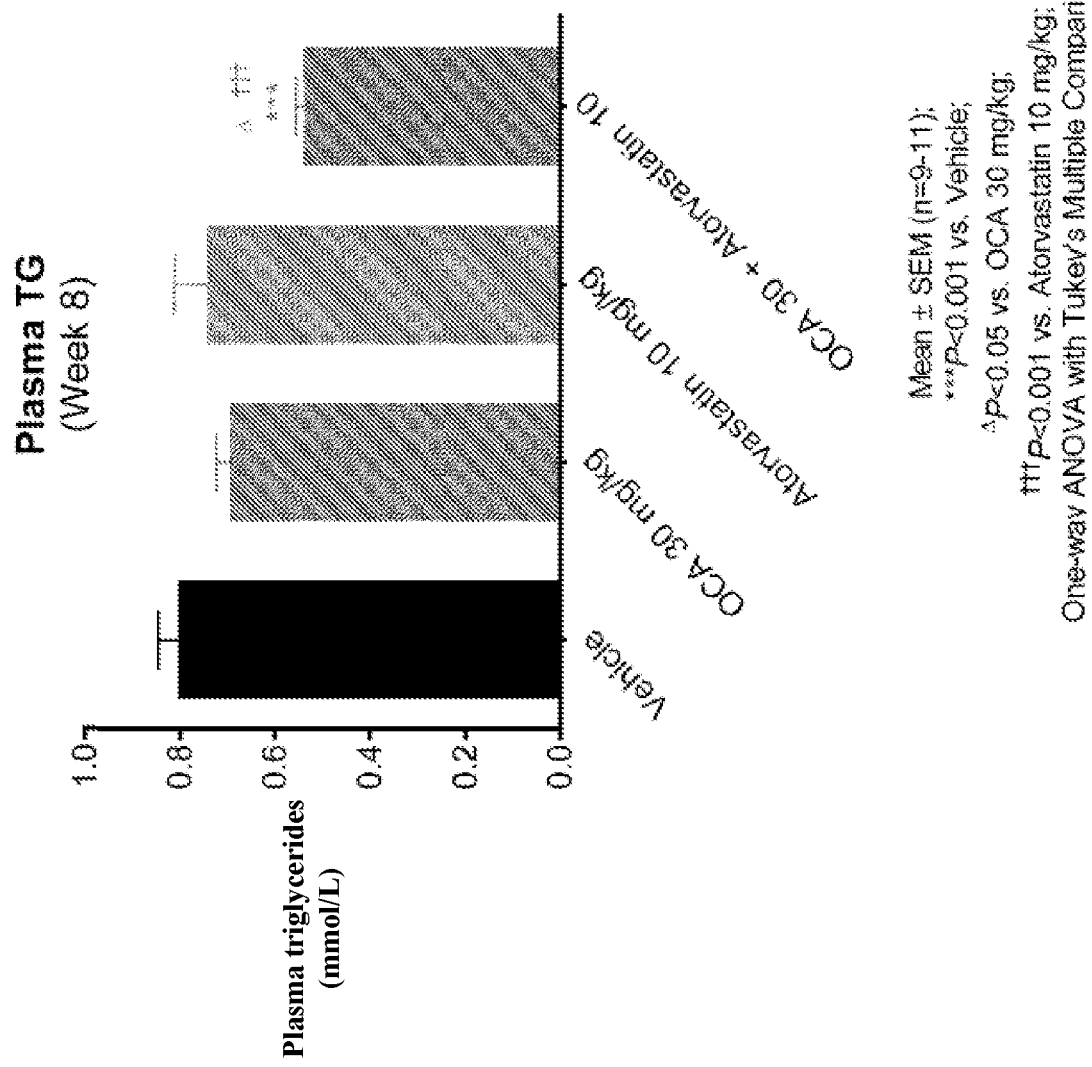

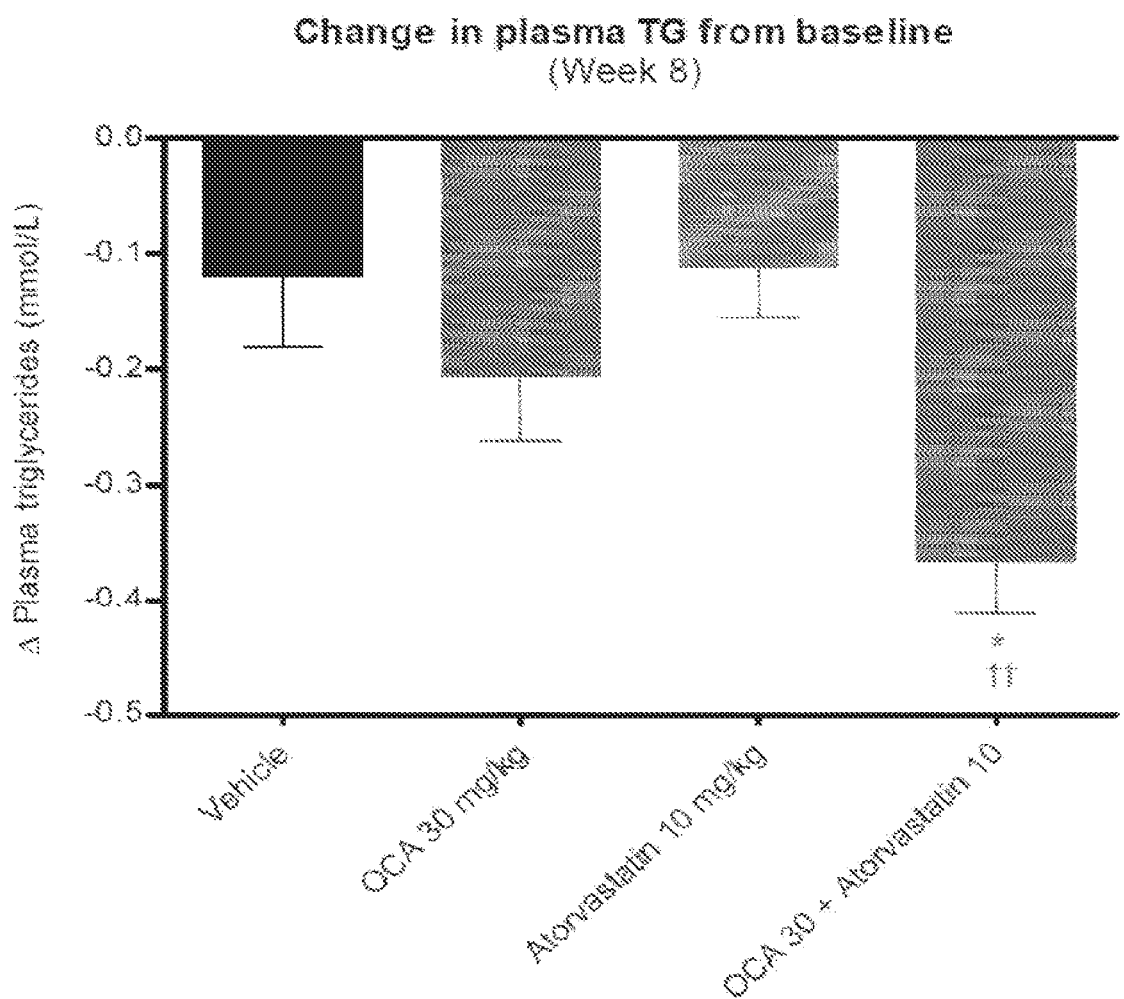

PHARMACEUTICAL COMPOSITIONS FOR COMBINATION THERAPY

CROSS REFERENCE TO RELATED APPLICATIONS

The present application is a continuation of U.S. Application Ser. No. 15/548,537, filed Aug. 3, 2017, now U.S. Pat. No. 11,311,557, which is the national stage entry of PCT/US2016/016694, filed Feb. 5, 2016, which claims the benefit of and priority from U.S. Provisional Application No. 62/113,134 filed Feb. 6, 2015.

BACKGROUND TO THE INVENTION

Elevated concentrations of circulating lipid compounds in the blood, such as cholesterol and triglycerides, accompany a number of conditions. These include Type II diabetes, primary biliary cirrhosis (PBC), primary sclerosing cholangitis (PSC), various chronic hepatitis states (Hepatitis B and C), NASH (non-alcoholic steatohepatitis), and arterial diseases including coronary artery disease, cerebrovascular arterial disease, peripheral vascular disease, aortic aneurysms and carotid atherosclerotic conditions. Various lipid-lowering techniques have been used in the past to treat and to prevent the vascular events (such as cardiac failure, embolism, heart attacks and strokes) that accompany hyperlipidemic states. Such treatments have included dietary changes and control of high triglyceride and cholesterol levels circulating in the blood. The latter have been treated generally pharmacologically and lately with various "statins". Included in the therapeutic agents used for treatment of conditions for elevated lipid levels are various fibric acid derivatives. Some older fibric acid derivatives including clofibrate have had a passing place in the treatment of conditions associated with elevated lipids, but more recently new fibrates including fenofibrate, gemfibrozil, ciprofibrate, and even more recently fibrates containing piperidine, 4-hydroxypiperidine, piperidin-3-ene, and piperazine have joined the ranks of anti-lipid therapies. These newer molecules have promising properties to reduce both cholesterol and triglycerides. However, in some situations a fibric acid derivative alone is inadequate in controlling the severe level of hyperlipidemia that is present in many patients. The side effect profile of a fibric acid derivative may also be improved from a reduction in dose such as in the presence of a combination therapy.

Accordingly, there is a need for an improved therapy for the treatment of conditions involving elevated concentrations of circulating lipid compounds in the blood, such as cholesterol and triglycerides.

BRIEF DESCRIPTION OF THE DRAWINGS

FIG. 3A is a bar graph showing the number of inflammatory cell foci from the treatment of OCA, low dose fenofibrate alone and in combination in APOE*3Leiden.CETP mice.

FIG. 5A is a bar graph showing the levels of plasma triglycerides in leptin-ob/ob mice treated with OCA and atorvastatin alone and in combination.

FIG. 5B is a bar graph showing the change in levels of plasma triglycerides from baseline in leptin-ob/ob mice treated with OCA and atorvastatin alone and in combination.

SUMMARY OF THE INVENTION

Figure 1A:
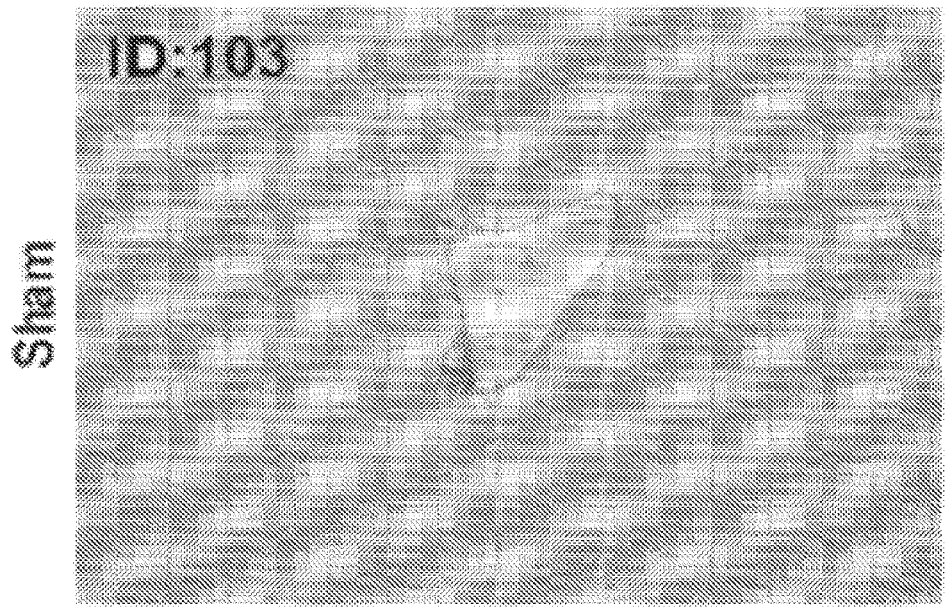
FIG. 1A is a representative photomicrograph of a Sirius-red stained liver section from sham BDL mice.
Figure 1B:
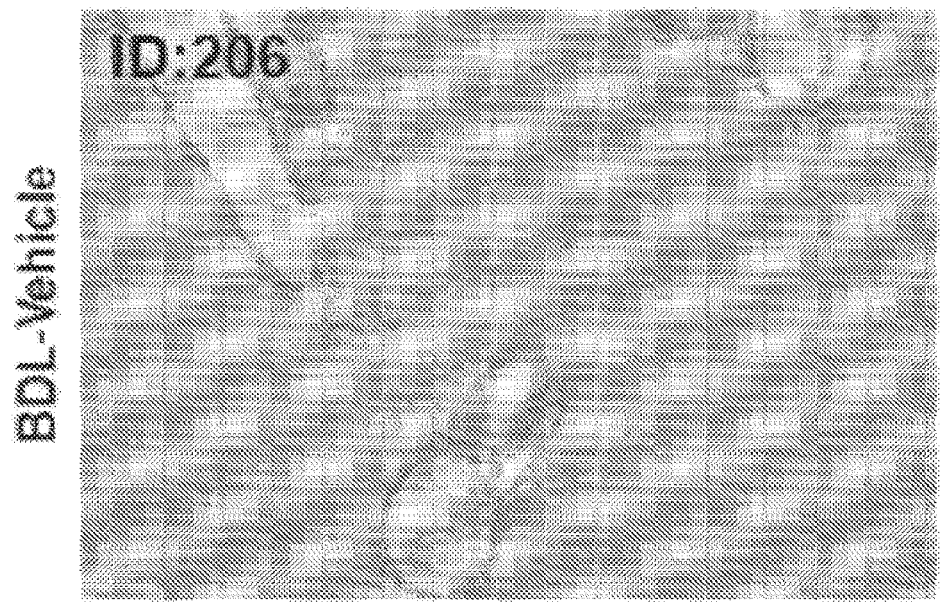
FIG. 1B is a representative photomicrograph of a Sirius-red stained liver section from BDL-vehicle treated mice.
Figure 1C:
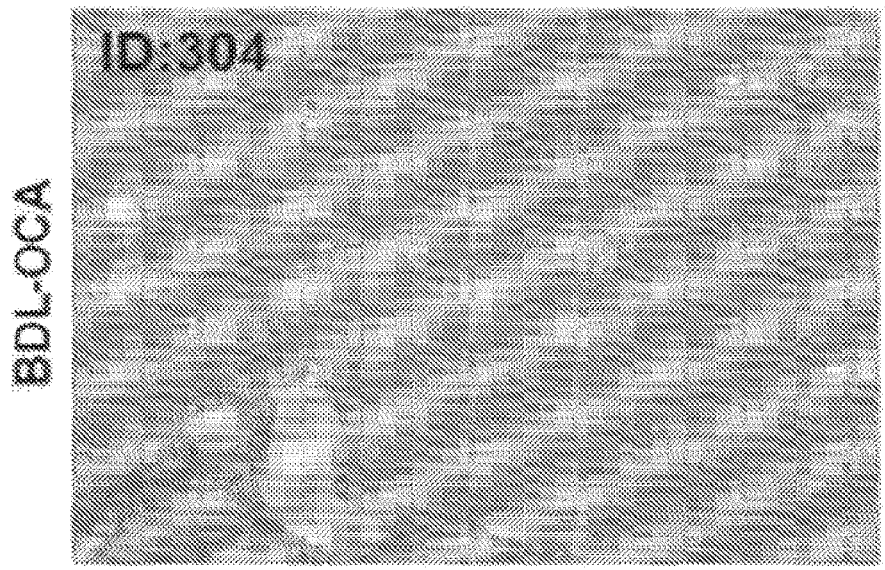
FIG. 1C is a representative photomicrograph of Sirius-red stained liver section from BDL-OCA treated mice.
Figure 1D:
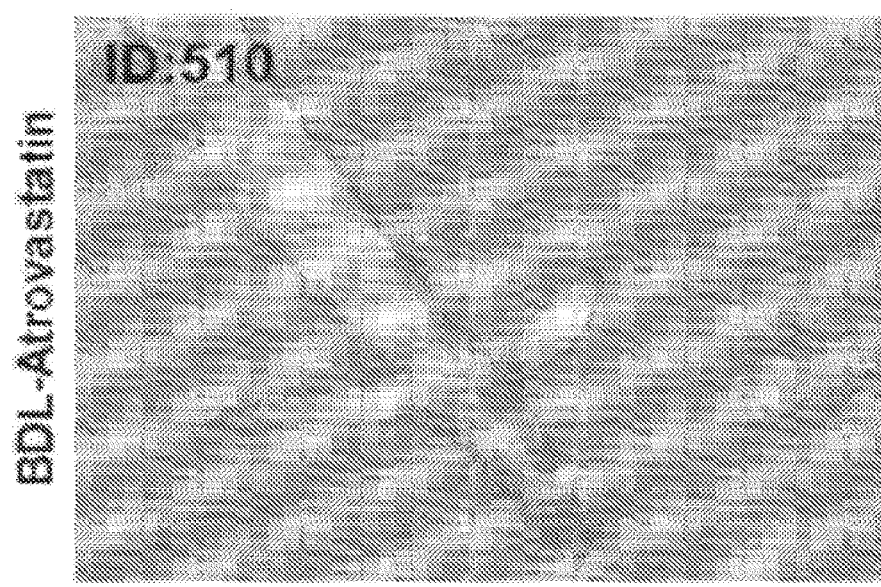
FIG. 1D is a representative photomicrograph of Sirius-red stained liver section from BDL-atorvastatin treated mice.
Figure 1E:
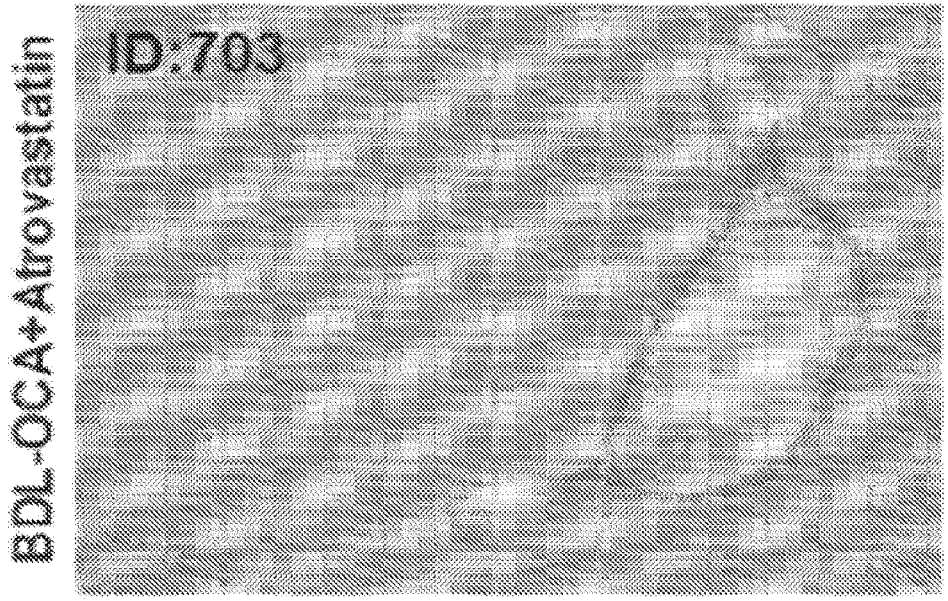
FIG. 1E is a representative photomicrograph of Sirius-red stained liver section from BDL-OCA-atorvastatin treated mice.

The present application relates to a pharmaceutical composition comprising (i) a first compound, (ii) at least one PPAR-alpha agonist, PPAR-delta agonist, and/or PPAR-alpha and delta dual agonist, and (iii) optionally one or more pharmaceutically acceptable carriers, wherein the first compound is an FXR agonist.

The present invention also relates to a pharmaceutical composition comprising (i) a first compound, (ii) at least one fibrate, and optionally (iii) one or more pharmaceutically acceptable carriers, wherein the first compound is an FXR agonist.

The present invention also relates to a pharmaceutical composition comprising (i) a first compound, (ii) at least one lipid lowering agent, and optionally (iii) one or more pharmaceutically acceptable carriers, wherein the first compound is an FXR agonist.

The present invention also relates to a pharmaceutical composition comprising (i) a first compound, (ii) at least one statin, and optionally (iii) one or more pharmaceutically acceptable carriers, wherein the first compound is an FXR agonist.

The present invention also relates to a pharmaceutical composition comprising (i) a first compound, (ii) at least one PPAR-alpha agonist, PPAR-delta agonist, and/or PPAR-alpha and delta dual agonist, (iii) at least one lipid lowering agent, and optionally (iv) one or more pharmaceutically acceptable carriers, wherein the first compound is an FXR agonist.

The present invention also relates to a pharmaceutical composition comprising (i) a first compound, (ii) at least one fibrate, (iii) at least one lipid lowering agent, and optionally (iv) one or more pharmaceutically acceptable carriers, wherein the first compound is an FXR agonist.

The present invention also relates to a pharmaceutical composition comprising (i) a first compound, (ii) at least one PPAR-alpha agonist, PPAR-delta agonist, and/or PPAR-alpha and delta dual agonist, (iii) at least one statin, and optionally (iv) one or more pharmaceutically acceptable carriers, wherein the first compound is an FXR agonist.

The present invention also relates to a pharmaceutical composition comprising (i) a first compound, (ii) at least one fibrate, (iii) at least one statin, and optionally (iv) one or more pharmaceutically acceptable carriers, wherein the first compound is an FXR agonist.

The present invention also relates to the therapeutic use of the pharmaceutical compositions of the present invention.

In one embodiment, the first compound is a compound of formula A:

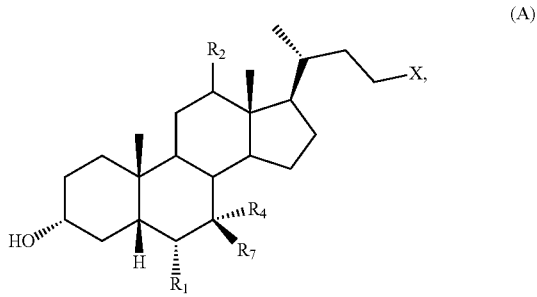

(A)

or a pharmaceutically acceptable salt or amino acid conjugate thereof, wherein $R_1$, $R_2$, $R_4$, $R_7$, and X are as defined herein.

The present invention also relates to methods for treating or preventing an FXR mediated disease or condition or a disease or condition in which elevated concentrations of circulating lipid compounds in the blood are involved, reducing the level of a liver enzyme, or inhibiting or reversing fibrosis, comprising administering a therapeutically effective amount of a pharmaceutical composition of the present invention to a subject in need thereof.

The present invention also relates to use of a pharmaceutical composition of the present invention for treating or preventing an FXR mediated disease or condition or a disease or condition in which elevated concentrations of circulating lipid compounds in the blood are involved, reducing the level of a liver enzyme, or inhibiting or reversing fibrosis.

The present invention also relates to use of a pharmaceutical composition of the present invention in the manufacture of a medicament for treating or preventing an FXR mediated disease or condition or a disease or condition in which elevated concentrations of circulating lipid compounds in the blood are involved, reducing the level of a liver enzyme, or inhibiting or reversing fibrosis.

The compositions and methods of the present invention address unmet needs in the treatment or prevention of a disease or disorder in which elevated concentrations of circulating lipid compounds in the blood, such as cholesterol and triglycerides, are involved.

DETAILED DESCRIPTION OF THE INVENTION

The present application is directed to a pharmaceutical composition comprising a first compound, at least one PPAR-alpha agonist, PPAR-delta agonist, and/or PPAR-alpha and delta or PPAR-alpha and gamma dual agonist, and optionally one or more pharmaceutically acceptable carriers, wherein the first compound is an FXR agonist.

In one example, the pharmaceutical composition comprises at least one PPAR-alpha agonist. In one example, the pharmaceutical composition comprises at least one PPAR-delta agonist. In one example, the pharmaceutical composition comprises at least one PPAR-alpha and delta dual agonist. In one example, the pharmaceutical composition comprises at least one PPAR-alpha and gamma dual agonist. In one example, the pharmaceutical composition comprises at least one PPAR-alpha agonist and at least one PPAR-delta agonist. In one example, the pharmaceutical composition comprises at least one PPAR-alpha agonist and at least one PPAR-alpha and delta dual agonist. In one example, the pharmaceutical composition comprises at least one PPAR-delta agonist and at least one PPAR-alpha and delta or PPAR-alpha and gamma dual agonist. In one example, the pharmaceutical composition comprises at least one PPAR-alpha agonist, at least one PPAR-delta agonist, and at least one PPAR-alpha and delta dual agonist. In one example, the PPAR-alpha agonist is a fibrate, such as the fibrates described herein. In one example, the PPAR-delta agonist is {4-[({4-methyl-2-[4-(trifluoromethyl)phenyl]-1,3-thiazol-5-yl}methyl)sulfanyl]-2-methylphenoxy}acetic acid (also known as GW501516, GW1516 and "Endurabol"), {2-methyl-4-[5-methyl-2-(4-trifluoromethyl-phenyl)-2H-[1,2,3]triazol-4-ylmethylsylfanyl]-phenoxy}-acetic acid, or [4-[[[2-[3-fluoro-4-(trifluoromethyl)phenyl]-4-methyl-5-thiazolyl]methyl]thio]-2-methyl phenoxy]-acetic acid, or a pharmaceutically acceptable salt thereof. In one example, the PPAR-alpha and delta dual agonist is 2-[2,6 dimethyl-4-[3-[4-(methylthio)phenyl]-3-oxo-1(E)-propenyl]phenoxyl]-2-methylpropanoic acid (also known as GFT505). In one example, the PPAR-alpha and gamma dual agonist is aleglitazar ((2S)-2-methoxy-3-[4-[2-(5-methyl-2-phenyl-4-oxazolyl)ethoxy]-7-benzothiophenyl]propanoic acid), muraglitazar (N-[(4-methoxyphenoxy)carbonyl]-N-{4-[2-(5-methyl-2-phenyl-1,3-oxazol-4-yl)ethoxy] benzyl}glycine), tesaglitazar ((2S)-2-ethoxy-3-[4-[2-(4-methyl sulfonyloxyphenyl)ethoxy]phenyl]propanoic acid), or saroglitazar ((2S)-2-ethoxy-3-[4-(2-{2-methyl-5-[4-(methylsulfanyl)phenyl]-1H-pyrrol-1-yl}ethoxy)phenyl] propanoic acid), or a pharmaceutically acceptable salt thereof. In one example, the PPAR-alpha and delta dual agonist is 2-[2,6 dimethyl-4-[3-[4-(methylthio)phenyl]-3-oxo-1(E)-propenyl]phenoxyl]-2-methylpropanoic acid, or a pharmaceutically acceptable salt thereof.

The present application is also directed to a pharmaceutical composition comprising a first compound, at least one fibrate, and optionally one or more pharmaceutically acceptable carriers, wherein the first compound is an FXR agonist. The FXR agonist can be any FXR agonist. The fibrate can be any fibrate. In one example, the fibrate is selected from any fibrates described herein.

The present application is also directed to a pharmaceutical composition comprising a first compound, at least one lipid lowering agent, and optionally one or more pharmaceutically acceptable carriers, wherein the first compound is an FXR agonist. The FXR agonist can be any FXR agonist. The lipid lowering agent can be any lipid lowering agent. In one example, the lipid lowering agent is selected from any lipid lowering agents described herein.

The present application is also directed to a pharmaceutical composition comprising a first compound, at least one statin, and optionally one or more pharmaceutically acceptable carriers, wherein the first compound is an FXR agonist. The FXR agonist can be any FXR agonist. The statin can be any statin. In one example, the statin is selected from any statins described herein.

The present application is also directed to a pharmaceutical composition comprising a first compound, at least one PPAR-alpha agonist, PPAR-delta agonist, and/or PPAR-alpha and delta or PPAR-alpha and gamma dual agonist, at least one lipid lowering agent, and optionally one or more pharmaceutically acceptable carriers, wherein the first compound is an FXR agonist.

The present application is also directed to a pharmaceutical composition comprising a first compound, at least one PPAR-alpha agonist, PPAR-delta agonist, and/or PPAR-alpha and delta or PPAR-alpha and gamma dual agonist, at least one statin, and optionally one or more pharmaceutically acceptable carriers, wherein the first compound is an FXR agonist. In one example, the PPAR-alpha agonist is a fibrate, such as the fibrates described herein. In one example, the PPAR-delta agonist is {4-[(({4-methyl-2-[4-(trifluoromethyl)phenyl]-1,3-thiazol-5-yl}methyl)sulfanyl]-2-methylphenoxy}acetic acid, {2-methyl-4-[5-methyl-2-(4-trifluoromethyl-phenyl)-2H-[1,2,3]triazol-4-ylmethylsylfanyl]-phenoxy}-acetic acid, or [4-[[[2-[3-fluoro-4-(trifluoromethyl)phenyl]-4-methyl-5-thiazolyl]methyl]thio]-2-methyl phenoxy]-acetic acid, or a pharmaceutically acceptable salt thereof. In one example, the PPAR-alpha and delta dual agonist is 2-[2,6 dimethyl-4-[3-[4-(methylthio)phenyl]-3-oxo-1(E)-propenyl]phenoxyl]-2-methylpropanoic acid. In one example, the PPAR-alpha and gamma dual agonist is aleglitazar, muraglitazar, tesaglitazar, or saroglitazar, or a pharmaceutically acceptable salt thereof. In one example, the PPAR-alpha and delta dual agonist is 2-[2,6 dimethyl-4-[3-[4-(methylthio)phenyl]-3-oxo-1(E)-propenyl]phenoxyl]-2-methylpropanoic acid, or a pharmaceutically acceptable salt thereof. In one example, the lipid lowering agent is selected from any lipid lowering agents described herein. In one example, the statin is selected from any statins described herein.

In one example, the first compound of the pharmaceutical composition is a compound of formula A:

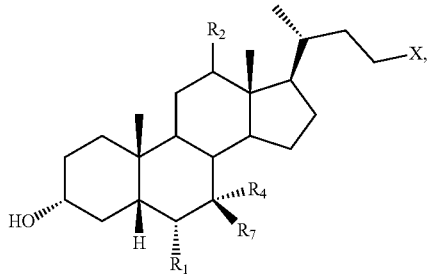

(A)

or a pharmaceutically acceptable salt or amino acid conjugate thereof, wherein:
R$_1$ is hydrogen or unsubstituted C$_1$-C$_6$ alkyl;
R$_2$ is hydrogen or α-hydroxyl;
X is C(O)OH, C(O)NH(CH$_2$)$_m$SO$_3$H, C(O)NH(CH$_2$)$_n$CO$_2$H or OSO$_3$H;
R$_4$ is hydroxyl or hydrogen;
R$_7$ is hydroxyl or hydrogen;
m is 1, 2, or 3; and
n is 1, 2, or 3.

In a further example, the first compound of the pharmaceutical composition is selected from formulae I and IA:

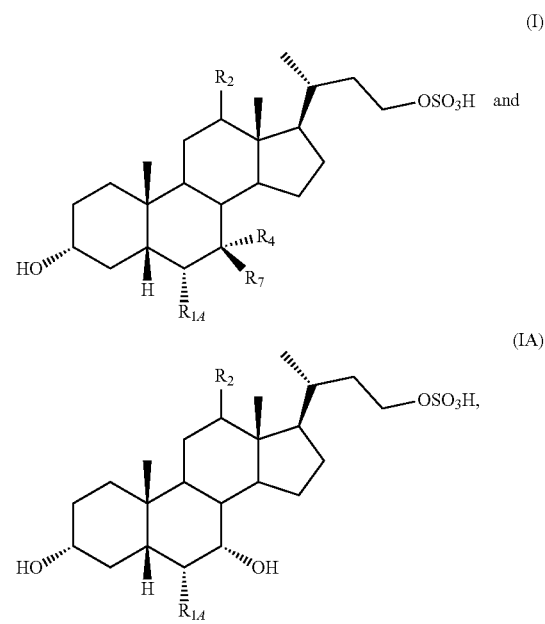

or a pharmaceutically acceptable salt or amino acid conjugate thereof, wherein
R$_{1A}$ is hydrogen or unsubstituted C$_1$-C$_6$ alkyl;
R$_2$ is hydrogen or α-hydroxyl;
R$_4$ is hydroxyl or hydrogen; and
R$_7$ is hydroxyl or hydrogen.

In one aspect, the first compound is a pharmaceutically acceptable salt. In one embodiment, the first compound is a sodium salt of formula I or IA. In another embodiment, the first compound is an ammonium salt of a compound of formula I or IA. In another embodiment, the first compound is a triethylammonium salt of a compound of formula I or IA.

In yet another example, the first compound of the pharmaceutical composition is selected from formulae II and IIA:

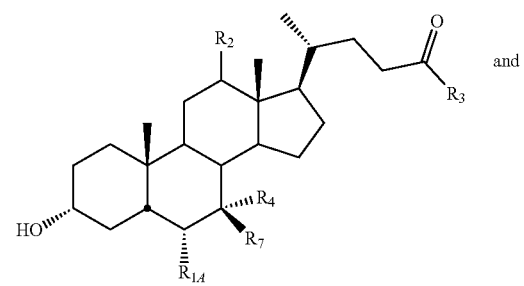

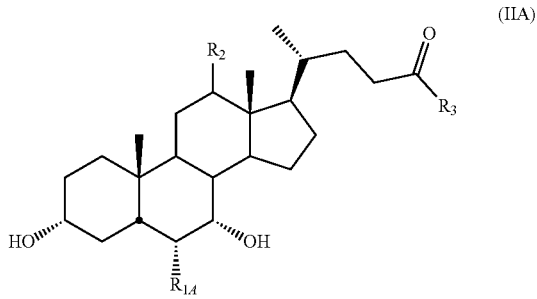

(IIA)

or a pharmaceutically acceptable salt or amino acid conjugate thereof, wherein:

$R_{1A}$ is hydrogen or unsubstituted $C_1$-$C_6$ alkyl;
$R_2$ is hydrogen or α-hydroxyl;
$R_3$ is hydroxyl, $NH(CH_2)_mSO_3H$, or $NH(CH_2)_nCO_2H$;
$R_4$ is hydroxyl or hydrogen;
$R_7$ is hydroxyl or hydrogen;
m is 1, 2, or 3; and
n is 1, 2, or 3.

In one example, the composition includes a first compound of formula A, I, IA, II or IIA, wherein $R_2$ is hydrogen.

In a further example, the composition includes a first compound of formula A, wherein $R_1$ is unsubstituted $C_1$-$C_6$ alkyl. In one aspect, the composition includes a first compound of formula A, wherein $R_1$ is unsubstituted $C_1$-$C_3$ alkyl. In one aspect, the composition includes a first compound of formula A, wherein $R_1$ is selected from methyl, ethyl, and propyl. In one aspect, the composition includes a first compound of formula A, wherein $R_1$ is ethyl.

In a further example, the composition includes a first compound of formula I, IA, II, or IIA, wherein $R_{1A}$ is unsubstituted $C_1$-$C_6$ alkyl. In one aspect, the composition includes a first compound of formula I, IA, II, or IIA, wherein $R_{1A}$ is unsubstituted $C_1$-$C_3$ alkyl. In one aspect, the composition includes a first compound of formula I, IA, II, or IIA, wherein $R_{1A}$ is selected from methyl, ethyl, and propyl. In one aspect, the composition includes a first compound of formula I, IA, II, or IIA, wherein Ria is ethyl.

In a further example, the composition includes a first compound of formula A, wherein X is selected from C(O)OH, $C(O)NH(CH_2)_mSO_3H$, and $C(O)NH(CH_2)_nCO_2H$. In one aspect, the composition includes a first compound of formula A, wherein X is selected from C(O)OH, $C(O)NH(CH_2)SO_3H$, $C(O)NH(CH_2)CO_2H$, $C(O)NH(CH_2)_2SO_3H$, $C(O)NH(CH_2)_2CO_2H$. In one aspect, the composition includes a first compound of formula A, wherein X is C(O)OH. In one aspect, the composition includes a first compound of formula A, wherein X is $OSO_3H$. In one aspect, the composition includes a first compound of formula A, wherein the first compound is a pharmaceutically acceptable salt. The pharmaceutically acceptable salt can be any salt. In one aspect, the composition includes a first compound of formula A, wherein X is $OSO_3^-Na^+$. In one aspect, the composition includes a first compound of formula A, wherein X is $OSO_3^-NHEt_3^+$. In one aspect, the amino acid conjugate is a glycine conjugate. In one aspect, the amino acid conjugate is a taurine conjugate.

In yet another example, the composition includes a first compound of formula II or IIA, wherein $R_3$ is selected from OH, $NH(CH_2)SO_3H$, $NH(CH_2)CO_2H$, $NH(CH_2)_2SO_3H$, and $NH(CH_2)_2CO_2H$. In one aspect, the composition includes a first compound of formula II or IIA, wherein $R_3$ is OH.

In a further example, the composition includes a first compound of formula A, I, or II, wherein $R_4$ is hydroxyl and $R_7$ is hydrogen.

In a further example, the composition includes a first compound of formula A, wherein $R_1$ is selected from methyl, ethyl and propyl, $R_4$ is OH, $R_7$ is H, and $R_2$ is H.

In a further example, the composition includes a first compound of formula I or II, wherein $R_{1A}$ is selected from methyl, ethyl and propyl, $R_4$ is OH, $R_7$ is H, and $R_2$ is H.

In a further example, the composition includes a first compound of formula IA or IIA, wherein $R_{1A}$ is selected from methyl, ethyl and propyl, and $R_2$ is H.

In a further example, the composition includes a first compound selected from

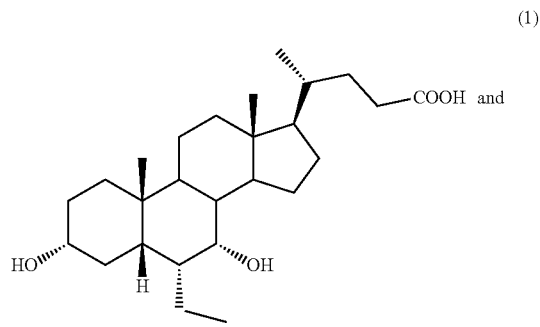

(1)

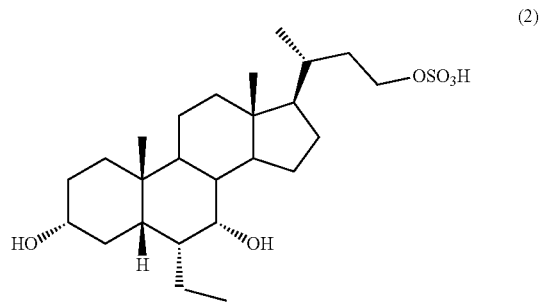

(2)

or a pharmaceutically acceptable salt or amino acid conjugate thereof.

In yet a further example, the composition includes a first compound is a pharmaceutically acceptable salt selected from

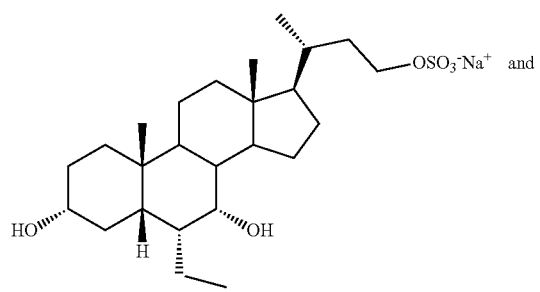

(3)

(4)

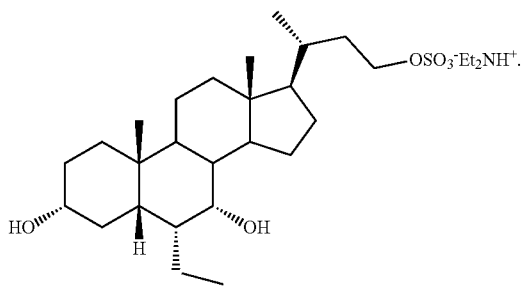

Compounds of formulae I, IA, II, and IIA are subsets of compounds of formula A. Features described herein for compounds of formula A apply equally to compounds of formulae I, IA, II, and IIA. The present application also describes the pharmaceutical compositions, packs or kits, and therapeutic uses of the combination.

One of the problems to be solved by the present invention is the identification of combination therapies for the treatment or prevention of conditions related to elevated concentrations of circulating lipid compounds in the blood, such as cholesterol and triglycerides e.g., a cholestatic liver condition such as PBC, as well as for the reduction of circulating lipid compounds (e.g., cholesterol, LDL, and triglycerides) in the blood, and for the reduction of bilirubin and/or liver enzymes, such as alkaline phosphatase (ALP, AP, or Alk Phos), alanine aminotransferase (ALT), aspartate aminotransferase (AST), gamma-glutamyl transpeptidase (GGT), lactate dehydrogenase (LDH), and 5' nucleotidase. Although drugs for conditions related to elevated lipid levels and/or liver enzyme levels are available, these drugs are often not suitable for many patients for a variety of reasons. For example, certain drugs are ineffective for patients who have developed drug resistance to, e.g., ursodeoxycholic acid. As another example, many statin drugs have adverse effects such as muscle problems, cognitive loss, neuropathy, pancreatic and hepatic dysfunction, and sexual dysfunction. Some drugs may be inadequate for the treatment when administered alone. For example, in some situations one lipid lowering agent alone is inadequate in controlling the severe level of hyperlipidemia that is present in many patients. Some drugs may require administration of high doses, or more frequent administration, due to extensive metabolism into inactive or less potent metabolites. The combination therapies described herein can solve the problems mentioned above and can have one or more advantages of, e.g., synergism, reducing the number of daily doses without the drug losing efficacy, lowering lipids (both cholesterol and triglycerides) in patients whose elevated lipid levels are resistant to therapy in PBC, improved potency, selectivity, tissue penetration, half-life, and/or metabolic stability.

In the compositions, packs or kits, methods and uses of the present invention, the first compound may be the free acid or it may be a pharmaceutically acceptable salt amino acid conjugate (e.g., glycine or taurine conjugate). In one aspect, the first compound is any FXR agonist. In one aspect, the first compound is a compound of formula A. In one aspect, the first compound is a compound of formula I or IA. In one aspect, the first compound is a compound of formula IA. In one aspect, the first compound is a compound of formula II or IIA. In one aspect, the first compound is a compound of formula IIA. In one aspect, the first compound is obeticholic acid (Compound 1). In one aspect, the first compound is Compound 2. In one aspect, the first compound is the pharmaceutically acceptable salt Compound 3. In one aspect, the first compound is the pharmaceutically acceptable salt Compound 4.

In the compositions, packs or kits, methods and uses of the present invention, the fibrate can be any fibrate. In one aspect, the fibrate is selected from the group consisting of fenofibrate, bezafibrate, beclobrate, binifibrate, ciprofibrate, clinofibrate, clofibrate, clofibric acid, etofibrate, gemfibrozil, nicofibrate, pirifibrate, ronifibrate, simfibrate, theofibrate, tocofibrate, plafibride, and a pharmaceutically acceptable salt and ester thereof, and derivatives of 2-phenoxy-2-methylpropanoic acid in which the phenoxy moiety is substituted with an optionally substituted residue of piperidine, 4-hydroxypiperidine, piperid-3-ene or piperazine, as disclosed in European Patent Application Publication No. EP0607536. In one aspect, the fibrate is selected from the group consisting of bezafibrate, ciprofibrate, clofibrate, fenofibrate, gemfibrozil, binifibrate, clinofibrate, clofibric acid, nicofibrate, pirifibrate, plafibride, ronifibrate, theofibrate, tocofibrate, and a pharmaceutically acceptable salt and ester thereof, and derivatives of 2-phenoxy-2-methylpropanoic acid, in which the phenoxy moiety is substituted with an optionally substituted residue of piperidine, 4-hydroxypiperidine, piperid-3-ene or piperazine, as disclosed in European Patent Application Publication No. EP0607536. An example of the latter group of substances is 2-[3-[1-(4-fluorobenzoyl)piperidin-4-yl]phenoxy-2-methyl-propanoic acid. For example, the fibrate is bezafibrate, fenofibrate, gemfibrozil, ciprofibrate, clofibrate, clofibric acid, or a pharmaceutically acceptable salt or ester thereof. For example, the fibrate is fenofibrate or a pharmaceutically acceptable salt selected from choline, ethanolamine, diethanolamine, piperazine, calcium, and tromethamine. For example, the fibrate is clofibrate or a pharmaceutically acceptable salt or ester thereof, such as etofibrate or aluminum clofibrate. For example, the fibrate is bezafibrate. For example, the fibrate is a derivative of 2-phenoxy-2-methylpropanoic acid such as 2-[3-[1-(4-fluorobenzoyl)-piperidin-4-yl]phenoxyl-2-methylpropanoic acid.

In one embodiment, the first compound is the free acid of a compound of formula A, and the at least one fibrate is selected from bezafibrate, fenofibrate, gemfibrozil, ciprofibrate, clofibrate, and a pharmaceutically acceptable salt or ester thereof.

In one embodiment, the first compound is a pharmaceutically acceptable salt of compound of formula A, and the at least one fibrate is selected from bezafibrate, fenofibrate, gemfibrozil, ciprofibrate, clofibrate, and a pharmaceutically acceptable salt or ester thereof.

In one embodiment, the first compound is the glycine conjugate of a compound of formula A, and the at least one fibrate is selected from bezafibrate, fenofibrate, gemfibrozil, ciprofibrate, clofibrate, and a pharmaceutically acceptable salt or ester thereof.

In one embodiment, the first compound is the taurine conjugate of a compound of formula A, and the at least one fibrate is selected from bezafibrate, fenofibrate, gemfibrozil, ciprofibrate, clofibrate, and pharmaceutically acceptable salts or esters thereof.

In one embodiment, the first compound is a compound of formula A or a pharmaceutically acceptable salt or amino acid conjugate, and the at least one fibrate is 2-[3-[1-(4-fluorobenzoyl)-piperidin-4-yl]phenoxyl-2-methylpropanoic acid.

In one embodiment, the first compound is a compound of formula A or a pharmaceutically acceptable salt or amino acid conjugate, and the at least one PPAR-delta agonist is {4-[({4-methyl-2-[4-(trifluoromethyl)phenyl]-1,3-thiazol-5-yl}methyl)sulfanyl]-2-methylphenoxy}acetic acid, {2-methyl-4-[5-methyl-2-(4-trifluoromethyl-phenyl)-2H-[1,2,3]triazol-4-ylmethylsylfanyl]-phenoxy}-acetic acid, or [4-[[[2-[3-fluoro-4-(trifluoromethyl)phenyl]-4-methyl-5-thiazolyl]methyl]thio]-2-methyl phenoxy]-acetic acid, or a pharmaceutically acceptable salt thereof.

In one embodiment, the first compound is a compound of formula A or a pharmaceutically acceptable salt or amino acid conjugate, and the at least one PPAR-alpha and delta dual agonist is 2-[2,6 dimethyl-4-[3-[4-(methylthio)phenyl]-3-oxo-1(E)-propenyl]phenoxyl]-2-methylpropanoic acid. In one embodiment, the first compound is a compound of formula A or a pharmaceutically acceptable salt or amino acid conjugate, and the at least one PPAR-alpha and gamma dual agonist is aleglitazar, muraglitazar, tesaglitazar, or saroglitazar, or a pharmaceutically acceptable salt thereof. In one example, the PPAR-alpha and delta dual agonist is 2-[2,6 dimethyl-4-[3-[4-(methylthio)phenyl]-3-oxo-1(E)-propenyl]phenoxyl]-2-methylpropanoic acid, or a pharmaceutically acceptable salt thereof.

In the compositions, packs or kits, methods and uses of the present invention, the statin can be any statin. In one aspect, the statin is selected from the group consisting of simvastatin, fluvastatin, pravastatin, rivastatin, mevastatin, atorvastatin, cerivastatin, lovastatin, pitavastatin, fluindostatin, velostatin, dalvastatin, rosuvastatin, dihydrocompactin, and compactin.

In one embodiment, the first compound is the free acid of a compound of formula A, and the at least one statin is selected from simvastatin, fluvastatin, pravastatin, rivastatin, mevastatin, atorvastatin, cerivastatin, lovastatin, pitavastatin, fluindostatin, velostatin, dalvastatin, rosuvastatin, dihydrocompactin, and compactin.

In one embodiment, the first compound is a pharmaceutically acceptable salt of compound of formula A, and the at least one statin is selected from simvastatin, fluvastatin, pravastatin, rivastatin, mevastatin, atorvastatin, cerivastatin, lovastatin, pitavastatin, fluindostatin, velostatin, dalvastatin, rosuvastatin, dihydrocompactin, and compactin.

In one embodiment, the first compound is the glycine conjugate of a compound of formula A, and the at least one statin is selected from simvastatin, fluvastatin, pravastatin, rivastatin, mevastatin, atorvastatin, cerivastatin, lovastatin, pitavastatin, fluindostatin, velostatin, dalvastatin, rosuvastatin, dihydrocompactin, and compactin.

In one embodiment, the first compound is the taurine conjugate of a compound of formula A, and the at least one statin is selected from simvastatin, fluvastatin, pravastatin, rivastatin, mevastatin, atorvastatin, cerivastatin, lovastatin, pitavastatin, fluindostatin, velostatin, dalvastatin, rosuvastatin, dihydrocompactin, and compactin.

The invention also comprehends an isotopically-labeled first compound or a pharmaceutically acceptable salt or amino acid conjugate thereof, which has a structure that is identical to that of the first compound of the present invention (e.g., a compound of formula A, I, IA, II, or IIA), but for the fact that one or more atoms are replaced by an atom having an atomic mass or mass number different from the atomic mass or mass number most commonly found in nature. Examples of isotopes that can be incorporated into the first compound or a pharmaceutically acceptable salt or amino acid conjugate thereof, include isotopes of hydrogen, carbon, nitrogen, fluorine, such as $^3$H, $^{11}$C, $^{14}$C and $^{18}$F.

The first compound or a pharmaceutically acceptable salt or amino acid conjugate thereof that contain the aforementioned isotopes and/or other isotopes of other atoms is within the scope of the present invention. Isotopically-labeled first compound or a pharmaceutically acceptable salt or amino acid conjugate thereof, for example, a first compound into which a radioactive isotopes such as $^3$H and/or $^{14}$C are incorporated, is useful in drug and/or substrate tissue distribution assays. Tritiated, i.e., $^3$H, and carbon-14, i.e., $^{14}$C, isotopes are used for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be used in some circumstances. Isotopically labeled first compound or a pharmaceutically acceptable salt or amino acid conjugate thereof can generally be prepared by carrying out the procedures disclosed in the Schemes and/or in the Examples of the invention, by substituting a readily available isotopically labeled reagent for a non-isotopically labeled reagent. In one embodiment, obeticholic acid, or pharmaceutically acceptable salts or amino acid conjugates thereof are not isotopically labelled.

The present invention also provides a method for treating or preventing a disease or condition, comprising administering a therapeutically effective amount of a pharmaceutical composition of the present invention to a subject in need thereof.

In one embodiment, the disease or condition is an FXR mediated disease or condition. Examples of the FXR mediated diseases or conditions include, but not limited to, liver diseases (including cholestatic and non-cholestatic liver diseases) such as primary biliary cirrhosis (PBC), primary sclerosing cholangitis (PSC), biliary atresia, portal hypertension, bile acid diarrhea, chronic liver disease, nonalcoholic fatty liver disease (NAFLD), nonalcoholic steatohepatitis (NASH), hepatitis C infection, alcoholic liver disease, liver damage due to progressive fibrosis, and liver fibrosis. Examples of FXR mediated diseases also include hyperlipidemia, high LDL-cholesterol, high HDL-cholesterol, high triglycerides, and cardiovascular disease.

NAFLD is a medical condition that is characterized by the buildup of fat (called fatty infiltration) in the liver. NAFLD is one of the most common causes of chronic liver disease, and encompasses a spectrum of conditions associated with lipid deposition in hepatocytes. It ranges from steatosis (simple fatty liver), to nonalcoholic steatohepatitis (NASH), to advanced fibrosis and cirrhosis. The disease is mostly silent and is often discovered through incidentally elevated liver enzyme levels. NAFLD is strongly associated with obesity and insulin resistance and is currently considered by many as the hepatic component of the metabolic syndrome.

Nonalcoholic steatohepatitis (NASH) is a condition that causes inflammation and accumulation of fat and fibrous (scar) tissue in the liver. Liver enzyme levels in the blood may be more elevated than the mild elevations seen with nonalcoholic fatty liver (NAFL). Although similar conditions can occur in people who abuse alcohol, NASH occurs in those who drink little to no alcohol. NASH affects 2 to 5 percent of Americans, and is most frequently seen in people with one of more of the following conditions: obesity, diabetes, hyperlipidemia, insulin resistance, uses of certain medications, and exposure to toxins. NASH is an increasingly common cause of chronic liver disease worldwide and is associated with increased liver-related mortality and hepatocellular carcinoma, even in the absence of cirrhosis. NASH progresses to cirrhosis in 15-20% of affected individuals and is now one of the leading indications for liver transplantation in the United States. At present there are no approved therapies for NASH.

In one embodiment, the disease or condition is hyperlipidemia. In one embodiment, the disease or condition is a cholestatic liver disease. In one embodiment, the disease or condition is PBC. In another embodiment, the disease or condition is a cardiovascular disease. In another embodiment, the cardiovascular disease is atherosclerosis, hypercholesterolemia, or hypertriglyceridemia.

The present invention also provides a method for treating or preventing NAFLD or NASH. In one embodiment, the present invention provides a method for treating or preventing NAFLD or NASH that is associated with hyperlipidemia. In one embodiment, the present invention provides a method for treating or preventing NASH. In one embodiment, the present invention provides a method for treating or preventing NASH that is associated with hyperlipidemia.

The present invention also provides a method for inhibiting or reversing fibrosis, comprising administering a therapeutically effective amount of a pharmaceutical composition of the present invention to a subject in need thereof. In one embodiment, the subject is not suffering from a cholestatic condition. In another embodiment, the subject is suffering from a cholestatic condition.

In one embodiment, the subject is not suffering from a cholestatic condition associated with a disease or condition selected from the group consisting of primary liver and biliary cancer (including hepatocellular carcinoma), colorectal cancer, metastatic cancer, sepsis, chronic total parenteral nutrition, cystic fibrosis, and granulomatous liver disease. In embodiments, the fibrosis to be inhibited or reversed occurs in an organ where FXR is expressed.

In one embodiment, a cholestatic condition is defined as having an abnormally elevated serum level of alkaline phosphatase, γ-glutamyl transpeptidase (GGT), and/or 5' nucleotidase. In another embodiment, a cholestatic condition is further defined as presenting with at least one clinical symptom. In one embodiment, the symptom is itching (pruritus). In another embodiment, a cholestatic condition is selected from the group consisting of primary biliary cirrhosis (PBC), primary sclerosing cholangitis (PBS), drug-induced cholestasis, hereditary cholestasis, biliary atresia, and intrahepatic cholestasis of pregnancy.

In one embodiment, the fibrosis is selected from the group consisting of liver fibrosis, kidney fibrosis, and intestinal fibrosis.

In one embodiment, the subject has liver fibrosis associated with a disease selected from the group consisting of hepatitis B; hepatitis C; parasitic liver diseases; post-transplant bacterial, viral and fungal infections; alcoholic liver disease (ALD); non-alcoholic fatty liver disease (NAFLD); non-alcoholic steatohepatitis (NASH); liver diseases induced by methotrexate, isoniazid, oxyphenistatin, methyldopa, chlorpromazine, tolbutamide, or amiodarone; autoimmune hepatitis; sarcoidosis; Wilson's disease; hemochromatosis; Gaucher's disease; types III, IV, VI, IX and X glycogen storage diseases; $\alpha_1$-antitrypsin deficiency; Zellweger syndrome; tyrosinemia; fructosemia; galactosemia; vascular derangement associated with Budd-Chiari syndrome, veno-occlusive disease, or portal vein thrombosis; and congenital hepatic fibrosis.

In another embodiment, the subject has intestinal fibrosis associated with a disease selected from the group consisting of Crohn's disease, ulcerative colitis, post-radiation colitis, and microscopic colitis.

In another embodiment, the subject has renal fibrosis associated with a disease selected from the group consisting of diabetic nephropathy, hypertensive nephrosclerosis, chronic glomerulonephritis, chronic transplant glomerulopathy, chronic interstitial nephritis, and polycystic kidney disease.

The present invention also provides a method for treating or preventing all forms of conditions related to elevated lipid levels. In one embodiment, the condition is hyperlipidemia where it is associated with a condition selected from resistant primary biliary cirrhosis; primary biliary cirrhosis where there is associated liver function test elevation and hyperlipidemia, primary sclerosing cholangitis, non-alcohol-induced steatohepatitis; and chronic liver disease associated with hepatitis B, C or alcohol. In another embodiment, the present invention provides a method for treating or preventing hyperlipidemia where the hyperlipidemia is primary hyperlipidemia with or without a genetic component, or hyperlipidemia associated with coronary artery disease, cerebrovascular arterial disease, peripheral vascular disease, aortic aneurisms, or carotid atherosclerosis.

In one aspect, the present invention provides a method for treating or preventing primary sclerosing cholangitis for similar biochemical abnormalities, as well as chronic hepatitis caused by hepatitis B, C or by alcohol. In one aspect, the present invention provides a method for treating or preventing other arterial disorders associated with hyperlipidemia. In one aspect, the present invention provides a method for treating or preventing hypertriglyceridemia.

The present invention also provides a method for reducing lipid levels (i.e., amount of lipid), such as in the blood, comprising administering a therapeutically effective amount of a pharmaceutical composition of the present invention to a subject in need thereof. In one embodiment, the method of the present invention reduces the lipid levels by at least 10%, 20%, 30%, 40%, 50%, 60%, 70%, 80%, or 90%, as compared to a control subject (e.g., a subject not administered with the composition of the present invention). In one embodiment, the subject has elevated levels of lipid, as compared to a healthy subject (e.g., an individual without a disease or condition, such as those described herein). In one embodiment, the method of the present application reduces the levels of lipid to normal levels (e.g., similar to the lipid levels in an individual without a disease or condition, such as those described herein).

In one embodiment, the lipid is cholesterol. In one embodiment, the method of the present invention reduces cholesterol levels by at least 10%, 20%, 30%, 40%, 50%, 60%, 70%, 80%, or 90%, as compared to a control subject (e.g., a subject not administered with the composition of the present invention). In one embodiment, the subject has elevated levels of cholesterol, as compared to a healthy subject (e.g., an individual without a disease or condition, such as those described herein). In one embodiment, the method of the present invention reduces cholesterol levels below 400 mg/L, 350 mg/L, 300 mg/L, 250 mg/L, 240 mg/L, 230 mg/L, 220 mg/L, 210 mg/L, 200 mg/L, 190 mg/L, 180 mg/L, 170 mg/L, 160 mg/L, or 150 mg/L. In one embodiment, the method of the present invention reduces cholesterol levels below 200 mg/L, 190 mg/L, 180 mg/L, 170 mg/L, 160 mg/L, or 150 mg/L.

In one embodiment, the cholesterol is LDL. In one embodiment, the method of the present invention reduces LDL levels by at least 10%, 20%, 30%, 40%, 50%, 60%, 70%, 80%, or 90%, as compared to a control subject (e.g., a subject not administered with the composition of the present invention). In one embodiment, the subject has elevated levels of LDL, as compared to a healthy subject (e.g., an individual without a disease or condition, such as those described herein). In one embodiment, the method of the present invention reduces LDL levels below 300 mg/L, 200 mg/L, 190 mg/L, 180 mg/L, 170 mg/L, 160 mg/L, 150 mg/L, 140 mg/L, 130 mg/L, 120 mg/L, 110 mg/L, 100 mg/L, 90 mg/L, 80 mg/L, 70 mg/L, 60 mg/L, or 50 mg/L. In one embodiment, the method of the present invention reduces LDL levels below 160 mg/L, 150 mg/L, 140 mg/L, 130 mg/L, 120 mg/L, 110 mg/L, 100 mg/L, 90 mg/L, 80 mg/L, 70 mg/L, 60 mg/L, or 50 mg/L. In one embodiment, the method of the present invention reduces LDL levels below 130 mg/L, 120 mg/L, 110 mg/L, 100 mg/L, 90 mg/L, 80 mg/L, 70 mg/L, 60 mg/L, or 50 mg/L. In one embodiment, the method of the present invention reduces LDL levels below 100 mg/L, 90 mg/L, 80 mg/L, 70 mg/L, 60 mg/L, or 50 mg/L. In one embodiment, the method of the present invention reduces LDL levels below 70 mg/L, 60 mg/L, or 50 mg/L.

In one embodiment, the lipid is triglyceride. In one embodiment, the method of the present invention reduces triglyceride levels by at least 10%, 20%, 30%, 40%, 50%, 60%, 70%, 80%, or 90%, as compared to a control subject (e.g., a subject not administered with the composition of the present invention). In one embodiment, the subject has elevated levels of triglyceride, as compared to a healthy subject (e.g., an individual without a disease or condition, such as those described herein). In one embodiment, the method of the present invention reduces triglyceride levels below 800 mg/L, 700 mg/L, 600 mg/L, 500 mg/L, 400 mg/L, 300 mg/L, 200 mg/L, 190 mg/L, 180 mg/L, 170 mg/L, 160 mg/L, 150 mg/L, 140 mg/L, 130 mg/L, 120 mg/L, 110 mg/L, or 100 mg/L. In one embodiment, the method of the present invention reduces triglyceride levels below 200 mg/L, 190 mg/L, 180 mg/L, 170 mg/L, 160 mg/L, 150 mg/L, 140 mg/L, 130 mg/L, 120 mg/L, 110 mg/L, or 100 mg/L. In one embodiment, the method of the present invention reduces triglyceride levels below 150 mg/L, 140 mg/L, 130 mg/L, 120 mg/L, 110 mg/L, or 100 mg/L.

The present invention also provides a method for reducing the amount of bilirubin, and/or one or more liver enzymes, comprising administering a therapeutically effective amount of a pharmaceutical composition of the present invention to a subject in need thereof.

In one embodiment, the method of the present application reduces the amount of bilirubin by at least 10%, 20%, 30%, 40%, 50%, 60%, 70%, 80%, or 90%, as compared to a control subject (e.g., a subject not administered with the composition of the present invention). In one embodiment, the subject has an elevated level of bilirubin, as compared to a healthy subject (e.g., an individual without a disease or condition, such as those described herein). In one embodiment, the method of the present application reduces the level of bilirubin to a normal level (e.g., similar to the level of bilirubin in an individual without a disease or condition, such as those described herein). In a further embodiment, the method of the present application reduces the level of bilirubin below 10 mg/L, 9 mg/L, 8 mg/L, 7 mg/L, 6 mg/L, 5 mg/L, 4 mg/L, 3 mg/L, 2 mg/L, 1.5 mg/L, 1.2 mg/L, or 1 mg/L. In a further embodiment, the method of the present application reduces the level of bilirubin below 2 mg/L, 1.5 mg/L, 1.2 mg/L, or 1 mg/L.

In one embodiment, the liver enzyme is selected from the group consisting of alkaline phosphatase (ALP, AP, or Alk Phos), alanine aminotransferase (ALT), aspartate aminotransferase (AST), gamma-glutamyl transpeptidase (GGT), lactate dehydrogenase (LDH), and 5' nucleotidase. In one embodiment, the method of the present application reduces the amount of one or more liver enzymes by at least 10%, 20%, 30%, 40%, 50%, 60%, 70%, 80%, or 90%, as compared to a control subject (e.g., a subject not administered with the composition of the present invention). In one embodiment, the subject has elevated levels of one or more liver enzymes, as compared to a healthy subject (e.g., an individual without a disease or condition, such as those described herein). In one embodiment, the method of the present application reduces the levels of one or more liver enzymes (e.g., ALP, ALT, AST, GGT, LDH, and 5' nucleotidase) to normal levels (e.g., similar to the levels of liver enzymes in an individual without a disease or condition, such as those described herein).

In a further embodiment, the method of the present application reduces the level of ALP below 500 IU/L (international units per liter), 400 IU/L, 300 IU/L, 200 IU/L, 180 IU/L, 160 IU/L, or 150 IU/L. In a further embodiment, the method of the present application reduces the level of ALP to from about 40 IU/L to about 150 IU/L.

In a further embodiment, the method of the present application reduces the level of ALT below 200 IU/L (international units per liter), 150 IU/L, 100 IU/L, 80 IU/L, 60 IU/L, or 50 IU/L. In a further embodiment, the method of the present application reduces the level of ALT to from about 5 IU/L to about 50 IU/L.

In a further embodiment, the method of the present application reduces the level of AST below 200 IU/L (international units per liter), 150 IU/L, 100 IU/L, 80 IU/L, 60 IU/L, 50 IU/L, or 40 IU/L. In a further embodiment, the method of the present application reduces the level of AST to from about 10 IU/L to about 50 IU/L.

In a further embodiment, the method of the present application reduces the level of GGT below 200 IU/L (international units per liter), 150 IU/L, 100 IU/L, 90 IU/L, 80 IU/L, 70 IU/L, or 60 IU/L. In a further embodiment, the method of the present application reduces the level of GGT to from about 15 IU/L to about 50 IU/L or from about 5 IU/L to about 30 IU/L.

In a further embodiment, the method of the present application reduces the level of LDH below 500 IU/L (international units per liter), 400 IU/L, 300 IU/L, 200 IU/L, 180 IU/L, 160 IU/L, 150 IU/L, 140 IU/L, or 130 IU/L. In a further embodiment, the method of the present application reduces the level of LDH to from about 120 IU/L to about 220 IU/L.

In a further embodiment, the method of the present application reduces the level of 5' nucleotidase below 50 IU/L (international units per liter), 40 IU/L, 30 IU/L, 20 IU/L, 18 IU/L, 17 IU/L, 16 IU/L, 15 IU/L, 14 IU/L, 13 IU/L, 12 IU/L, 11 IU/L, 10 IU/L, 9 IU/L, 8 IU/L, 7 IU/L, 6 IU/L, or 5 IU/L. In a further embodiment, the method of the present application reduces the level of 5' nucleotidase to from about 2 IU/L to about 15 IU/L.

In one embodiment, the methods of the present invention comprise administering to a subject in need thereof an effective amount of a first compound that is an FXR agonist, in combination with at least one PPAR-alpha agonist, PPAR-delta agonist, and/or PPAR-alpha and delta dual agonist, and optionally one or more pharmaceutically acceptable carriers. In a further embodiment, the method comprises administering to a subject in need thereof an effective amount of a first compound, in combination with at least one PPAR-alpha agonist, PPAR-delta agonist, and/or PPAR-alpha and delta dual agonist, in which the first compound is a compound described herein (e.g., a compound of formula A, I, IA, II, or IIA, or Compound 1, 2, 3, or 4) or a pharmaceutically acceptable salt or amino acid conjugate thereof.

In one embodiment, the methods of the present invention comprise administering to a subject in need thereof an effective amount of a first compound that is an FXR agonist, in combination with at least one fibrate, and optionally one or more pharmaceutically acceptable carriers. In a further embodiment, the method comprises administering to a subject in need thereof an effective amount of a first compound, in combination with at least one fibrate, in which the first compound is a compound described herein (e.g., a compound of formula A, I, IA, II, or IIA, or Compound 1, 2, 3, or 4) or a pharmaceutically acceptable salt or amino acid conjugate thereof.

In one embodiment, the methods of the present invention comprise administering to a subject in need thereof an effective amount of a first compound that is an FXR agonist, in combination with at least one statin, and optionally one or more pharmaceutically acceptable carriers. In a further embodiment, the method comprises administering to a subject in need thereof an effective amount of a first compound, in combination with at least one statin, in which the first compound is a compound described herein (e.g., a compound of formula A, I, IA, II, or IIA, or Compound 1, 2, 3, or 4) or a pharmaceutically acceptable salt or amino acid conjugate thereof.

In one embodiment, the methods of the present invention comprise administering to a subject in need thereof an effective amount of a first compound that is an FXR agonist, in combination with at least one PPAR-alpha agonist, PPAR-delta agonist, and/or PPAR-alpha and delta dual agonist, at least one statin, and optionally one or more pharmaceutically acceptable carriers. In a further embodiment, the method comprises administering to a subject in need thereof an effective amount of a first compound, in combination with at least one PPAR-alpha agonist, PPAR-delta agonist, and/or PPAR-alpha and delta dual agonist, at least one statin, in which the first compound is a compound described herein (e.g., a compound of formula A, I, IA, II, or IIA, or Compound 1, 2, 3, or 4) or a pharmaceutically acceptable salt or amino acid conjugate thereof.

In one embodiment, the methods of the present invention comprise administering to a subject in need thereof an effective amount of a first compound that is an FXR agonist, in combination with at least one fibrate, at least one statin, and optionally one or more pharmaceutically acceptable carriers. In a further embodiment, the method comprises administering to a subject in need thereof an effective amount of a first compound, in combination with at least one fibrate, at least one statin, in which the first compound is a compound described herein (e.g., a compound of formula A, I, IA, II, or IIA, or Compound 1, 2, 3, or 4) or a pharmaceutically acceptable salt or amino acid conjugate thereof.

In one embodiment, the subject is a mammal. In one embodiment, the mammal is human.

In one embodiment, the first compound and PPAR-alpha agonist(s), PPAR-delta agonist(s), PPAR-alpha and delta or PPAR-alpha and gamma dual agonist(s), fibrate(s), or statin(s) are administered in a two-way combination, i.e., without any therapeutic agent other than the first compound and PPAR-alpha agonist(s), PPAR-delta agonist(s), PPAR-alpha and delta or PPAR-alpha and gamma dual agonist(s), fibrate(s), or statin(s). In a further embodiment, the first compound and fibrate(s) are administered in a two-way combination, i.e., without any therapeutic agent other than the first compound and fibrate(s). In another embodiment, the first compound and statin(s) are administered in a two-way combination, i.e., without any therapeutic agent other than the first compound and statin(s).

In another embodiment, the first compound and the PPAR-alpha agonist(s), PPAR-delta agonist(s), PPAR-alpha and delta or PPAR-alpha and gamma dual agonist(s), or fibrate(s) are administered in a three-way combination with a statin. In a further embodiment, the first compound and fibrate(s) are administered in a three-way combination with a statin.

The first compound, together with PPAR-alpha agonist(s), PPAR-delta agonist(s), PPAR-alpha and delta or PPAR-alpha and gamma dual agonist(s), or fibrate(s), and/or statin(s) can achieve profound synergistic effects, such as synergistic reductions in severe, combined hyperlipidemic states and those resistant to individual therapies and in the levels of one or more liver enzymes. Hence, for the very difficult to control hyperlipidemias, a combination of the first compound, a PPAR-alpha agonist, a PPAR-delta agonist, a PPAR-alpha and delta or PPAR-alpha and gamma dual agonist, or a fibrate, and/or a statin is advantageous. It can be particularly advantageous for such a combination of the first compound, a fibrate, and/or a statin to be provided in a single pharmaceutical composition with a pharmaceutical acceptable carrier (such as in a single capsule form) designed to increase compliance and hence effectiveness. Accordingly, the invention further provides a pharmaceutical composition comprising an effective amount of the first compound, an effective amount of at least one PPAR-alpha agonist, PPAR-delta agonist, or PPAR-alpha and delta or PPAR-alpha and gamma dual agonist, and an effective amount of at least one statin, together with one or more pharmaceutically acceptable carriers, diluents, adjuvants or excipients. In one embodiment, the invention further provides a pharmaceutical composition comprising an effective amount of the first compound, an effective amount of at least one fibrate, and an effective amount of at least one statin, together with one or more pharmaceutically acceptable carriers, diluents, adjuvants or excipients.

In one embodiment, the first compound and PPAR-alpha agonist(s), PPAR-delta agonist(s), PPAR-alpha and delta or PPAR-alpha and gamma dual agonist(s), or fibrate(s) are administered concurrently. For example, the first compound and PPAR-alpha agonist(s), PPAR-delta agonist(s), PPAR-alpha and delta or PPAR-alpha and gamma dual agonist(s), or fibrate(s) are administered together in a single pharmaceutical composition with a pharmaceutical acceptable carrier. In another embodiment, the first compound and PPAR-alpha agonist(s), PPAR-delta agonist(s), PPAR-alpha and delta or PPAR-alpha and gamma dual agonist(s), or fibrate(s) are administered sequentially. For example, the first compound is administered prior or subsequent to PPAR-alpha agonist(s), PPAR-delta agonist(s), PPAR-alpha and delta or PPAR-alpha and gamma dual agonist(s), or fibrate(s).

In one embodiment, the first compound and the statin are administered concurrently. For example, the first compound and the statin are administered together in a single pharmaceutical composition with a pharmaceutical acceptable carrier. In another embodiment, the first compound and the statin are administered sequentially. For example, the first compound is administered prior or subsequent to the statin.

In one embodiment, the first compound is administered at a first dose for a first time period, followed by administration of the first compound at a second dose for a second time period. In one embodiment, a first compound or a pharmaceutically acceptable salt or amino acid conjugate thereof is administered in a daily total amount from 0.1-1500 mg, 0.2-1200 mg, 0.3-1000 mg, 0.4-800 mg, 0.5-600 mg, 0.6-500 mg, 0.7-400 mg, 0.8-300 mg, 1-200 mg, 1-100 mg, 1-50 mg, 1-30 mg, 4-26 mg, or 5-25 mg for a first time period, followed by administration of the first compound in a daily total amount from 0.1-1500 mg, 0.2-1200 mg, 0.3-1000 mg, 0.4-800 mg, 0.5-600 mg, 0.6-500 mg, 0.7-400 mg, 0.8-300 mg, 1-200 mg, 1-100 mg, 1-50 mg, 1-30 mg, 4-26 mg, or 5-25 mg. In one embodiment, the total amount is orally administered once a day. In one embodiment, the first dose is different from the second dose. In a further embodiment, the first dose is lower than the second dose. In another embodiment, the first dose is higher than the second dose. In one embodiment, the first dose is about 5 mg (e.g., from 4.8 mg to 5.2 mg), and the second dose is about 10 mg (e.g., from 9.8 mg to 10.2 mg). In one embodiment, the first time period is about 6 months. In one embodiment, the second time period is about 6 months.

In one embodiment, the pharmaceutical composition is administered orally, parenterally, or topically. In another embodiment, the pharmaceutical composition is administered orally.

A composition in accordance with the present invention will typically contain sufficient first compound or a pharmaceutically acceptable salt or amino acid conjugate thereof, PPAR-alpha agonist(s), PPAR-delta agonist(s), PPAR-alpha and delta or PPAR-alpha and gamma dual agonist(s), or fibrate(s), and/or statin(s) to permit the desired daily dose of each to be administered to a subject in need thereof in a single unit dosage form, such as a tablet or capsule, or in two or more unit dosage forms to be administered simultaneously or at intervals during a day.

The invention also provides a pharmaceutical composition wherein the first compound and PPAR-alpha agonist(s), PPAR-delta agonist(s), PPAR-alpha and delta or PPAR-alpha and gamma dual agonist(s), or fibrate(s) are administered in combination with UDCA. In one aspect, UDCA is administered in a three-way combination. In another aspect, the two-way combination of a first compound and PPAR-alpha agonist(s), PPAR-delta agonist(s), PPAR-alpha and delta or
PPAR-alpha and gamma dual agonist(s), or fibrate(s) is administered for the treatment or prevention of a disease or condition, in place of UDCA to a subject who has an inadequate therapeutic response to UDCA alone.

In the methods of the present invention the active substances may be administered in single daily doses, or in two, three, four or more identical or different divided doses per day, and they may be administered simultaneously or at different times during the day. Usually, the active substances will be administered simultaneously, more usually in a single combined dosage form.

In one aspect, the first compound, PPAR-alpha agonist(s), PPAR-delta agonist(s), PPAR-alpha and delta or PPAR-alpha and gamma dual agonist(s), or fibrate(s), and/or statin(s) are administered at dosages substantially the same as the dosages at which they are administered in the respective monotherapies. In one aspect, the first compound is administered at a dosage which is less than (e.g., less than 90%, less than 80%, less than 70%, less than 60%, less than 50%, less than 40%, less than 30%, less than 20%, or less than 10%) its monotherapy dosage. In one aspect, the PPAR-alpha agonist(s), PPAR-delta agonist(s), PPAR-alpha and delta or PPAR-alpha and gamma dual agonist(s), or fibrate(s) is administered at a dosage which is less than (e.g., less than 90%, less than 80%, less than 70%, less than 60%, less than 50%, less than 40%, less than 30%, less than 20%, or less than 10%) its monotherapy dosage. In one aspect, both the first compound and PPAR-alpha agonist(s), PPAR-delta agonist(s), PPAR-alpha and delta or PPAR-alpha and gamma dual agonist(s), or fibrate(s) are administered at a dosage which is less than (e.g., less than 90%, less than 80%, less than 70%, less than 60%, less than 50%, less than 40%, less than 30%, less than 20%, or less than 10%) their respective monotherapy dosages. In one aspect, the statin(s) is administered at a dosage which is less than (e.g., less than 90%, less than 80%, less than 70%, less than 60%, less than 50%, less than 40%, less than 30%, less than 20%, or less than 10%) its monotherapy dosage. In one aspect, both the first compound and statin(s) are administered at a dosage which is less than (e.g., less than 90%, less than 80%, less than 70%, less than 60%, less than 50%, less than 40%, less than 30%, less than 20%, or less than 10%) their respective monotherapy dosages. In one aspect, the first compound, PPAR-alpha agonist(s), PPAR-delta agonist(s), PPAR-alpha and delta or PPAR-alpha and gamma dual agonist(s), or fibrate(s), and/or statin(s) are administered at a dosage which is less than (e.g., less than 90%, less than 80%, less than 70%, less than 60%, less than 50%, less than 40%, less than 30%, less than 20%, or less than 10%) their respective monotherapy dosages.

A pharmaceutical composition of the present invention may be in any convenient form for oral administration, such as a tablet, capsule, powder, lozenge, pill, troche, elixir, lyophilized powder, solution, granule, suspension, emulsion, syrup or tincture. Slow-release, modified release, or delayed-release forms may also be prepared, for example in the form of coated particles, multi-layer tablets, capsules within capsules, tablets within capsules, or microgranules.

Solid forms for oral administration may contain pharmaceutically acceptable binders, sweeteners, disintegrating agents, diluents, flavoring agents, coating agents, preservatives, lubricants and/or time delay agents. Suitable binders include gum acacia, gelatin, corn starch, gum tragacanth, sodium alginate, carboxymethylellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange or raspberry flavoring. Suitable coating agents include polymers or copolymers or acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulfite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further include dispersing agents and/or suspending agents. Suitable suspending agents include sodium carboxymethylcellulose, methylcellulose, hydroxypropyl methylcellulose, polyvinylpyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further include one or more emulsifying agents. Suitable emulsifying agents include dispersing agents as exemplified above or natural gums such as gum acacia or gum tragacanth.

Pharmaceutical compositions of the present invention may be prepared by blending, grinding, homogenizing, suspending, dissolving, emulsifying, dispersing and/or mixing the first compound or its pharmaceutically acceptable salt or amino acid conjugate and at least one lipid lowering agent, e.g., fibrate, and optionally the statin(s) together with the selected excipient(s), carrier(s), adjuvant(s) and/or diluent(s). One type of pharmaceutical composition of the present invention in the form of a tablet or capsule may be prepared by (a) preparing a first tablet comprising at least one of the active substances selected from the first compound or a pharmaceutically acceptable salt or amino acid conjugate thereof and at least one lipid lowering agent together with any desired excipient(s), carrier(s), adjuvant(s) and/or diluent(s), and (b) preparing a second tablet or a capsule, wherein the second tablet or the capsule includes the remaining active substance(s) and the first tablet. Another type of pharmaceutical composition of the present invention in the form of a capsule may be prepared by (a) preparing a first capsule comprising at least one of the active substances selected from the first compound or a pharmaceutically acceptable salt or amino acid conjugate thereof and the lipid lowering agent(s), together with any desired excipient(s), carrier(s), adjuvant(s) and/or diluent(s), and (b) preparing a second capsule, wherein the second capsule includes the remaining active substance(s) and the first capsule. A further type of pharmaceutical composition of the present invention in the form of a tablet may be prepared by (a) preparing a capsule comprising at least one of the active substances selected from a first compound or a pharmaceutically acceptable salt or amino acid conjugate thereof and at least one lipid lowering agent, together with any desired excipient(s), carrier(s), adjuvant(s) and/or diluent(s), and (b) preparing a tablet, wherein the tablet includes the remaining active substance(s) and the capsule.

In embodiments, the PPAR-alpha agonist(s), PPAR-delta agonist(s), PPAR-alpha and delta or PPAR-alpha and gamma dual agonist(s), or fibrate(s), and/or statin(s) is used either as an immediate release tablet or as a sustained release tablet. It is particularly effective when provided in a sustained release tablet. Sustained release tablets of various lipid lowering agents are commercially available. It is preferable for prolonged action that the tablet is in a sustained release format.

In another embodiment, the pharmaceutical composition of the present invention comprises a capsule containing a PPAR-alpha agonist(s), PPAR-delta agonist(s), PPAR-alpha and delta or PPAR-alpha and gamma dual agonist(s), or fibrate(s), and/or statin(s) within a capsule containing a first compound or a pharmaceutically acceptable salt or amino acid conjugate thereof. Typically in this form the PPAR-alpha agonist(s), PPAR-delta agonist(s), PPAR-alpha and delta or PPAR-alpha and gamma dual agonist(s), or fibrate(s), and/or statin(s) is presented in an immediate release form. In that event it is usual to administer the composition three times daily. Another mode of administration is to provide a composition containing the PPAR-alpha agonist(s), PPAR-delta agonist(s), PPAR-alpha and delta or PPAR-alpha and gamma dual agonist(s), or fibrate(s), and/or statin(s) in either a sustained release or a non-sustained release form as described above, twice daily, wherein the daily amount of the composition administered contains sufficient amount of the active substances to provide the desired daily dosage to the patient.

In one embodiment, the pharmaceutical compositions of the invention is a dosage form which comprises a first compound or a pharmaceutically acceptable salt or amino acid conjugate thereof in a daily total amount of from 0.1-1500 mg, 0.2-1200 mg, 0.3-1000 mg, 0.4-800 mg, 0.5-600 mg, 0.6-500 mg, 0.7-400 mg, 0.8-300 mg, 1-200 mg, 1-100 mg, 1-50 mg, 1-30 mg, 4-26 mg, or 5-25 mg. In one embodiment, the total amount is orally administered once a day.

In one embodiment, the pharmaceutical compositions of the invention is a dosage form which comprises a PPAR-alpha agonist, PPAR-delta agonist, PPAR-alpha and delta or PPAR-alpha and gamma dual agonist, or fibrate, and/or statin in a daily total amount of 10-1000 mg, 20-800 mg, 50-500 mg, 80-400 mg, or 100-300 mg, more typically about 200 mg. In one embodiment, the total amount is orally administered once a day. In one embodiment, the pharmaceutical compositions of the invention is a dosage form which comprises a statin in an amount of 5-1000 mg, 10-800 mg, 20-500 mg, 30-400 mg, or 40-200 mg.

In embodiments, the compositions of the invention is a dosage form which comprises a PPAR-alpha agonist, PPAR-delta agonist, PPAR-alpha and delta or PPAR-alpha and gamma dual agonist, or fibrate, and/or statin in an amount of 10-1000 mg, 20-800 mg, 50-500 mg, 80-400 mg, or 100-300 mg, more typically about 200 mg, contained within a capsule which contains the first compound in an amount of from 0.1-1500 mg, 0.2-1200 mg, 0.3-1000 mg, 0.4-800 mg, 0.5-600 mg, 0.6-500 mg, 0.7-400 mg, 0.8-300 mg, 1-200 mg, 1-100 mg, 1-50 mg, 1-30 mg, 4-26 mg, or 5-25 mg. In one embodiment, the PPAR-alpha agonist, PPAR-delta agonist, PPAR-alpha and delta or PPAR-alpha and gamma dual agonist, or fibrate, and/or statin is in the sustained release form.

In embodiments, the compositions of the invention is a dosage form which comprises a sustained release tablet of bezafibrate, in an amount of 10-1000 mg, 20-800 mg, 50-500 mg, 80-400 mg, or 100-300 mg, more typically about 200 mg, contained within a capsule which contains the first compound in an amount of from 0.1-1500 mg, 0.2-1200 mg, 0.3-1000 mg, 0.4-800 mg, 0.5-600 mg, 0.6-500 mg, 0.7-400 mg, 0.8-300 mg, 1-200 mg, 1-100 mg, 1-50 mg, 1-30 mg, 4-26 mg, or 5-25 mg. In this way the patient to whom the dosage form is administered receives a sustained release tablet of bezafibrate which is delivered to the distal antrum as the capsule breaks open and releases the first compound.

The pharmaceutical composition of the present invention can be used lifelong by the patient, prolonging survival and delaying liver transplantation. The reduction of hyperlipidemia and liver enzymes ensures reduction in the development of associated vascular disease. Both the first compound and lipid lowering agents, such as fibrates and/or statins have very minimal long-term side effect profile (with some exceptions for bezafibrate) and therefore this combination is likely to be the therapy of choice for primary biliary cirrhosis (PBC) with hyperlipidemia and for resistant primary biliary cirrhosis (PBC). Because of the simplified dosing provided by the present invention, a combined therapy of the present invention can be used in increasing doses, depending on a patient's weight and clinical response.

A composition of the present invention that comprises a first compound or a pharmaceutically acceptable salt or amino acid conjugate thereof, a PPAR-alpha agonist, PPAR-delta agonist, PPAR-alpha and delta or PPAR-alpha and gamma dual agonist, or fibrate, and/or a statin can be provided as the three active substances within a single capsule. In one form of such a composition, a statin may be mixed with a first compound in an inner capsule, the inner capsule being surrounded by a PPAR-alpha agonist, PPAR-delta agonist, PPAR-alpha and delta or PPAR-alpha and gamma dual agonist, or fibrate contained within an outer capsule. The locations within the capsules may be reversed. That is, the mixture of a statin and a first compound may be contained within the outer capsule and the PPAR-alpha agonist, PPAR-delta agonist, PPAR-alpha and delta or PPAR-alpha and gamma dual agonist, or fibrate may be contained within the inner capsule. This arrangement will be especially desirable if the quantity of the statin to be administered is relatively large. Other combinations for administration of the combination of three active substances are possible.

The first compounds disclosed herein can be prepared by the conventional methods (e.g., those described in U.S. Publication No. 2009/0062526, U.S. Pat. No. 7,138,390, and WO 2006/122977), such as by a 6-step synthesis followed by one purification step to produce highly pure Compound 1 (obeticholic acid, or OCA) as shown in Scheme 1 below.

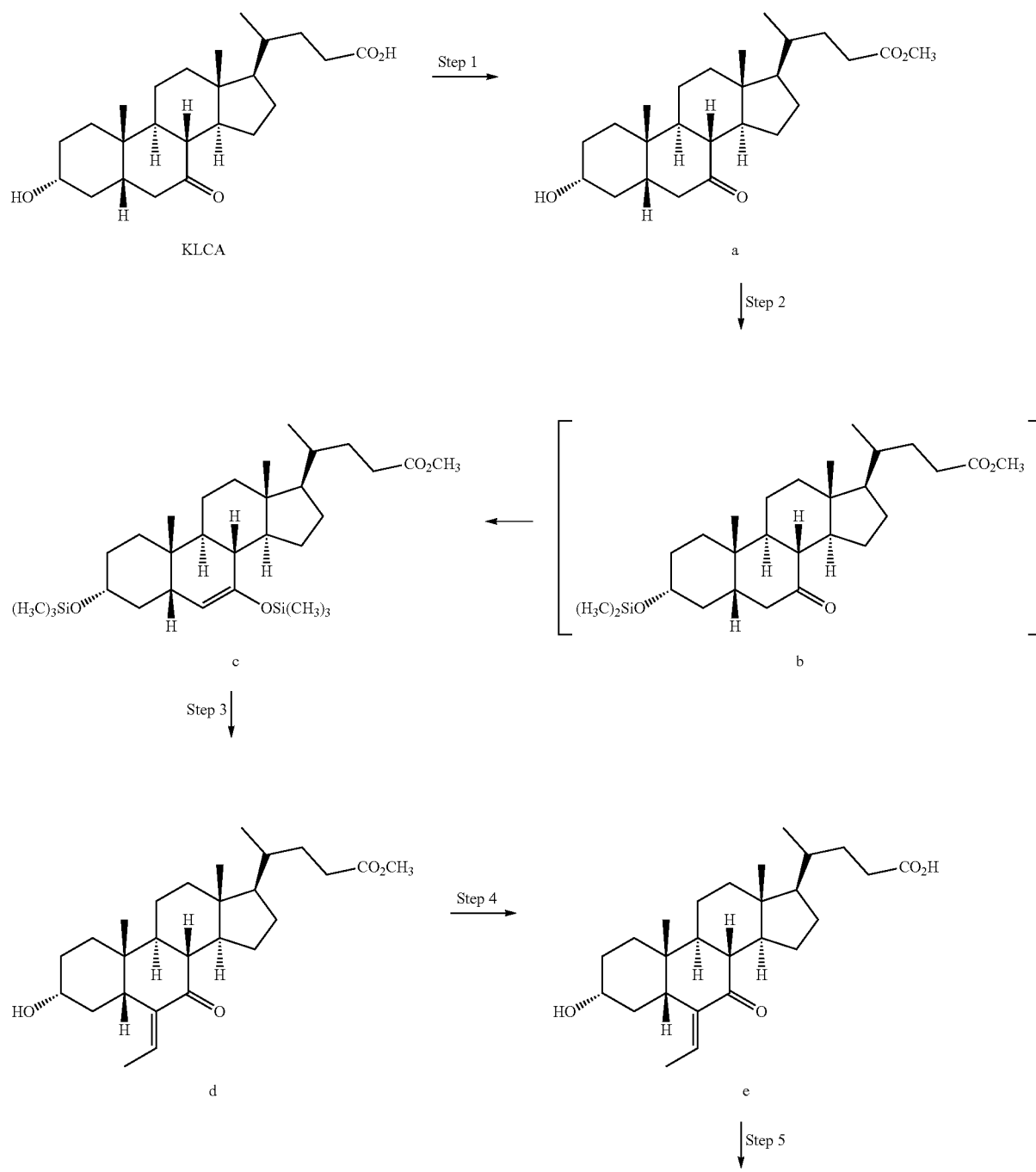

25

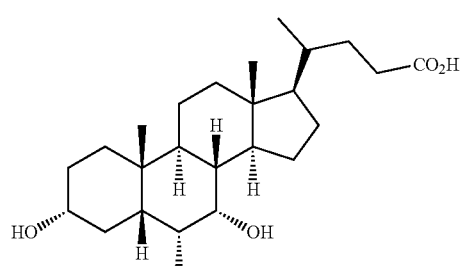

crystalline OCA (e.g., Form C)

Step 6 ←

26

-continued

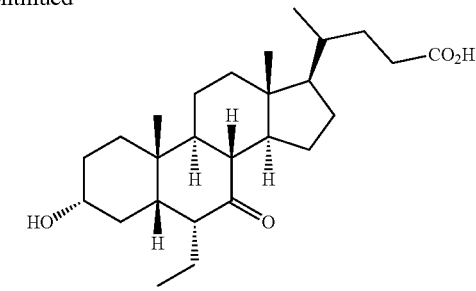

f

Step 7 ↓

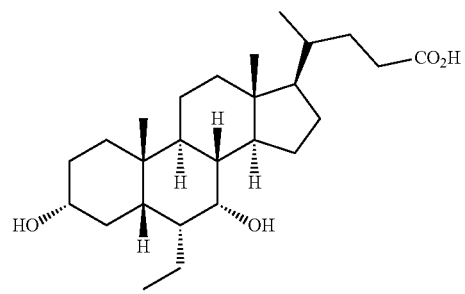

OCA Form 1

The process above was described in WO 2013/192097, the contents of which are incorporated herein by reference in their entirety. The process is a 6-step synthesis followed by one purification step. Step 1 is the esterification of the C-24 carboxylic acid of 7-keto lithocholic acid (KLCA) to produce the methyl ester compound a. Step 2 is silylenol ether formation from compound 1 to produce compound c. Step 3 is an aldol condensation reaction of the silylenol ether compound c and acetaldehyde to produce compound d. Step 4 is saponification of compound d to produce compound e. Step 5 is the hydrogenation of compound e to produce compound f. Step 6 is the selective reduction of the 7-keto group of compound f to produce crystalline Compound 1. Step 7 is the conversion of crystalline compound to amorphous Compound 1 (obeticholic acid Form 1, or OCA Form 1).

Alternatively, the first compound disclosed herein can be prepared by the conventional methods (e.g., those described in U.S. Pat. No. 7,932,244), or via a process as shown in Scheme 2 (and disclosed WO 2014/066819). Scheme 2 can be used to prepare Compound 2, 3, or 4 disclosed herein.

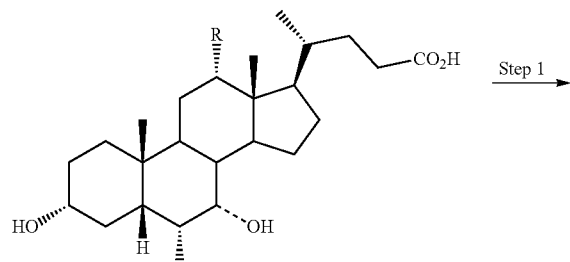

II

Step 1 →

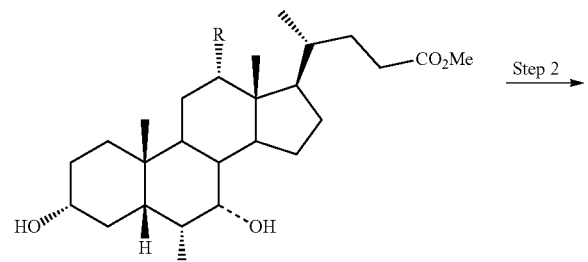

III

Step 2 →

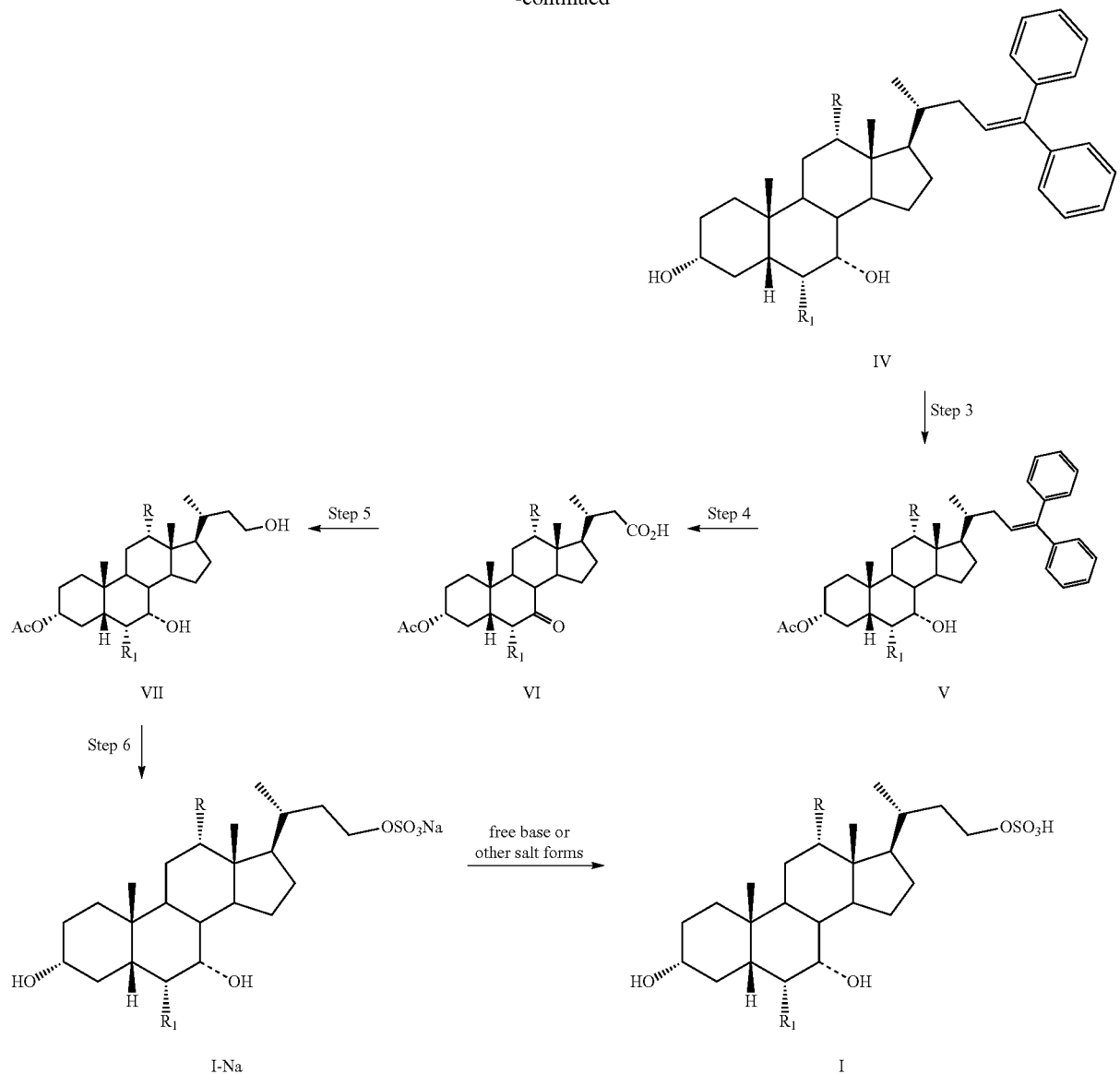

Step 1 is the esterification of a compound of formula II to obtain a compound of formula III. Step 2 is a reaction to form a compound of formula IV from a compound of formula III. Step 3 is the protection of the hydroxy group at the C3 position of a compound of formula IV to afford a compound of formula V. Step 4 is the oxidative cleavage of compound of formula V to give a compound of formula VI. Step 5 is the reduction of a compound of formula VI to afford a compound of formula VII. Step 6 is the sulfonation of a compound of formula VII to give a salt of formula I-Na. A salt of formula I-Na can be converted to its free base form (i.e., a compound of formula I) or other salt forms (e.g., a salt of formula I-(Et)$_3$NH).

Definitions

For convenience, certain terms used in the specification, examples and appended claims are collected here.

As used herein the term "fibrate" means any of fibric acid derivatives and pharmaceutically active derivatives of 2-phenoxy-2-methylpropanoic acid useful in the methods described herein. Examples of fibrates include, but are not limited to, fenofibrate, bezafibrate, beclobrate, binifibrate, ciprofibrate, clinofibrate, clofibrate, clofibric acid, etofibrate, gemfibrozil, nicofibrate, pirifibrate, ronifibrate, simfibrate, theofibrate, tocofibrate, plafibride, etc. Examples of fibrates are also described in U.S. Pat. Nos. 3,781,328, 3,948,973, 3,869,477, 3,716,583, 3,262,580, 3,723,446, 4,058,552, 3,674,836, 3,369,025, 3,984,413, 3,971,798, 6,384,062, 7,119,198 and 7,259,186; U.S. Pub. No. 20090131395; WO2008/039829; Belgian patent no. 884722; United Kingdom patent no. 860303; and European patent application publication no. EP0607536, the entire disclosures of each of which are incorporated herein by reference.

Peroxisome proliferator-activated receptor alpha (PPAR-alpha), also known as NR1C1 (nuclear receptor subfamily 1, group C, member 1), is a nuclear receptor protein. A PPAR-alpha agonist binds to and activates PPAR-alpha. Examples of a PPAR-alpha agonist include, but are not limited to, a fibrate, such as the fibrates described herein.

Peroxisome proliferator-activated receptor delta (PPAR-delta), also known as NR1C2 (nuclear receptor subfamily 1, group C, member 2), is a nuclear receptor protein. A PPAR-delta agonist binds to and activates PPAR-delta. Examples of a PPAR-delta agonist include, but are not limited to, {4-[({4-methyl-2-[4-(trifluoromethyl)phenyl]-1,3-thiazol-5-yl}methyl)sulfanyl]-2-methylphenoxy}acetic acid (also known in the art as GW501516, GW1516, and Endurabol), {2-methyl-4-[5-methyl-2-(4-trifluoromethyl-phenyl)-2H-[1,2,3]triazol-4-ylmethylsylfanyl]-phenoxy}-acetic acid, and [4-[[[2-[3-fluoro-4-(trifluoromethyl)phenyl]-4-methyl-5-thiazolyl]methyl]thio]-2-methyl phenoxy]-acetic acid.

A PPAR-alpha and delta or PPAR-alpha and gamma dual agonist binds to and activates both PPAR-alpha and PPAR-delta, or both PPAR-alpha and PPAR-gamma. Examples of PPAR-alpha and delta dual agonist include, but are not limited to, 2-[2,6 dimethyl-4-[3-[4-(methylthio)phenyl]-3-oxo-1(E)-propenyl]phenoxyl]-2-methylpropanoic acid (also known as GFT505). Examples of PPAR alpha and gamma dual agonists include, but are not limited to, aleglitazar ((2S)-2-methoxy-3-[4-[2-(5-methyl-2-phenyl-4-oxazolyl)ethoxy]-7-benzothiophenyl]propanoic acid, CAS No. 475479-34-6), muraglitazar (N-[(4-methoxyphenoxy)carbonyl]-N-{4-[2-(5-methyl-2-phenyl-1,3-oxazol-4-yl)ethoxy]benzyl}glycine, CAS No. 331741-94-7), tesaglitazar ((2S)-2-ethoxy-3-[4-[2-(4-methylsulfonyloxyphenyl)ethoxy]phenyl]propanoic acid, CAS No. 251565-85-2) and saroglitazar ((2S)-2-ethoxy-3-[4-(2-{2-methyl-5-[4-(methylsulfanyl)phenyl]-1H-pyrrol-1-yl}ethoxy)phenyl]propanoic acid, CAS No. 495399-09-2).

As used herein, the term "FXR agonist" refers to any compound which activates FXR. In one aspect, an FXR agonist achieves at least 50% activation of FXR relative to CDCA, the appropriate positive control in the assay methods described in WO 2000/037077. In another aspect, an FXR agonist achieves 100% activation of FXR in the scintillation proximity assay or the HTRF assay as described in WO2000/037077. Examples of FXR agonists include but are not limited to those described in U.S. Pat. Nos. 7,138,390; 7,932,244; 20120283234; 20120232116; 20120053163; 20110105475; 20100210660; 20100184809; 20100172870; 20100152166; 20100069367; 20100063018; 20100022498; 20090270460; 20090215748; 20090163474; 20090093524; 20080300235; 20080299118; 20080182832; 20080039435; 20070142340; 20060069070; 20050080064; 20040176426; 20030130296; 20030109467; 20030003520; 20020132223; and 20020120137.

As used herein, the term "obeticholic acid" or "OCA" refers to a compound having the chemical structure:

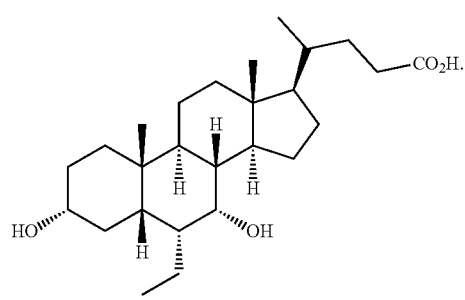

Obeticholic acid is also referred to as obeticholic acid Form 1, INT-747, 3α,7α-dihydroxy-6α-ethyl-5β-cholan-24-oic acid, 6α-ethyl-chenodeoxycholic acid, 6-ethyl-CDCA, 6ECDCA, cholan-24-oic acid, 6-ethyl-3,7-dihydroxy-(3α, 5β, 6α,7α), and can be prepared by the methods described in U.S. Publication No. 2009/0062526 A1, U.S. Pat. No. 7,138,390, and WO2006/122977. The CAS registry number for obeticholic acid is 459789-99-2.

As used herein, the term "crystalline obeticholic acid" refers to any crystalline form of a compound having the chemical structure:

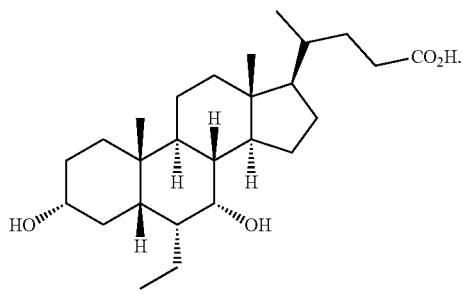

Crystalline obeticholic acid means that the compound is crystallized into a specific crystal packing arrangement in three spatial dimensions or the compound having external face planes. The crystalline form of obeticholic acid (or a pharmaceutically acceptable salt thereof) can crystallize into different crystal packing arrangements, all of which have the same elemental composition of obeticholic acid. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystals of obeticholic acid can be prepared by crystallization under different conditions, e.g., different solvents, temperatures, etc. Examples of crystalline forms of OCA are described in U.S. Pat. No. 9,238,673.

The term "first compound" means a compound of formula A, I, IA, II, or IIA, or Compound 1, 2, 3, or 4, or a pharmaceutically acceptable salt or amino acid conjugate thereof. Whenever the term is used in the context of the present invention it is to be understood that the reference is being made to the free base, an isotopically-labeled compound, a crystalline compound, or a corresponding pharmaceutically acceptable salt or amino acid conjugates thereof, provided that such is possible and/or appropriate under the circumstances.

As used herein, the term "amino acid conjugates" refers to conjugates of a first compound of the present invention (e.g., a compound of Formula A) with any suitable amino acid. For example, such a suitable amino acid conjugate of a compound of Formula A will have the added advantage of enhanced integrity in bile or intestinal fluids. Suitable amino acids include but are not limited to glycine and taurine. Thus, the present invention encompasses the glycine and taurine conjugates of a first compound of the present invention (e.g., Compound 1). The term "statin" is synonymous with the terms "3-hydroxy-3-methylglutaryl-Coenzyme A reductase inhibitor" and "HMG-CoA reductase inhibitor". These terms are used interchangeably herein. As the synonyms suggest, statins are inhibitors of 3-hydroxy-3-methylglutaryl-Coenzyme A reductase and, as such, are effective in lowering the level of blood plasma cholesterol and accordingly for treating or preventing cardiovascular diseases. Statins and pharmaceutically acceptable salts thereof are particularly useful in lowering low-density lipoprotein cholesterol (LDL-C) levels in mammals and particularly in humans. Structurally, statins or derivatives thereof have in common a 4-hydroxy-6-oxo-2H-pyran system, which may also be in the form of dihydroxy acid which interacts with the active site of HMG-CoA reductase, and a lipophilic part which presents in particular as a polysubstituted hexahydronaphthalenic system, but may also be replaced with a polysubstituted heteroaromatic system, as in atorvastatin or fluvastatin. The statin suitable for use herein include, but are not limited to, simvastatin, fluvastatin, pravastatin, rivastatin, mevastatin, atorvastatin, cerivastatin, lovastatin, pitavastatin, fluindostatin, velostatin, dalvastatin, rosuvastatin, dihydrocompactin, and compactin, or a pharmaceutically acceptable salt thereof.

The term "lipid lowering agent" refers to any agent that is capable of lowering the concentration of lipid (e.g., cholesterol, LDL, and triglyceride) in circulation (e.g., in the blood). A lipid lowering agent includes, but is not limited to, (i) a bile acid sequestrant, such as a resin (e.g., cholestyramine, colestipol, colesevelam), (ii) a cholesterol absorption inhibitor, which prevents uptake of cholesterol (e.g., from the small intestine into the circulatory system), such as ezetimibe (i.e., (3R,4S)-1-(4-fluorophenyl)-3-[(3S)-3-(4-fluorophenyl)-3-hydroxypropyl]-4-(4-hydroxyphenyl) azetidin-2-one) and (3R,4S)-1,4-bis(4-methoxyphenyl)-3-(3-phenylpropyl)-2-azetidinone, (iii) Omega-3 fatty acid ethyl esters, including free fatty acid derivatives (e.g., Omacor®, Lovaza®, Vascepa™, Epadel, Epanova™), or marine-derived omega-3 polyunsaturated fatty acids (PUFA), (iv) PCSK9 inhibitors, (v) nicotinic acid, (vi) phytosterols (e.g., plant sterols and stanols), such as β-sitosterol, campesterol, stigmasterol, brassicasterol, ergosterol, β-sitostanol, campestanol, stigmastanol, cycloartenol, and lupeol, (vii) inhibitors of CETP (cholesteryl ester transfer protein), such as Anacetrapib, Evacetrapib, Torcetrapib, and Dalcetrapib, (viii) squalene synthase inhibitors, (ix) antisense oligonucleotides which affect the synthesis, degredation, absorption, and metabolism of lipids (e.g., antisense oligonucleotides that binds to the mRNA that encodes apolipoprotein B or PCSK9) (e.g., Mipomersen (Kynamro)), (x) apoprotein-B inhibitors, (xi) inhibitors of microsomal triglyceride transport protein (e.g., Lomitapide (Juxtapid)), and (xii) other compounds, such as colesevelam, avasimibe, and implitapide.

"Treating", includes any effect, e.g., lessening, reducing, modulating, or eliminating, that results in the improvement of the condition, disease, disorder, etc. "Treating" or "treatment" of a disease state includes: inhibiting the disease state, i.e., arresting the development of the disease state or its clinical symptoms, or relieving the disease state, i.e., causing temporary or permanent regression of the disease state or its clinical symptoms.

"Preventing" the disease state includes causing the clinical symptoms of the disease state not to develop in a subject that may be exposed to or predisposed to the disease state, but does not yet experience or display symptoms of the disease state.

The term "inhibiting" or "inhibition," as used herein, refers to any detectable positive effect on the development or progression of a disease or condition. Such a positive effect may include the delay or prevention of the onset of at least one symptom or sign of the disease or condition, alleviation or reversal of the symptom(s) or sign(s), and slowing or prevention of the further worsening of the symptom(s) or sign(s).

"Disease state" means any disease, disorder, condition, symptom, or indication.

The term "effective amount" or "therapeutically effective amount" as used herein refers to an amount of a first compound (e.g., an FXR-activating ligand), or a fibrate, or a lipid lowering agent, or a statin that produces an acute or chronic therapeutic effect upon appropriate dose administration, alone or in combination. In one embodiment, an effective amount or therapeutically effective amount of a first compound (e.g., an FXR-activating ligand) produces an acute or chronic therapeutic effect upon appropriate dose administration in combination with at least one fibrate. The effect includes the prevention, correction, inhibition, or reversal of the symptoms, signs and underlying pathology of a disease/condition (e.g., fibrosis of the liver, kidney, or intestine) and related complications to any detectable extent. An "effective amount" or "therapeutically effective amount" will vary depending on the first compound, the fibrate, the lipid lowering agent, the statin, the disease and its severity, and the age, weight, etc., of the subject to be treated.

A therapeutically effective amount of a first compound can be formulated together with one or more fibrates, and optionally one or more pharmaceutically acceptable carriers for administration to a human or a non-human animal. Accordingly, the pharmaceutical composition of the invention can be administered, for example, via oral, parenteral, or topical routes, to provide an effective amount of the first compound and the fibrate(s). In alternative embodiments, the compositions of the invention can be used to coat or impregnate a medical device, e.g., a stent.

"Pharmacological effect" as used herein encompasses effects produced in the subject that achieve the intended purpose of a therapy. In one embodiment, a pharmacological effect means that primary indications of the subject being treated are prevented, alleviated, or reduced. For example, a pharmacological effect would be one that results in the prevention, alleviation or reduction of primary indications in a treated subject. In another embodiment, a pharmacological effect means that disorders or symptoms of the primary indications of the subject being treated are prevented, alleviated, or reduced. For example, a pharmacological effect would be one that results in the prevention, alleviation or reduction of the disorders or symptoms in a treated subject.

It is to be understood that the isomers arising from asymmetric carbon atoms (e.g., all enantiomers and diastereomers) are included within the scope of the invention, unless indicated otherwise. Such isomers can be obtained in substantially pure form by classical separation techniques and by stereochemically controlled synthesis.

A "pharmaceutical composition" is a formulation containing therapeutic agents such as a first compound and a lipid lowering agent, such as a fibrate, in a form suitable for administration to a subject. In one embodiment, the pharmaceutical composition is in bulk or in unit dosage form. It can be advantageous to formulate compositions in dosage unit form for ease of administration and uniformity of dosage. Dosage unit form as used herein refers to physically discrete units suited as unitary dosages for the subject to be treated; each unit containing a predetermined quantity of active reagent calculated to produce the desired therapeutic effect in association with the required pharmaceutical carrier. The specification for the dosage unit forms of the invention are dictated by and directly dependent on the unique characteristics of the active agents and the particular therapeutic effect to be achieved, and the limitations inherent in the art of compounding such an active agent for the treatment of individuals.

The term "unit dosage form" refers to physically discrete units suitable as unitary dosages for humans and other mammals, each unit containing a predetermined quantity of active material calculated to produce the desired therapeutic effect, in association with a suitable pharmaceutical excipient as described herein.

The unit dosage form is any of a variety of forms, including, for example, a capsule, an IV bag, a tablet, a single pump on an aerosol inhaler, or a vial. The quantity of first compound or a pharmaceutically acceptable salt or amino acid conjugate thereof in a unit dose of composition is an effective amount and is varied according to the particular treatment involved and/or the lipid lowering agent(s) used for the treatment. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the first compound and/or a lipid lowering agent is mixed under sterile conditions with a pharmaceutically acceptable carrier, and with any preservatives, buffers, or propellants that are required.

The term "flash dose" refers to formulations that are rapidly dispersing dosage forms.

The term "immediate release" is defined as a release of a therapeutic agent (such as a first compound or lipid lowering agent) from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a therapeutic agent from a dosage form over a prolonged period.

A "subject" includes mammals, e.g., humans, companion animals (e.g., dogs, cats, birds, and the like), farm animals (e.g., cows, sheep, pigs, horses, fowl, and the like), and laboratory animals (e.g., rats, mice, guinea pigs, birds, and the like). In one embodiment, the subject is human. In one aspect, the subject is female. In one aspect, the subject is male.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable carrier or excipient" means a carrier or excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

While it is possible to administer the first compound directly without any formulation, the first compound may be administered in the form of a pharmaceutical formulation comprising a pharmaceutically acceptable excipient. This formulation can be administered by a variety of routes including oral, buccal, rectal, intranasal, transdermal, subcutaneous, intravenous, intramuscular, and intranasal.

In one embodiment, the first compound can be administered transdermally. In order to administer transdermally, a transdermal delivery device ("patch") is needed. Such transdermal patches may be used to provide continuous or discontinuous infusion of a compound of the present invention in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

In one embodiment, the pharmaceutical composition of the present invention is adapted for buccal and/or sublingual, or nasal administration. This embodiment provides administration of the first compound in a manner that avoids gastric complications, such as first pass metabolism by the gastric system and/or through the liver. This administration route may also reduce adsorption times, providing more rapid onset of therapeutic benefits.

The first compound may be administered over a wide dosage range. For example, dosages per day normally fall within the range of about 0.0001 to about 30 mg/kg of body weight. In the treatment of adult humans, the range of about 0.1 to about 15 mg/kg/day, in single or divided dose, may be used. In one embodiment, the formulation comprises about 0.1 mg to about 1500 mg of a first compound. In another embodiment, the formulation comprises about 1 mg to about 100 mg of a first compound. In another embodiment, the formulation comprises about 1 mg to about 50 mg of a first compound. In another embodiment, the formulation comprises about 1 mg to about 30 mg of a first compound. In another embodiment, the formulation comprises about 4 mg to about 26 mg of a first compound. In another embodiment, the formulation comprises about 5 mg to about 25 mg of a first compound. However, it will be understood that the amount of the first compound actually administered will be determined by a physician, in the light of the relevant circumstances, including the condition to be treated, the chosen route of administration, the form of the first compound administered, the lipid lowering agent(s) administered, the age, weight, and response of the individual patient, and the severity of the patient's symptoms. Therefore, the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

As used herein, a "cholestatic condition" refers to any disease or condition in which bile excretion from the liver is impaired or blocked, which can occur either in the liver or in the bile ducts. Intrahepatic cholestasis and extrahepatic cholestasis are the two types of cholestatic conditions. Intrahepatic cholestasis (which occurs inside the liver) is most commonly seen in primary biliary cirrhosis, primary sclerosing cholangitis, sepsis (generalized infection), acute alcoholic hepatitis, drug toxicity, total parenteral nutrition (being fed intravenously), malignancy, cystic fibrosis, biliary atresia, and pregnancy. Extrahepatic cholestasis (which occurs outside the liver) can be caused by bile duct tumors, strictures, cysts, diverticula, stone formation in the common bile duct, pancreatitis, pancreatic tumor or pseudocyst, and compression due to a mass or tumor in a nearby organ.

Clinical symptoms and signs of a cholestatic condition include: itching (pruritus), fatigue, jaundiced skin or eyes, inability to digest certain foods, nausea, vomiting, pale stools, dark urine, and right upper quadrant abdominal pain. A patient with a cholestatic condition can be diagnosed and followed clinically based on a set of standard clinical laboratory tests, including measurement of levels of alkaline phosphatase, γ-glutamyl transpeptidase (GGT), 5' nucleotidase, bilirubin, bile acids, and cholesterol in a patient's blood serum. Generally, a patient is diagnosed as having a cholestatic condition if serum levels of all three of the diagnostic markers alkaline phosphatase, GGT, and 5' nucleotidase, are considered abnormally elevated. The normal serum level of these markers may vary to some degree from laboratory to laboratory and from procedure to procedure, depending on the testing protocol. Thus, a physician will be able to determine, based on the specific laboratory and test procedure, what an abnormally elevated blood level is for each of the markers. For example, a patient suffering from a cholestatic condition generally has greater than about 125 IU/L alkaline phosphatase, greater than about 65 IU/L GGT, and greater than about 17 NIL 5"nucleotidase in the blood. Because of the variability in the level of serum markers, a cholestatic condition may be diagnosed on the basis of abnormal levels of these three markers in addition to at least one of the symptoms mentioned above, such as itching (pruritus).

The term "primary biliary cirrhosis", often abbreviated PBC, is an autoimmune disease of the liver marked by the slow progressive destruction of the small bile ducts of the liver, with the intralobular ducts (Canals of Hering) affected early in the disease. When these ducts are damaged, bile builds up in the liver (cholestasis) and over time damages the tissue. This can lead to scarring, fibrosis and cirrhosis. Primary biliary cirrhosis is characterized by interlobular bile duct destruction. Histopathologic findings of primary biliary cirrhosis include: inflammation of the bile ducts, characterized by intraepithelial lymphocytes, and periductal epithelioid granulomata. There are 4 stages of PBC.

- Stage 1—Portal Stage: Normal sized triads; portal inflammation, subtle bile duct damage. Granulomas are often detected in this stage.
- Stage 2—Periportal Stage: Enlarged triads; periportal fibrosis and/or inflammation. Typically this stage is characterized by the finding of a proliferation of small bile ducts.
- Stage 3—Septal Stage: Active and/or passive fibrous septa.
- Stage 4—Biliary Cirrhosis: Nodules present; garland The term "primary sclerosing cholangitis" (PSC) is a disease of the bile ducts that causes inflammation and subsequent obstruction of bile ducts both at a intrahepatic (inside the liver) and extrahepatic (outside the liver) level. The inflammation impedes the flow of bile to the gut, which can ultimately lead to cirrhosis of the liver, liver failure and liver cancer.

The term "Nonalcoholic steatohepatitis" (NASH) is liver inflammation caused by a buildup of fat in the liver. In some people, the buildup of fat causes inflammation of the liver. Because of the inflammation, the liver doesn't work as well as it should. NASH can get worse and cause scarring of the liver, which leads to cirrhosis. NASH is similar to the kind of liver disease that is caused by long-term, heavy drinking. But NASH occurs in people who do not abuse alcohol.

The term "organ" refers to a differentiated structure (as in a heart, lung, kidney, liver, etc.) consisting of cells and tissues and performing some specific function in an organism. This term also encompasses bodily parts performing a function or cooperating in an activity (e.g., an eye and related structures that make up the visual organs). The term "organ" further encompasses any partial structure of differentiated cells and tissues that is potentially capable of developing into a complete structure (e.g., a lobe or a section of a liver).

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the description and examples provided herein are for purposes of illustration and not limitation of the claims that follow.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control. All percentages and ratios used herein, unless otherwise indicated, are by weight.

EXAMPLES

Example 1: Bile Duct Ligation (BDL) Model

This experiment was performed to evaluate the effects of OCA and atorvastatin alone, and in combination, on fibrosis induced by common bile duct ligation in mice.

Animals, Housing and Diet

Male C57BL/6 mice (6 weeks of age) were obtained from Japan SLC. The animals were maintained in a specific pathogen free facility under controlled conditions of temperature (23±2° C.), humidity (45±10%), lighting (12-hour artificial light and dark cycles; light from 8:00 to 20:00), and air exchange (air exchange rate: more than 40 times/hour). A high pressure (20±4 Pa) was maintained in the experimental room to prevent contamination of the facility. The animals were housed in KN-600 (Natsume Seisakusho, Japan) with a maximum of 6 mice per cage. Sterilized Paper-Clean (Japan SLC) was used for bedding and replaced once a week. Sterilized solid high fat diet (HFD) and water were provided ad libitum for 3 weeks before the day of surgery.

Treatment Groups

Group 1: Sham
  Sham-operated mice (n=8) were orally administered vehicle (0.5% CMC) in a volume of 5 mL/kg once daily from day 0 to day 6 after BDL surgery.

Group 2: BDL-Vehicle
  BDL-operated mice (n=12) were orally administered vehicle (0.5% CMC) in a volume of 5 mL/kg once daily from day 0 to day 6 after BDL surgery.

Group 3: BDL-OCA
  BDL-operated mice (n=12) were orally administered vehicle supplemented with OCA at a dose of 5 mg/kg once daily from day 0 to day 6 after BDL surgery.
Group 4: BDL-Atorvastatin
  BDL-operated mice (n=12) were orally administered vehicle supplemented with atorvastatin at a dose of 10 mg/kg once daily from day 0 to day 6 after BDL surgery.
Group 5: OCA-BDL-Atorvastatin
  BDL-operated mice (n=12) were orally administered vehicle supplemented with OCA at a dose of 5 mg/kg and atorvastatin at a dose of 10 mg/kg once daily from day 0 to day 6 after BDL surgery.

Bile Duct Ligation Surgery

Bile duct ligation surgery was performed at day 0. Cholestasis, which leads to fibrosis of the liver over time, was established in the mice by the ligation of the common bile duct under pentobarbital anesthesia. Mice were divided into two surgical cohorts based on their weight before the day of surgery. After shaving the hair, the abdominal cavity was opened and the common bile duct was ligated twice with 5-0 surgical silk and the common bile duct was cut between the ligatures. The peritoneum and the skin were closed with sutures. The mice were transferred to a clean cage (resting cage) for recovery from anesthesia. Sham mice were operated in a similar manner to other groups but the bile duct not ligated.

Animal Monitoring and Sacrifice

Viability, clinical signs and behavior were monitored daily. Body weight was recorded daily during the treatment period. Food consumption was measured twice weekly per cage during the treatment period. At day 6, the animals were sacrificed by exsanguination through the direct cardiac puncture under ether anesthesia (Wako Pure Chemical Industries).

Histological Analysis

To visualize collagen deposition, Bouin's-fixed left lateral liver sections were stained using picro-Sirius red solution (Waldeck, Germany). For quantitative analysis of the fibrosis area, bright field images of Sirius red-stained sections were captured around the central vein using a digital camera (DFC295; Leica, Germany) at 100-fold magnification, and the positive areas in 5 fields/section were measured using ImageJ software (National Institute of Health, USA). Statistical analyses were performed using Prism Software 6 (GraphPad Software, Inc. USA).

Results

Figure 2:
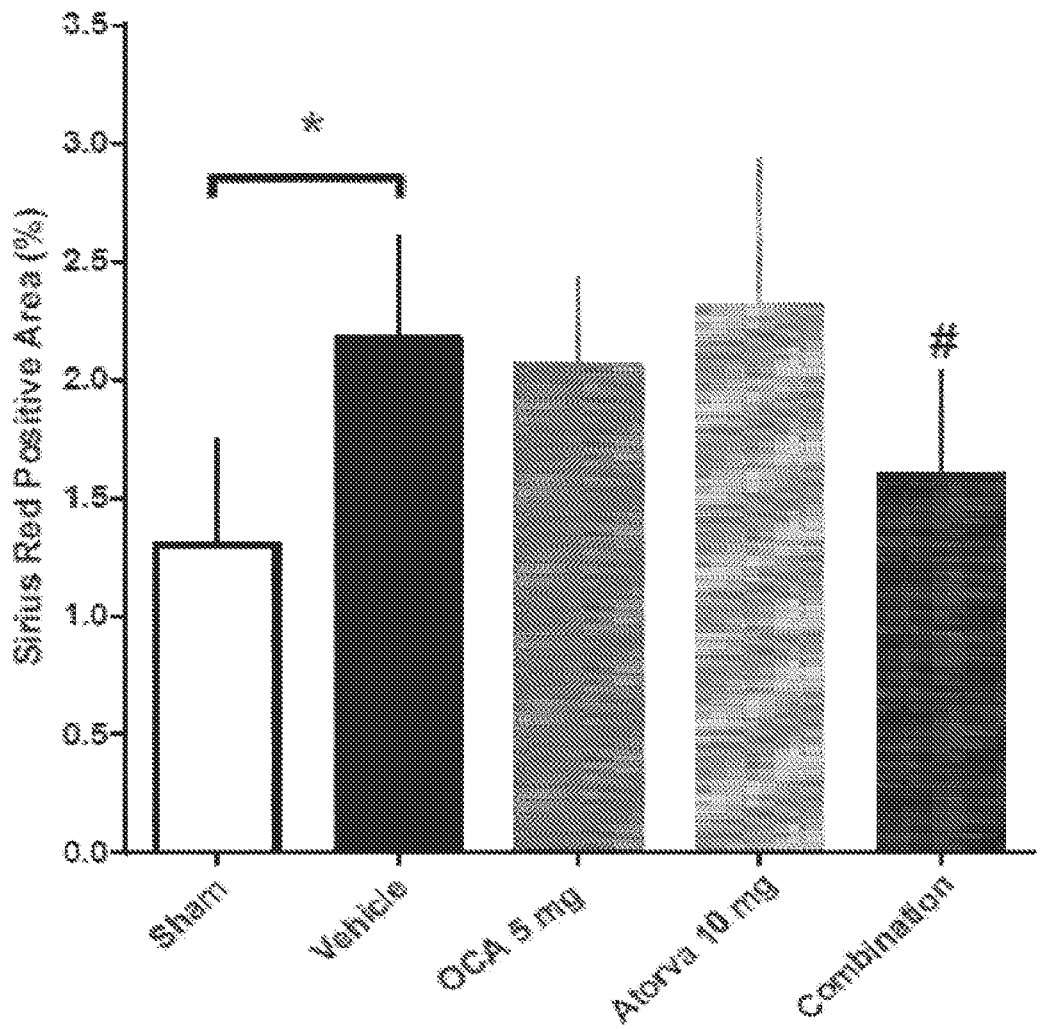
FIG. 2 is a bar graph showing the Sirius-red positive area (%) in BDL mice treated with OCA and atorvastatin alone and in combination.

Histopathological analyses were performed on liver sections (according to routine methods) by Sirius-red staining to estimate the percentage of fibrosis area. Representative photomicrographs of Sirius red-stained liver sections are shown in FIGS. 1A-1E. The BDL-Vehicle group showed a significant increase in Sirius red-positive area compared with the BDL-Sham group. As indicated in Table 1 and FIG. 2, the BDL-OCA+atorvastatin group showed a significant decrease in Sirius red-positive area compared with the BDL-Vehicle group.

TABLE 1

| Parameter (mean ± SD) | Sham (n = 8) | BDL-Vehicle (n = 11) | BDL-OCA (n = 12) | BDL-ATO (n = 12) | BDL-OCA + ATO (n = 12) |
|---|---|---|---|---|---|
| Sirius red-positive area (%) | 1.30 ± 0.45 | 2.17 ± 0.43 | 2.06 ± 0.37 | 2.31 ± 0.63 | 1.60 ± 0.44 (p < 0.05) |

The results in Table 1 indicate that the combination of OCA and atorvastatin significantly reduced fibrosis.

Example 2: Diet Induced NASH in APOE*3Leiden.CETP Mice

This experiment was performed to evaluate the effects of OCA and fenofibrate, alone or in combination, on the development of diet induced NASH and liver fibrosis in APOE*3Leiden.CETP transgenic mice. Hepatic gene expression profiling and subsequent pathway analysis were performed to determine whether the combination regulates novel genes not regulated by either monotherapy treatment, and/or more strongly regulates genes also impacted by the monotherapy.

Animals, Housing and Diet

Male APOE*3Leiden.CETP transgenic mice (9-21 weeks old) were obtained and housed 2-5 mice per cage. The mice were fed a high fat diet containing 24% lard and 1% (w/w) cholesterol. The run in period was 15 weeks on the high fat diet. At week 16, mice were matched based on age, body weight, plasma cholesterol and triglycerides after 4 h fasting.

Treatment Groups

Group 1: HFC reference group start treatment
  Mice (n=15) were fed a high fat diet during the run in weeks 0 to 14.
Group 2: HFC control group
  Mice (n=15) were fed a high fat diet from weeks 0 to 24.
Group 3: HFC+OCA
  Mice (n=15) were fed a high fat diet supplemented with OCA at a dose of 10 mg/kg once daily from week 16 to 24.
Group 4: HFC+low dose fenofibrate
  Mice (n=15) were fed a high fat diet supplemented with fenofibrate at a dose of 10 mg/kg once daily from week 16 to 24.
Group 5: HFC+high dose fenofibrate
  Mice (n=15) were fed a high fat diet supplemented with fenofibrate at a dose of 40 mg/kg once daily from week 16 to 24.
Group 6: HFC+OCA+low dose fenofibrate
  Mice (n=15) were fed a high fat diet supplemented with OCA at a dose of 10 mg/kg once daily and fenofibrate at a dose of 10 mg/kg once daily from week 16 to 24.
Group 7: HFC+OCA+high dose fenofibrate
  Mice (n=15) were fed a high fat diet supplemented with OCA at a dose of 10 mg/kg once daily and fenofibrate at a dose of 40 mg/kg once daily from week 16 to 24.
Group 8: Chow control group
  Mice (n=8) were feed chow from week 0 to 24.

Study Design

Mice were fed a high fat chow (HFC) diet for 14 weeks. After 15 weeks on the HFC diet, HFC mice were matched into 7 groups based on age, body weight, plasma cholesterol and triglycerides after 4 h fasting. Mice were treated with of OCA and fenofibrate, alone or in combination beginning at week 15 and sacrificed at week 25 in an unfasted state. One week before sacrifice, mice were labeled with D20, by i.p. injection of a bolus of D20 and subsequent addition of 4% D20 to the drinking water. Plasma (EDTA) was obtained by heart puncture and stored at −70° C. The liver was weighed and 4 pieces of liver were isolated: 1 piece (medial lobe) was fixed in 10% formalin (for NASH and fibrosis histology) and 3 pieces (sinister lobe) were snap-frozen in liquid $N_2$ and stored individually at −70° C.

Hepatic Inflammation Score

Inflammation is a key feature of NASH. Inflammation was categorized according to the procedure by Liang et al., PlosOne 2014 Dec. 9(12) and scored by quantitatively analyzing the number of inflammatory cells aggregates. In particular, the level of inflammation was evaluated by counting the number of inflammatory foci per field using a 100× magnification (view size of 3.1 mm2; average of five different fields).

Figure 3B:
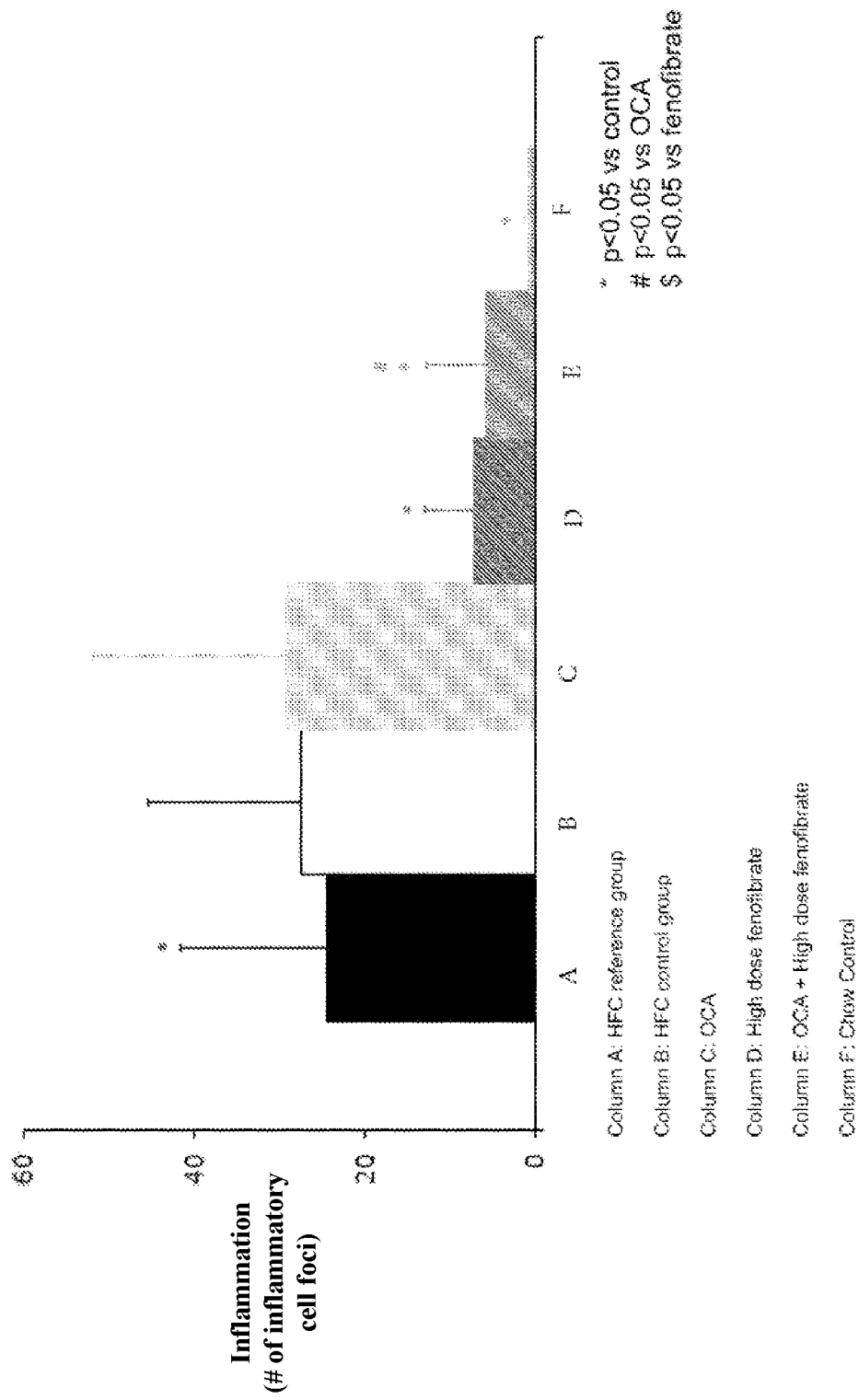
FIG. 3B is a bar graph showing the number of inflammatory cell foci from the treatment of OCA, high dose fenofibrate alone and in combination in APOE*3Leiden.CETP mice.

Results: Summary of Effects of OCA+/−Fenofibrate on Inflammation in APOE*3-Leiden.CETP Mice The effects of OCA 10 mg/kg were investigated alone and in combination with fenofibrate (10 and 40 mg/kg) on inflammation in APOE*3-Leiden.CETP mice on a NASH diet. After 10 weeks of drug administration at the low dose, neither OCA (10 mg/kg) nor fenofibrate (10 mg/kg) reduced the number of inflammatory cell foci (FIGS. 3A and 3B and Table 2). By contrast, the combination significantly decreased inflammation relative to the vehicle control as well as each monotherapy arm. A higher dose of fenofibrate (40 mg/kg/d) also significantly reduced inflammation relative to vehicle controls. When combined with OCA, no additional anti-inflammatory effects were evident as the high dose of fenofibrate exerted a near-maximal effect on its own. In summary, a significant reduction in inflammation with the OCA+low dose fenofibrate combination (−63%) was observed. Furthermore, a significant reduction with the high dose of fenofibrate (−74%) and a similar reduction in combination with OCA (−79%) were observed. See Table 2 and FIGS. 3A and 3B.

TABLE 2

| Group | Inflammation (# of inflammatory cell foci) |
|---|---|
| Group 1: HFC reference group | 24.3 ± 17.3 |
| Group 2: HFC control group | 27.5 ± 18.0 (n = 15) |
| Group 3: OCA | 29.1 ± 22.7 |
| Group 4: low dose fenofibrate | 22.0 ± 15.6 |
| Group 5: high dose fenofibrate | 7.1 ± 5.9 |
| Group 6: OCA + low dose fenofibrate | 10.0 ± 7.0 |
| Group 7: OCA + high dose fenofibrate | 5.1 ± 7.0 |
| Group 8: Chow control | 0.8 ± 0.4 |

The results in Table 2 suggests that the efficacy of the combination of OCA and the high dose of fenofibrate is driven and reaches an upper limit by the high dose of fenofibrate.

RNA Isolation and Sequencing

Nucleic acid extraction was performed as described previously in detail (Verschuren et al., 2014). Briefly, total RNA was extracted from individual liver samples using glass beads and RNAzol (Campro Scientific, Veenendaal, The Netherlands). RNA concentration and quality was determined using the Fragment Analyzer (Advanced Analytical Technologies, USA) and the RNA 6000 Nano Lab-on-a-Chip kit and a Bioanalyzer 2100 (Agilent Technologies, Amstelveen, The Netherlands). All samples met the quality requirements and were used in the RNA sequencing procedure.

The NEBNext Ultra Directional RNA library Prep Kit for Illumina was used to process the samples. The sample preparation was performed according to the protocol "NEBNext Ultra Directional RNA Library Prep Kit for Illumina" (NEB #E7420S/L). Briefly, mRNA was isolated from total RNA using oligo-dT magnetic beads. After fragmentation of the mRNA, a cDNA synthesis was performed. This was used for ligation of sequencing adapters and PCR amplification of the resulting product. The quality and yield after sample preparation was measured with the Fragment Analyzer (Advanced Analytical Technologies, USA). The size of the resulting products was consistent with the expected size distribution (a broad peak between 300-500 bp).

Clustering and DNA sequencing using the Illumina NextSeq 2500 was performed according manufacturer's protocols. Data was generated using single-end read sequencing protocol obtaining approx. 15 million reads per sample and 75 bp per read. Image analysis, base calling, and quality check was performed with the Illumina data analysis pipeline RTA v2.4.11 to generate the raw data (*.fastq-files).

The reads were mapped to the reference sequence *Mus musculus* GRCm38.p3 using a short read aligner based on Burrows-Wheeler Transform. The default mismatch rate of 2% (3 mismatches in a read of 150 bases) was used. Based on the mapped read locations in the alignment files (*.bam-files) the frequency of how often a read was mapped on a transcript was determined. The counts were saved to count-files, which served as input for downstream mRNA-seq differential expression analysis. The read counts were loaded into the DESeq package, a statistical package within the R platform. DESeq was specifically developed to normalize RNA-seq data for different samples and find differentially expressed genes between two conditions for RNA-seq data to estimate the relationship between the mean and variance of each gene (Anders et al., 2013). Furthermore, it allows scaling factors to be easily included in the statistical test. Differentially expressed genes were identified using a threshold for significance of P<0.01 and genes were used as an input for pathway analysis through Ingenuity Pathway Analysis (IPA) suite (accessed 2016).

Upstream regulator analysis was performed using the IPA software (Kramer et al., 2014). This analysis determines the activation state of transcription factors based on the observed differential gene expression. This results in an overlap P-value and activation z-score for each transcription factor in the IPA knowledge base. The overlap P-value indicates the significance of the overlap between the known target genes of a transcription factor and the differentially expressed genes measured in an experiment. The activation z-score indicates activation (positive z-score) or inhibition (negative z-score) of a particular transcription factor. An activation z-score <−2 or >2 indicates significant inhibition or activation of a pathway or process.

Omics Results

Next Generation Sequencing was performed on liver mRNA samples from treated mice to gain insight into the underlying mechanisms and pathways. Two analyses were performed to gain insight into the underlying mechanisms and pathways.

Figure 6A:
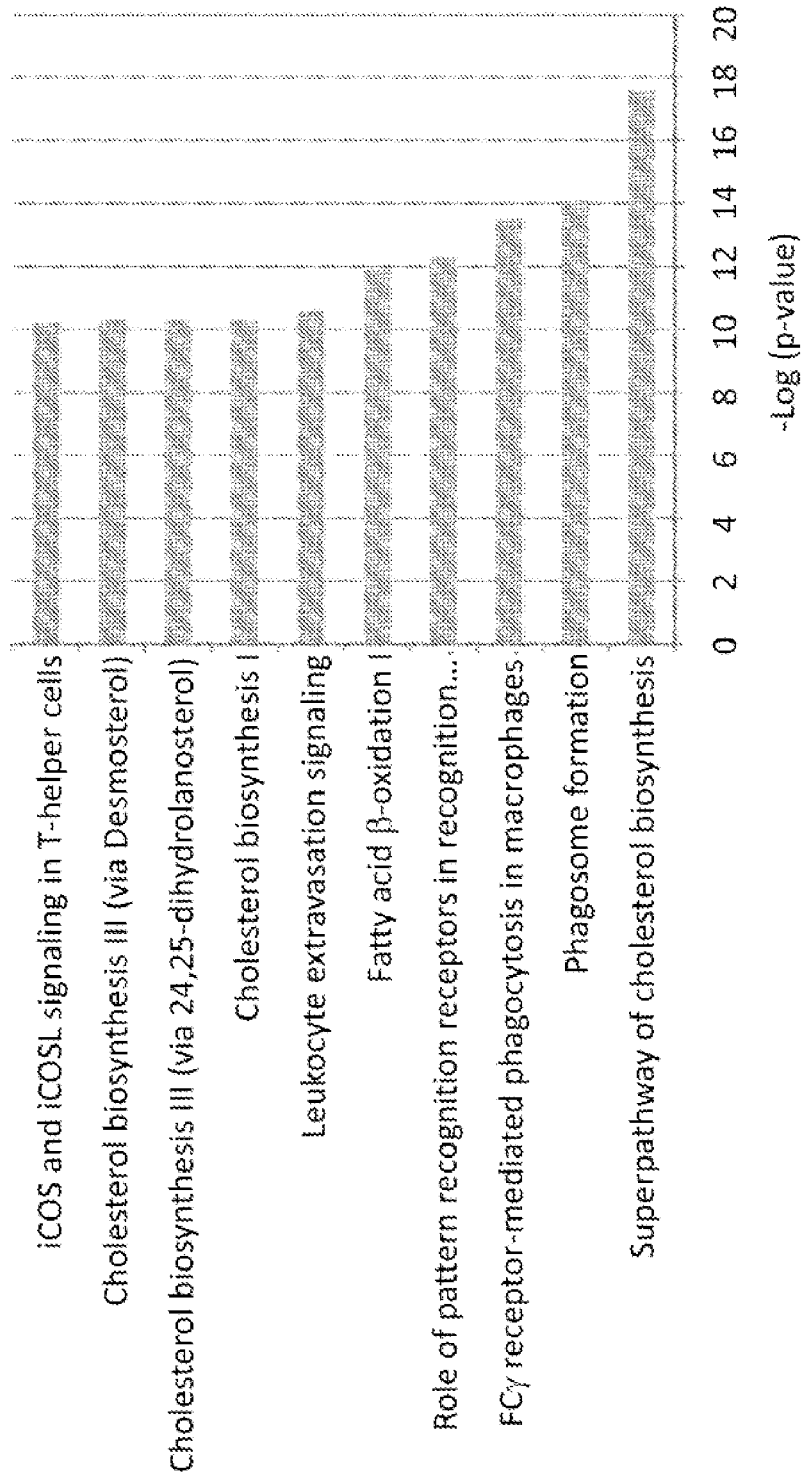
FIG. 6A is a bar graph showing an enrichment analysis of the canonical pathways of HFC+OCA against HFC sustained APOE*3Leiden.CETP mice.
Figure 6B:
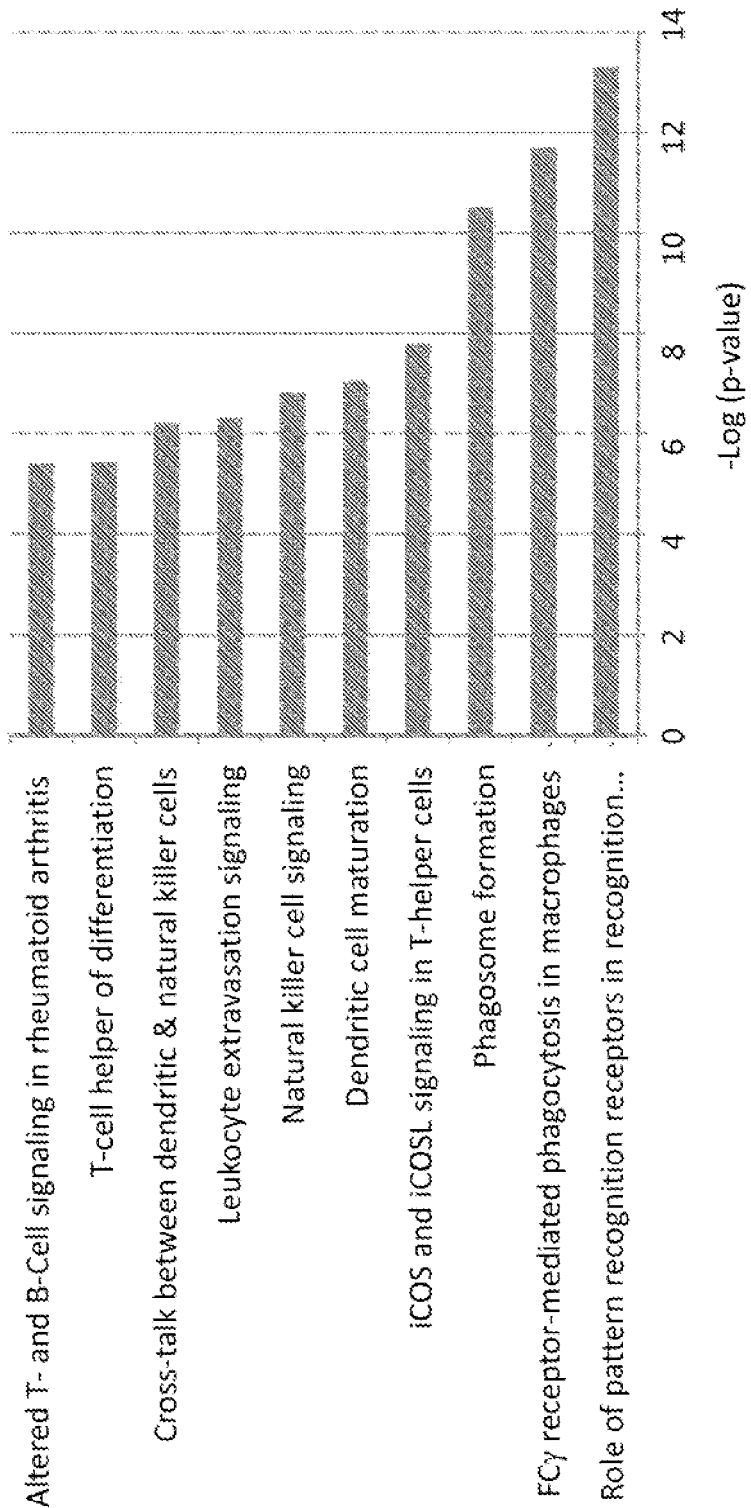
FIG. 6B is a bar graph showing an enrichment analysis of the canonical pathways of HFC+OCA+low dose fenofibrate against HFC sustained APOE*3Leiden.CETP mice

First, an enrichment analysis of the canonical pathways analysis revealed that OCA regulated several inflammatory processes (FIG. 6A). The figure plots each pathway as a function of −log p-value (for reference a transformed value for p<0.05 is 1.3, p<0.0001 is 4, for p<0.000005 is 5.3 etc.). The regulated pathways with OCA monotherapy were related to T- and B-cell signing, leukocyte extravasation signaling, natural killer cell signaling etc. The low dose of fenofibrate had no effect on these pathways. When OCA was combined with the low dose of fenofibrate, some of the same pathways were strongly regulated (in the case of iCOS-iCOSL signaling in T-helper cells, leukocyte extravasation signaling, pattern recognition receptors, FC receptor-mediated phagocytosis in macrophages, and phagosome formation). Additionally, other pathways (e.g., cholesterol biosynthesis I and II, fatty acid b-oxidation) that were not significantly regulated by either agent alone were regulated by the combination (FIG. 6B). As with the histological data, the high dose of fenofibrate had a robust effect on these pathways but was not enhanced with OCA co-administration.

A more detailed analysis was performed around the pathways involved in leukocyte extravasation signaling. Extravasation of leukocytes is essential for pathophysiological processes in NASH (and other diseases). These processes include migration of T-lymphocytes for immune surveillance, recruitment of activated lymphocytes and granulocytes during acute and chronic inflammatory responses, and homing and mobilization of hematopoietic progenitor cells. The effects of maintaining mice on a high-fat diet from the study illustrates these processes in which significantly upregulated and down-regulated genes. Table 3 describes the effects of a high-fat diet on leukocyte extravasation signaling in mice maintained on a high-fat diet relative to mice maintained on standard chow, and also the effects of combination treatment relative to high fat diet.

TABLE 3

| Gene | Full Name/s | Predicted Function | Significantly regulated by NASH Diet vs. CHOW | Significantly regulated by Combo vs. NASH DIET |
|---|---|---|---|---|
| CD43 | Cluster of differentiation 43 or leukosialin | Major sialoglycoprotein located on the surface of T lymphocytes, monocytes, granulocytes and some B lymphocytes. | ↑ | ↓ |
| CD44 | Cluster of differentiation 44 | Cell-surface glycoprotein involved in cell-cell interactions, cell adhesion and migration | ↑ | ↓ |
| CDH5 | Cadherin 5 or CD144 | Imparts cells the ability to adhere in a hemophilic manner and controls cohesion and organization of intercellular junctions | ↑ | ⇔ |
| CRK | CT10 regulator of kinase or p38 | Adapter protein in intracellular signaling pathways | ↓ | ⇔ |
| CXCR4 | Chemokine C-X-C Motif Receptor 4 or CD184 | Receptor for chemotactic activity for lymphocytes | ↑ | ↓ |
| ERM | Exrin, Radixzin, Moesin protein family | Crosslinks actin filaments with plasma membranes | ↓ | ↓ |
| EPAC | Exchange protein activated by cAMP | Intracellular sensors for cAMP | ↓ | ⇔ |
| ICAM-1 | Intracellular adhesion molecule 1 or CD54 | Cell surface glycoprotein that binds integrins | ↑ | ↓ |
| ITGA4 | Integrin alpha subunit | Large subunit of a4b1 lymphocyte homing receptor | ↑ | ↓ |
| ITGAL | Integrin alpha L or CD11A | Cellular adhesion and costimulatory signaling | ↑ | ↓ |
| ITGAM | Integrin Alpha M or CD11B | Regulates leukocyte adhesion and migration | ↑ | ↓ |
| ITGB1 | Integrin Beta-1 or CD29 | Integrins participate in cell adhesion and cell-surface mediated signaling | ↓ | ⇔ |
| ITGB2 | Integrin Beta-2 or CD18 | Integrins participate in cell adhesion and cell-surface mediated signaling | ↑ | ↓ |
| JAM2 | Junction adhesion molecule 2 or CD322 | Adhesive ligand for interacting with multiple immune cell types and lymphocyte homing | ↑ | ⇔ |
| JAM3 | Junction adhesion molecule 3 | Binds with JAM2 in the regulation of adhesion | ↓ | ⇔ |
| LFA-1 | Lymphocyte function-associated antigen 1 | Adhesion molecule on T-cells, B-cells, macrophages and neutrophils | ⇔ | ↓ |
| NCF1 | Neutrophil cytosolic factor-1 | A subunit of the neutrophil NADPH oxidase | ↑ | ↓ |
| NCF2 | Neutrophil cytosolic factor-2 | A subunit of the neutrophil NADPH oxidase | ↑ | ↓ |
| NCF4 | Neutrophil cytosolic factor-4 | A subunit of the neutrophil NADPH oxidase | ↑ | ↓ |

TABLE 3-continued

| Gene | Full Name/s | Predicted Function | Significantly regulated by NASH Diet vs. CHOW | Significantly regulated by Combo vs. NASH DIET |
|---|---|---|---|---|
| NOX | NADPH oxidase | Enzymes that transport electrons across plasma membrane and generate superoxides and downstream reactive oxygen species | ↑ | ↓ |
| PECAM1 | Platelet endothelial cell adhesion molecule or CD31 | Leukocyte transmigration, angiogenesis, and integrin activation | ↑ | ⇔ |
| PKC | Protein kinase C | Part of family of enzymes controlling phosphorylation of serine and threonine amino acids on other proteins | ⇔ | ⇔ |
| PI3K | PI3-kinases | PI3Ks are a family of related intracellular signal transducer enzymes | ⇔ | ↓ |
| PLC | Phospholipase C | catalyzes the formation of inositol 1,4,5-trisphosphate and diacylglycerol from phosphatidylinositol 4,5-bisphosphate | ⇔ | ↓ |
| PSGL-1 | P-selectin Glycoprotein Ligand 1 | Role in leukocyte trafficking during inflammation by tethering of leukocytes to activated platelets or endothelia expressing selectins | ↑ | ↓ |
| Rac2 | Ras-related C3 botulinum toxin substrate | Regulates diverse cellular events including growth, cytoskeletal reorganization and activation of protein kinases | ↑ | ↓ |
| RASGRP1 | RAS guanyl nucleotide-releasing protein | Activates Erk/MAP kinase cascade and regulates T- and B-cell development homeostasis and differentiation | ↑ | ↓ |
| RhoH | Ras homolog gene H | Regulates intracellular actin dynamics | ↑ | ↓ |
| RhoGAP | RHO GTPases | Protein domain of GTPase activating proteins | ⇔ | ↓ |
| SPA-1 | Signal-induced proliferation associated protein 1 | May hamper mitogen-induced cell cycle progression when abnormally expressed | ↑ | ⇔ |
| THY-1 | Thymocyte differentiation antigen 1 or CD90 | Cell-cell and cell-matrix interactions, may impact neurite outgrowth, nerve regeneration, apoptosis, metastasis, inflammation, and fibrosis | ↑ | ↓ |
| TIMP | Tissue inhibitor of metalloproteinase | Bind and inactivate tissue metalloproteinases | ⇔ | ↓ |
| VASP | Vasodilator-stimulated phosphoprotein | Involved in intracellular signaling pathways that regulate integrin-extracellular matrix interactions | ↑ | ↓ |
| VAV | VAV | A protooncogene mediating antigen-induced activation of B lymphocytes | ↑ | ↓ |
| VCAM1 | Vascular cell adhesion protein 1 or CD 106 | Adhesion of lymphocytes, monocytes, eosinophils, and basophils to vascular endothelium | ↑ | ↓ |
| WASP | Wiskott-Adlrich Syndrome) | Important in leukocyte motility in vivo | ⇔ | ↓ |

Transmigration and extravasation of leukocytes across the endothelium occurs in several distinct steps including rolling of the leukocytes over the endothelial cells, mediated by transient weak interactions between adhesion molecules. Subsequently, loosely attached leukocytes are in such close proximity of the endothelium that they are activated by chemotactic cytokines, presented on the apical surface of the endothelium. Next, activated leukocytes spread and firmly adhere to the endothelium forming docking structures and ultimately migrate through the intercellular clefts between the endothelial cells to the underlying tissue.

The administration of OCA downregulates numerous genes involved in this process of the inflammatory cascade within the leukocyte (WAP, Rac2, RASGRP1, Vav, PKC, PI3K, ERM, ITGAL and PSGL-1) as well as within endothelial cells (VCAM1, PI3K, ERM, NOX, CYBA, PKC, NCF1 and 2). Gene regulation within these pathways was not evident following administration of a low dose of fenofibrate alone.

When OCA was combined with a dose of fenofibrate that was ineffective at regulating these pathways, multiple additional genes are now regulated pointing to a synergistic effect. Within the leukocyte these additional genes included CD43, PSGL-1, CXCR4, ITGAM, ITGB2, Rap1, ITGA4. Within the endothelial cell these additional genes included ICAM1, RhoGAP, VASP, NCF4, ITGAM, ITGB2, ITGA4 and ICAM-1.

As noted above, the high dose of fenofibrate had numerous effects on this pathway that were not enhanced with OCA co-administration. All subsequent analyses focused on the low dose monotherapies and combination (OCA 10 mg/kg+/−fenofibrate 10 mg/kg).

Figure 7A:
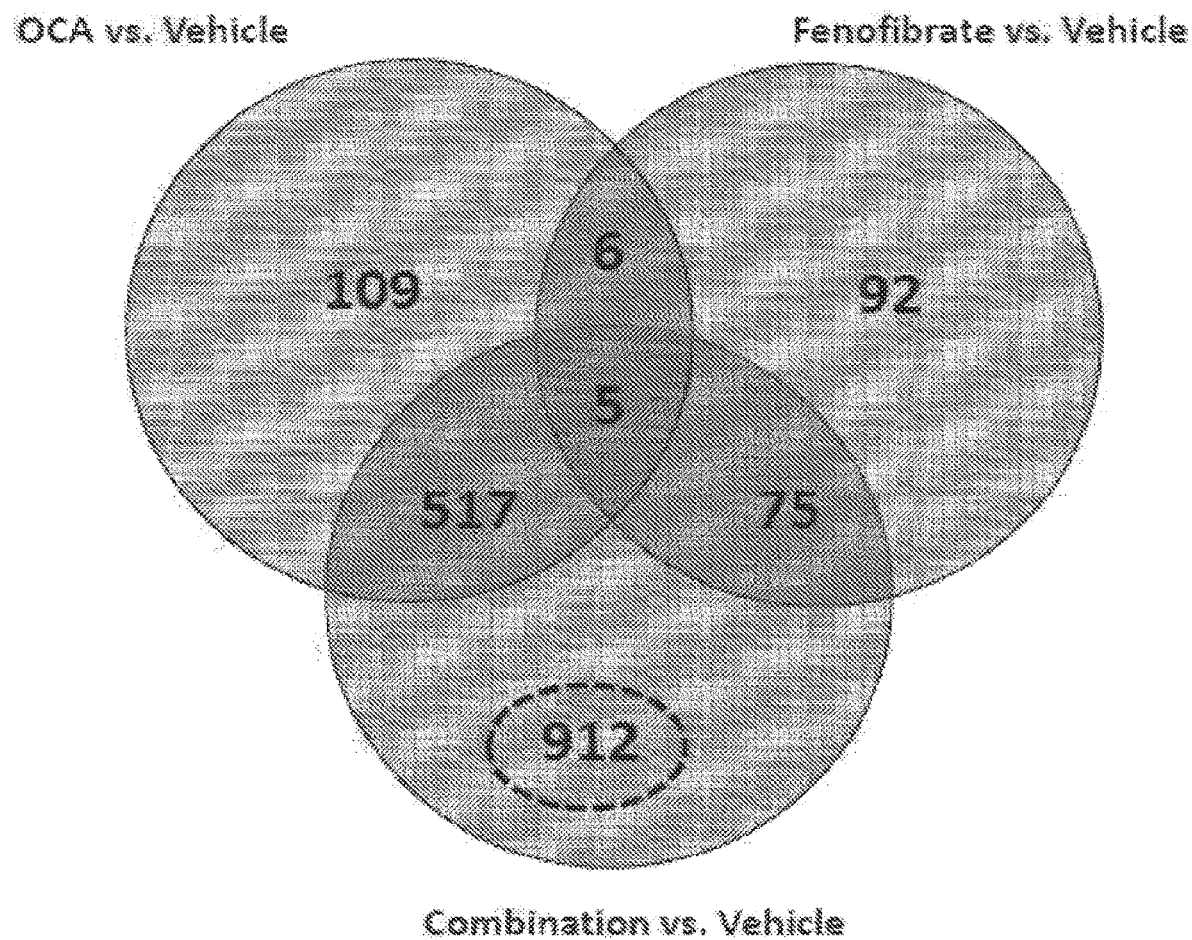
FIG. 7A is a venn diagram showing the number of novel differentially expressed genes regulated by the combination of OCA+low dose fenofibrate versus monotherapy in APOE*3Leiden.CETP mice.
Figure 7B:
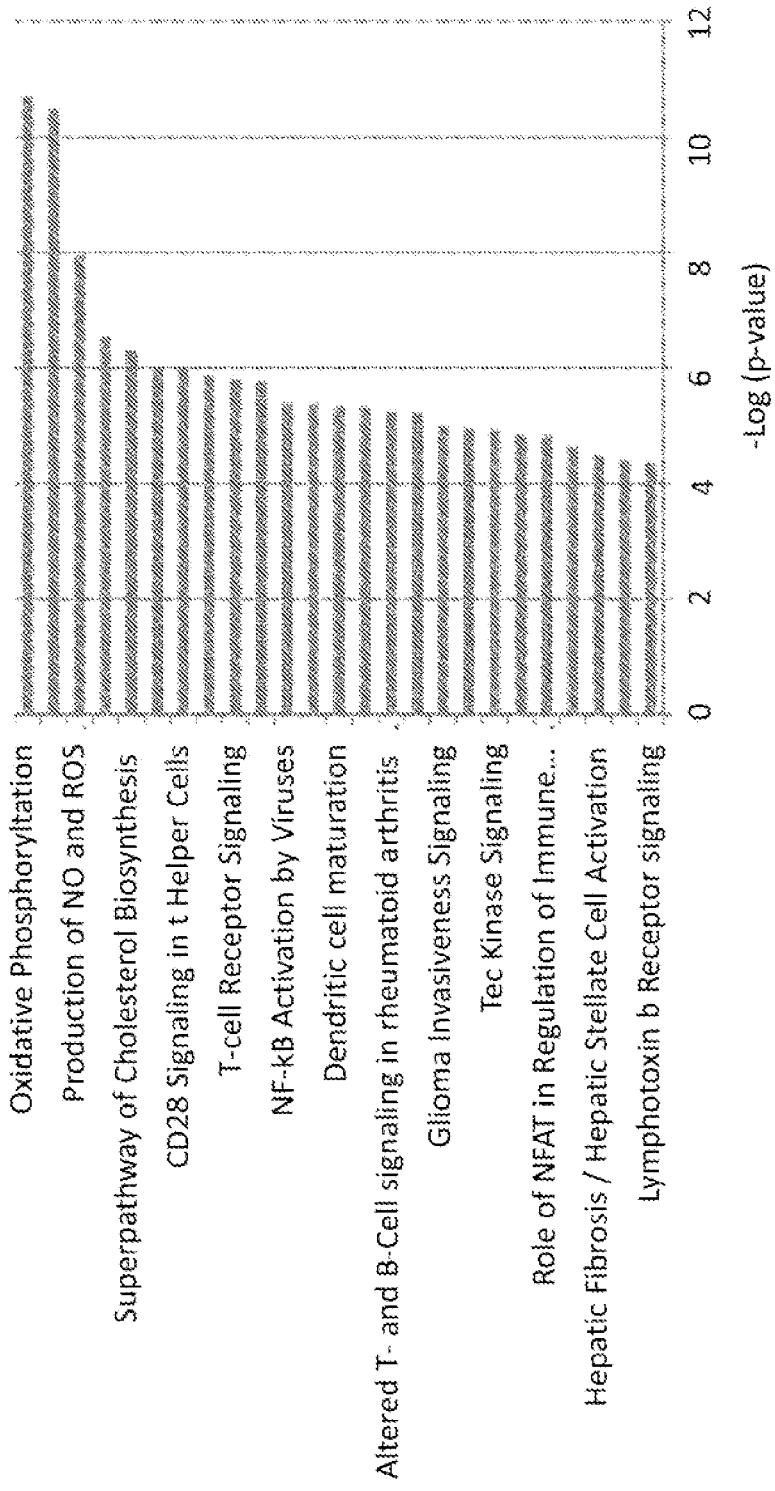
FIG. 7B is a bar graph showing the pathway enrichment of genes regulated by the combination of OCA+low dose fenofibrate against monotherapy in APOE*3Leiden.CETP mice.

In a second analysis, the genes differentially regulated between the low dose combination and each respective monotherapy were compared. This differs from the first gene expression analyses (described above) which focused on comparisons relative to the vehicle group; the analysis below compares each monotherapy to the combination. The Venn diagram (FIG. 7A) shows that OCA has 109 uniquely regulated genes, fenofibrate has 92 uniquely regulated genes and 6 commonly regulated genes. The combination regulated 517 overlapping genes with OCA, 75 with fenofibrate, and 5 genes were common to all. Of note, the combination regulated a total of 912 unique genes. A subsequent pathway enrichment highlights the biological processes in which the combination genes are involved (FIG. 7B).

Subsequent pathway analyses were conducted both for leukocyte extravasation (e.g., as above but this time comparisons are between the combination and each monotherapy. For leukocyte extravasation, comparisons of the combination versus each monotherapy revealed that there were a number of uniquely regulated genes consistent with the observed enhanced anti-inflammatory changes noted histologically in the combination-treated mice (Table 4).

TABLE 4

| Gene | Full Name/s | Predicted Function | Combination vs. Fenofibrate Monotherapy | Combination vs. OCA Monotherapy |
|---|---|---|---|---|
| CD44 | Cluster of differentiation 44 | Cell-surface glycoprotein involved in cell-cell interactions, cell adhesion and migration | | ↓ |
| CXCR4 | Chemokine C-X-C Motif Receptor 4 or CD184 | Receptor for chemotactic activity for lymphocytes | | ↓ |
| CYBA1 | Cytochrome b(-245) | Encodes alight chain of cytochrome b(-245) which is a component of the NOX complex | | ↓ |
| ERM | Exrin, Radixzin, Moesin protein family | Crosslinks actin filaments with plasma membranes | | ↓ |
| ICAM-1 | Intracellular adhesion molecule 1 or CD54 | Cell surface glycoprotein that binds integrins | ↓ | ↓ |
| ITGA4 | Integrin alpha subunit | Large subunit of a4b1 lymphocyte homing receptor | ↓ | ↓ |
| ITGAL | Integrin alpha L or CD11A | Cellular adhesion and costimulatory signaling | | ↓ |
| ITGAM | Integrin Alpha M or CD11B | Regulates leukocyte adhesion and migration | | ↓ |
| ITGB2 | Integrin Beta-2 or CD18 | Integrins participate in cell adhesion and cell-surface mediated signaling | ↓ | ↓ |
| LFA-1 | Lymphocyte function-associated antigen 1 | Adhesion molecule on T-cells, B-cells, macrophages and neutrophils | ↓ | ↓ |
| MMP9 | Matrix metalloprotease 9 | Degrades collagen of the extracellular matrix | | ↓ |
| NCF1 | Neutrophil cytosolic factor-1 | A subunit of the neutrophil NADPH oxidase | | ↓ |
| NCF2 | Neutrophil cytosolic factor-2 | A subunit of the neutrophil NADPH oxidase | | ↓ |
| NCF4 | Neutrophil cytosolic factor-4 | A subunit of the neutrophil NADPH oxidase | | ↓ |
| NOX | NADPH oxidase | Enzymes that transport electrons across plasma membrane and generate superoxides and downstream reactive oxygen species | | ↓ |
| PKC | Protein kinase C | Part of family of enzymes controlling phosphorylation of serine and threonine amino acids on other proteins | | ↓ |
| PI3K | PI3-kinases | PI3Ks are a family of related intracellular signal transducer enzymes | ↓ | ↓ |
| PLC□ | Phospholipase C | catalyzes the formation of inositol 1,4,5-trisphosphate and diacylglycerol from phosphatidylinositol 4,5-bisphosphate | | ↓ |

TABLE 4-continued

| Gene | Full Name/s | Predicted Function | Combination vs. Fenofibrate Monotherapy | Combination vs. OCA Monotherapy |
|---|---|---|---|---|
| PSGL-1 | P-selectin Glycoprotein Ligand 1 | Role in leukocyte trafficking during inflammation by tethering of leukocytes to activated platelets or endothelia expressing selectins | ↓ | ↓ |
| Rac2 | Ras-related C3 botulinum toxin substrate | Regulates diverse cellular events including growth, cytoskeletal reorganization and activation of protein kinases | | ↓ |
| Rap1GAP | RAP1 GTPase-activating protein 1 | RAP1 is of particular interest since it has been shown to be an antagonist of RAS and is capable of suppressing cellular transformation | | ↓ |
| RASGRP1 | RAS guanyl nucleotide-releasing protein | Activates Erk/MAP kinease cascade and regulates T- and B-cell development, homeostasis and differentiation | | ↓ |
| RhoH | Ras homolog gene H | Regulates intracellular actin dynamics | | ↓ |
| RhoGAP | RHO GTPases | Protein domain of GTPase activating proteins | | ↓ |
| TIMP | Tissue inhibitor of metalloproteinase | Bind and inactivate tissue metalloproteinases | | ↓ |
| VASP | Vasodilator-stimulated phosphoprotein | Involved in intracellular signaling pathways that regulate integrin-extracellular matrix interactions | | ↓ |
| VAV | VAV | A protooncogene mediating antigen-induced activation of B lymphocytes | | ↓ |
| VCAM1 | Vascular cell adhesion protein 1 or CD 106 | Adhesion of lymphocytes, monocytes, eosinophils, and basophils to vascular endothelium | | ↓ |
| WASP | Wiskott-Adlrich Syndrome) | Important in leukocyte motility in vivo | | ↓ |

Given the progression from inflammation to fibrosis in NASH, and the observation that hepatic fibrosis/HSC pathways emerged as significantly regulated in the combination we also examined pathways in HSCs. When compared against the monotherapy, it is clear that more genes are regulated in the combination versus fenofibrate alone and fewer genes are regulated in the combination versus OCA. In other words, with respect to these fibrotic pathways, there is clearly an interaction between both agents, but the OCA portion of the combination may be more strongly driving these effects.

Interpretation and Relevance

The importance of FXR activation in preventing fibrosis and inflammation is demonstrated in livers from FXR knockout mice which display elevated expression of inflammatory genes (Kim 2007) with progressive age-related injury and inflammation (Yang 2007). Consistent with these reports, OCA exerted anti-inflammatory properties in HepG2 cells and mouse primary hepatocytes. HepG2 cells pretreated with OCA and then exposed to pro-inflammatory stimuli exhibited a 50% to 60% reduction in TNF-α mRNA levels, cyclo-oxygenase-2 (COX-2) induction and TNF-α-stimulated inducible nitric oxide synthase (iNOS) expression. Likewise, OCA-treated primary hepatocytes displayed a blunted induction (by 40% to 50%) of iNOS and monocyte chemoattractant protein-1 (MCP-1) gene expression in response to pro-inflammatory stimuli (Wang 2008). The effects of OCA on mechanisms of cell migration have not been studied directly, however OCA inhibited the production of iNOS or COX-2 induced by IL-1β and abolished pharmacologically-induced rat aortic smooth muscle cell migration (Li 2007). Similar inhibition of inflammatory infiltrates with OCA has been demonstrated in the intestinal tissue of two animal models of inflammatory bowel disease (DSS and trinitrobenzene sulfonic acid) (Gadaleta 2011) and the kidney of a rat model of Type 1 diabetes (Wang 2010). Thus, the observation of enhanced anti-inflammatory effects by OCA suggests that changes in gene expression with OCA in combination with fenofibrate could enhance the inhibition of inflammation and inflammatory cell migration in a number of disease conditions.

Example 3: Diet Induced NASH in Leptin-Deficient Ob/Ob Mice

This experiment was performed to evaluate the effect of 8 weeks of treatment with OCA and atorvastatin alone and in combination on the fibrosis stage (pre-biopsy vs. post-biopsy) in male leptin-deficient ob/ob-NASH mice Animals, Housing and Diet Male $Lep^{ob}/Lep^{ob}$ mice (at 5 weeks of age) were purchased from JanVier, France. During the acclimatization and diet-induction period, the mice were group housed five per cage in custom-made cabinets under a 12:12 light dark cycle (lights on from 3 AM-3 PM) at controlled temperature conditions (22±1° C.; 50±10% relative humidity). Throughout the diet induction and study period, the mice had ad libitum access to custom made NASH diet (S8189, Ssniff, Germany) (40% fat, 40% carbohydrates (20% fructose) and 2% cholesterol) or regular rodent chow (ob/ob-CHOW)

(Altromin 1324, Brogaarden, Denmark), and tap water. The animals were kept on the diet for a total of 18 weeks before intervention and maintained on the diet throughout the study period. Animals were singly-housed during post-operative recovery and throughout the study period.

Treatment Groups

Group 1: $Lep^{ob}/Lep^{ob}$-NASH Vehicle
  Mice (n=10) were orally administered vehicle (0.5% CMC) in a volume of 5 mL/kg once daily from week 0 to 8.

Group 2: $Lep^{ob}/Lep^{ob}$-NASH OCA
  Mice (n=10) were orally administered vehicle supplemented with OCA at a dose of 30 mg/kg once daily from week 0 to 8.

Group 3: $Lep^{ob}/Lep^{ob}$-NASH
  Mice (n=11) were orally administered vehicle supplemented with Atorvastatin at a dose of 10 mg/kg once daily from week 0 to 8.

Group 4: $Lep^{ob}/Lep^{ob}$-NASH OCA+Atorvastatin
  Mice (n=9) were orally administered vehicle supplemented a combination of with OCA at a dose of 30 mg/kg and Atorvastatin at a dose of 30 mg/kg once daily.

Allocation into Studies, Stratified Randomization and Baseline Monitoring

After 15 weeks of diet induction (3 weeks prior to study start), a liver biopsy was obtained assessment of hepatic progression of fibrosis and steatosis, and for liver Fibrosis Stage evaluation. At week −1, a stratified randomization into treatment groups was performed according to liver fibrosis stage, steatosis score, and body weight.

Pre-Biopsy Procedure

On the day of the operation, mice were anesthetized with isoflurane (2-3%) in 100% oxygen. A small abdominal incision in the midline was made and the left lateral lobe of the liver was exposed. A cone shaped wedge of liver tissue (~100 mg) was excised from the distal portion of the lobe, weighed, and fixated in 4% paraformaldehyde (PFA) for histology. The cut surface of the liver was instantly electro-coagulated using bipolar coagulation (ERBE VIO 100 electrosurgical unit). The liver was returned to the abdominal cavity and the abdominal was sutured and the skin was closed with staplers. On the day of operation, mice received warmed saline (0.5 ml) for rehydration. For post-operation recovery, carprofen (5 mg/ml-0.01 ml/10 g) and enrofloxazin (5 mg/ml-1 ml/kg) were administered subcutaneously on the day of operation and post-operation days 1 and 2.

Pre-Screening for Assessment of Hepatic Level of Steatosis and Fibrosis

Liver biopsy preparation for histological assessment: After overnight storage in 4% PFA, liver biopsies were infiltrated overnight in paraffin in an automated Miles Scientific Tissue-TEK VIP Tissue Processor and subsequently embedded in paraffin blocks. Biopsies from five different animals were embedded on one block. The blocks were then trimmed and two 3 μm sections were cut (one for Sirius Red and one for H&E staining) on a Microm HM340E Microtome (Thermo Scientific). Two blocks were placed on one slide giving a total of 10 biopsies per slide representing 10 different animals. Sections were left to dry overnight. Evaluation of fibrosis stage for stratification and randomization into treatment groups were performed as outlined by Kleiner et al. (2005) (see below).

Baseline and Final Plasma Biomarkers

Blood samples for measuring non-fasting (fed) plasma levels of triglycerides were obtained in the morning (7-8 AM) at baseline and in week 8 of treatment. The blood samples were collected from the tail vein (by snipping) in a conscious state. The latest drug dose was administered ~18 hours before blood sampling. Mice were re-fed after the blood sampling.

Termination and Necropsy

Animals were terminated in week 8 in a non-fasting state. Latest drug dose was administered ~18 hours before termination and animals will not receive drug dosing prior to termination. Animals were induced by $CO_2/O_2$ and during anesthesia (isoflurane), the abdominal cavity is opened and cardiac blood obtained for collection of terminal plasma. Upon necropsy, whole liver was collected and weighed. A biopsy from the left lateral lobe was excised and fixated in 4% PFA for histology and biochemical analysis. The median lobe was divided into pieces and snap frozen in liquid nitrogen for biochemical analysis (TG). Remaining liver tissue was subsequently fixated in 4% PFA for later optional histology.

Liver Tissue Processing

Pre-study biopsy: Approximately three weeks before study start, a cone shaped wedge of liver tissue (~100 mg) was excised from the distal portion of the left lateral lobe, weighed and immediately placed in 4% PFA.

Terminal liver tissue: Following 8 weeks of treatment, the whole liver was collected, weighed and liver biopsy from the left lateral lobe is excised and immediately placed in 4% PFA (~150-200 mg). Pieces of median lobe will be snap frozen in cryotubes (RNAseq)(~100 mg) and in FastPrep tubes for TG (~100 mg) and for TC (~50 mg).

Fixation, embedment and sections for histology: Following an over-night fixation in 4% PFA, liver biopsies were infiltrated over-night in paraffin in an automated Miles Scientific Tissue-TEK VIP Tissue Processor and subsequently embedded in paraffin blocks. Biopsies from five different animals were embedded in one block. The blocks were trimmed and two 3 μm sections per block were cut on a Microm HM340E Microtome (Thermo Scientific). One section from two different blocks was placed on one object slide giving a total of 10 biopsies per slide as outlined above.

Fibrosis Stage

Figure 4:
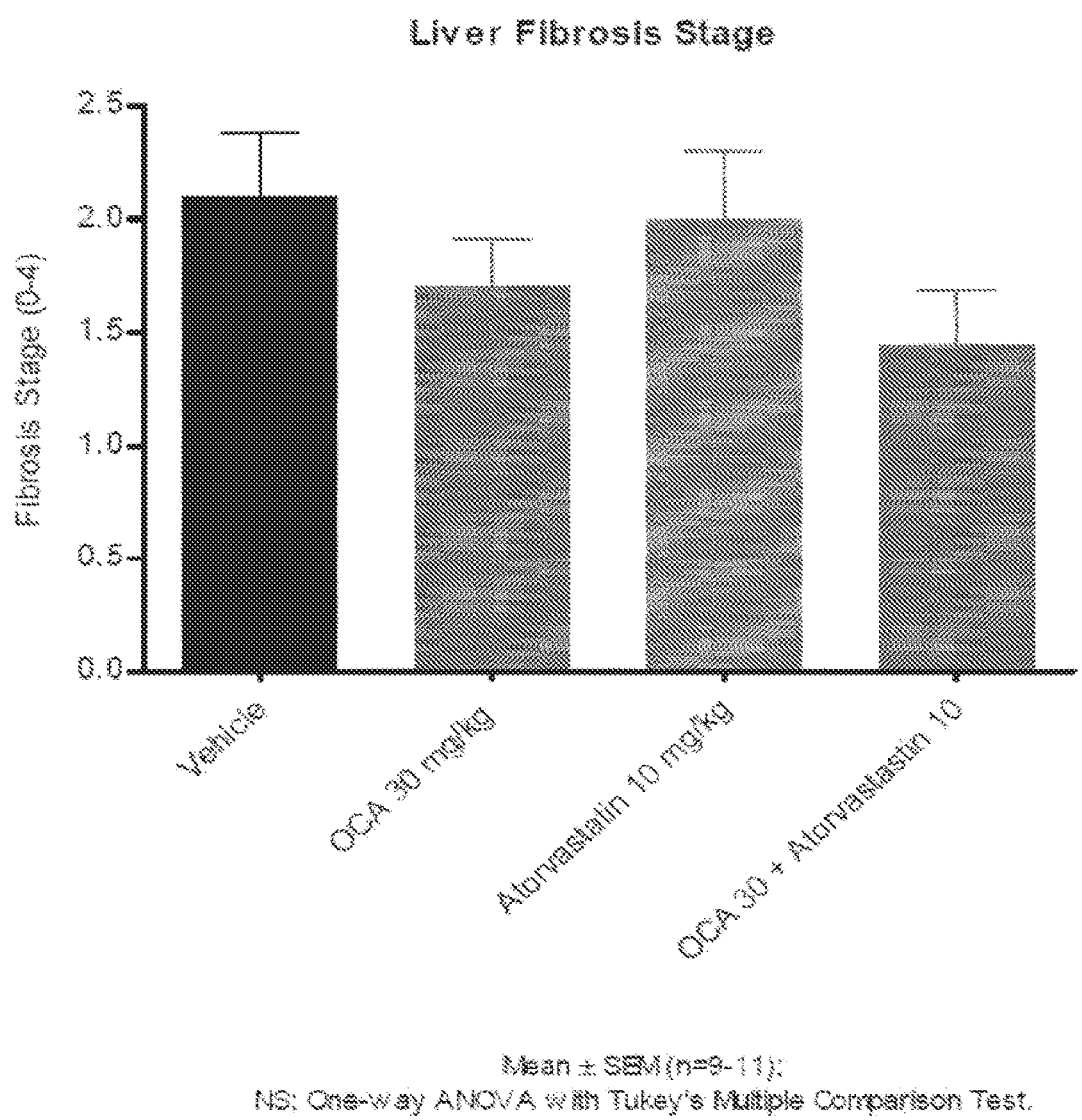
FIG. 4 is a bar graph showing the effects of OCA and atorvastatin alone and in combination on the fibrosis stage in leptin-ob/ob mice.

Liver pre-biopsy and post-biopsy tissue from the left lateral lobe was collected for assessment of fibrosis stage by use of clinical criteria outlined by Kleiner and colleagues (Design and validation of a histological scoring system for nonalcoholic fatty liver disease, Kleiner et al, Hepatology 41; 2005) and reproduced in Table 5 below. FIG. 4 describes the effect OCA and atorvastatin alone and in combination on fibrosis scoring. The combination of OCA and atorvastatin shows a trend in lowering the fibrosis score although not in a significantly manner from vehicle (p value=0.09).

TABLE 5

| Feature | Degree | Score |
|---|---|---|
| Fibrosis | None | 0 |
| | Perisinusoidal or periportal | 1 |
| | Mild, zone 3, perisinusoidal | 1A |
| | Moderate, zone 3, perisinusoidal | 1B |
| | Portal/periportal | 1C |
| | Perisinusoidal & portal/periportal | 2 |
| | Bridging fibrosis | 3 |
| | None | 0 |

Plasma Triglycerides

Triglyceride Levels: 100 µl blood is collected into Lithium-Heparin tubes. Plasma was separated and samples were be stored at −80 degrees Celsius until analysis. Triglyceride levels were measured in single determinations using autoanalyzer Cobas C-111 with commercial kit (Roche Diagnostics, Germany) according to the manufacturer's instructions. As indicated in FIGS. 5A and 5B, the combination of OCA and atorvastatin reduced triglyceride levels in a significantly statistically manner.

Example 4: Sandwich Culture of Hepatocytes

This experiment will be performed to evaluate the effect of OCA in combination with a PPAR agonist or statin to determine their ability to alter collagen synthesis in human hepatocytes.
Reagents and Solutions Suitable cell culture medium includes Waymouth's MB-752/1, Ham's F12, RPMI 1640, Dulbecco's modified Eagle's medium, Williams' medium E, Leibovitz' L15 and modified Chee's medium. Type IV collagenase, type I collagen, Percoll, culture medium and supplements are added to the culture medium (e.g., serum, antibiotics, amino acids, hormones such as DEX, insulin, and growth factors), perfusion buffer, and other solutions were commercially available or made from commercially available materials. Other types of collagen (types II-IV), laminin, fibronectin, and heparin sulfate proteoglycans can be used in the sandwich hepatocyte culture. However, it has been shown that type I and IV collagen were superior to fibronectin and laminin.
Isolation of Hepatocytes A two-step in situ collagenase perfusion method will be utilized to isolate hepatocytes. Briefly, hepatocytes will be isolated from female Lewis rats. Animals will be anesthetized. The liver will be first perfused through the portal vein in situ with a perfusion buffer. The perfusate will be equilibrated before entering the liver. The liver will be subsequently perfused with collagenase in the perfusion buffer. The liver will then dissected and transferred to ice-cold perfusion buffer. The liver capsule will be teased apart, and the resulting cell suspension will be filtered. The cell pellet will be collected by centrifugation and resuspended. Percoll will be added to the suspension, and hepatocytes separated using a Percoll density centrifugation technique. The mixture will be centrifuged, and the cell pellet washed twice with medium. Hepatocytes viability will be determined by Trypan blue exclusion. Alternatively, cryopreserved hepatocytes can be used instead of freshly isolated hepatocytes.
Sandwich Culture of Hepatocytes Isolated hepatocytes will be cultured on collagen-coated tissue culture plates and maintained in culture medium supplemented with serum, penicillin, streptomycin, epidermal growth factor, insulin, glucagon and hydrocortisone. A collagen gelling solution will be prepared by mixing Type I collagen solution and culture medium. Tissue culture plates will be coated with the gelling solution and incubated at 37° C. to promote gel formation. Hepatocytes will be seeded at a proper density and maintained at 37° C. The culture medium will be replaced every 24 hours.

For the sandwich system, an additional collagen gel solution will be distributed over the cells after 1 day of culture. The culture medium will be carefully removed to ensure that the second layer of collagen gel is evenly spread over the entire plate. The culture plates will be incubated at 37° C. to allow gelation and attachment of the second gel layer before the medium was replaced. The culture medium will be changed daily. Medium samples will be stored at −20° C. for further analysis.

Hepatocytes cultured between layers of gelled collagen maintain a three-dimensional cuboidal shape and distribution of cytoskeletal proteins similar to that observed in vivo.
Optimization of Bile Canalicular Network Formation To optimize taurocholate accumulation and biliary excretion, particular culture medium, such as Williams' medium E and Dulbecco's modified Eagle's medium can be used in the sandwich hepatocyte culture.
Test Articles The FXR agonist intended for study is obeticholic acid, also known as "OCA" and 6-ethyl chenodeoxycholic acid (6-ECDCA).

PPAR-alpha agonists intended for study include one or more of clofibrate, gemfibrozil, ciprofibrate, bezafibrate, and fenofibrate).

A dual PPAR-alpha/delta agonist is 2-[2,6 dimethyl-4-[3-[4-(methylthio)phenyl]-3-oxo-1(E)-propenyl]phenoxyl]-2-methylpropanoic acid.

A PPARδ (delta) agonist intended for study is GW501516.

Statins (HMG-CoA reductase inhibitors) intended for study include atorvastatin (Lipitor), rosuvastatin (Crestor) and simvastatin (Zocor).

Example 5: Evaluate Effects of Individual Administration of Test Articles on Lipid Profiles The potential of 5 test articles, an FXR agonist, a PPAR-alpha agonist, a PPAR-delta agonist, a dual PPAR-alpha/delta agonist (or alternatively, PPAR-alpha agonist and PPAR-delta agonist together), and a statin will be assessed to determine the ability to alter cholesterol synthesis and the lipid profile in human hepatocytes. Changes will be evaluated in sandwich-cultured human hepatocytes (SCHH) following 72 hours of exposure to test articles at 3 different concentrations. Dosing solutions will be made fresh daily in culture media and dosing of SCHH will occur daily for 3 days. The experiment will be performed in 24-well format using one (1) lot of Transporter Certified™ Human Hepatocytes (N=1). Each test condition will be performed in three (3) wells to provide triplicate data (expressed as mean±standard deviation). Solvent control treated plates will be used as a control and evaluated for baseline function. At the end of the test period, internal standard will be added to individual wells, followed by addition of the extraction reagent for global lipid profiling. The samples will be shaken for 1 hour at room temperature, and centrifuged. The supernatant will be evaporated to dryness under nitrogen, resuspended and analyzed.

Global lipid profiling will be performed using Ultra-Performance Liquid Chromatography (UPLC) and high-resolution MS. Methyl-t-butyl sample extracts will be analyzed on UPLC-MS (Synapt G2 Ion-Mobility QToF) instrumentation, in ESI+ and ESI− mode, to cover a wide range of lipid polarity and chemical composition. Initially UPLC will be applied to evaluate compound effects on a large array (5000 to 8000) of lipids, including multiple esters of cholesterol. Colorimetric analysis will be performed to measure total cholesterol. Based on abundance most will be glycerophospholipids, however, a large number of classes will be evaluated. Profiles will be evaluated to identify potential effects on individual lipids. Identification of specific lipids can be performed against standards using assay retention time, accurate mass and fragmentation. Depending on the outcome, specific lipids or lipid classes may be identified for evaluation in Examples 6 and 7. A confirmatory study will be repeated in two additional lots of Transporter Certified™ Human Hepatocytes (N=2).

Example 6: Evaluate Effects of Dual Combinations of Test Articles on Lipid Profiles Combinations of FXR agonist, with each of a PPAR-alpha agonist, a PPAR-delta agonist, a PPAR-alpha and delta dual agonist (or, in the alternative, an FXR agonist with a PPAR alpha agonist and a PPAR delta agonist), and/or a statin will be evaluated for their potential to alter cholesterol synthesis and the lipid profile in human hepatocytes. Specific combinations evaluated will be:
- FXR agonist with PPAR-alpha agonist
- FXR agonist with PPAR-delta agonist
- FXR agonist with PPAR-alpha and delta dual agonist and/or FXR agonist with PPAR-alpha agonist and PPAR-delta agonist
- FXR agonist with a statin Changes will be evaluated in sandwich-cultured human hepatocytes (SCHH) following 72 hours of exposure to test articles at 3 different concentrations. Dosing solutions will be made fresh daily in culture media and dosing of SCHH will occur daily for 3 days. The experiment will be performed in 24 well format using one (1) lot of Transporter Certified™ Human Hepatocytes (N=1). Each test condition will be performed in three (3) wells to provide triplicate data (expressed as mean±standard deviation). Samples will be prepared and analyzed for global lipid profiling as detailed in Example 5. Alterations in lipid profiles and cholesterol synthesis will be compared with effects from individual administration in Example 2.

Example 7: Evaluate Effects of Triple Combinations of Test Articles on Lipid Profiles The triple combination of an FXR agonist, PPAR-alpha agonist, PPAR-delta agonist, PPAR-alpha and delta dual agonist (or PPAR-alpha agonist in combination with PPAR-delta agonist), and/or a statin will be evaluated for the potential to alter cholesterol synthesis and the lipid profile in human hepatocytes. Changes will be evaluated in sandwich-cultured human hepatocytes (SCHH) following 72 hours of exposure to test articles at 3 different concentrations. Dosing solutions will be made fresh daily in culture media and dosing of SCHH will occur daily for 3 days. The experiment will be performed in 24-well format using one (1) lot of Transporter Certified™ Human Hepatocytes (N=1). Each test condition will be performed in three (3) wells to provide triplicate data (expressed as mean±standard deviation). Samples will be prepared and analyzed for global lipid profiling as detailed in Example 2. Alterations in lipid profiles and cholesterol synthesis will be compared with effects from combinations administered in Example 2. Specific combinations evaluated will be:
- FXR agonist with a PPAR-alpha agonist, and a statin
- FXR agonist with a PPAR-delta agonist, and a statin
- FXR agonist with a PPAR-alpha and delta dual agonist (or, in the alternative, a PPAR-alpha agonist and a PPAR-delta agonist), and a statin Samples will be prepared and analyzed for global lipid profiling as detailed in Example 4. Alterations in lipid profiles and cholesterol synthesis will be compared with effects from combinations administered in Examples 4 and 5.

Example 8: Animal Studies

Animals

Animals will be housed individually in standard cages at 22° C. in a 12:12-h light-dark cycle. Male C57BL/6 mice (Jackson Laboratories, Bar Harbor, ME) will be allowed ad libitum access to a diet enriched in fat (40% kcal, Primex partially hydrogenated vegetable oil shortening), fructose (22% by wt), and cholesterol (2% by wt) (Research Diets, New Brunswick, NJ, cat. no. D09100301). A low-fat diet (10% kcal; hereafter referred to as LFD) with no fructose or cholesterol will be used as a control diet (Research Diets, cat. no. D09100304). The use of this validated LFD establishes a group of control mice that maintain a "normal" hepatic phenotype for comparison with animals fed the experimental diet.

Treatment Groups
- Control HFD:
- Control LFD:
- HFD+FXR agonist:
- HFD+PPARα (i.e., fenofibrate, gemfibrozil, bezofibrate, or ciprofibrate):
- HFD+PPARδ (i.e., GW501516):
- HFD+PPARα+PPARδ:
- HFD+dual PPARα/δ (i.e., GFT505):
- HFD+statin (i.e., atorvastatin, simvastatin, rosuvastatin)
- HFD+FXR agonist+PPARα:
- HFD+FXR agonist+PPARδ:
- HFD+FXR agonist+PPARα+PPARδ:
- HFD+FXR agonist+dual PPARα/δ:
- HFD+FXR agonist+statin:

Histology and Digital Image Analysis

At termination, right medial and/or left lateral lobes of the liver (>50% of each lobe harvested) will be excised and fixed in 10% neutral-buffered formalin (at least 7 days at room temperature). The liver tissue will be carefully excised to select similarly sized sections representative of both the tissue edge and center. Liver tissue will be paraffin embedded, sectioned (5 μm), and mounted. Hematoxylin and eosin stains will be used for morphological analyses, and Masson's trichrome and Sirius red stains will be used for assessment of hepatic fibrosis. Histopathological analysis will be performed by a pathologist blinded to the study. NAFLD and NASH will be scored by use of criteria outlined by Kleiner and colleagues. For quantitative assessment of fibrosis, whole Sirius red-stained sections will be scanned by use of the ScanScope CS whole slide scanning system (Aperio, Vista, CA) at ×20 magnification. Images will be extracted and Sirius red-stained collagen profiles from entire tissues will be measured by the color cube-based method with Image-Pro Analyzer software (MediaCybernetics v.6.2, Bethesda, MD). Total collagen staining (reported as % of total area) will be assessed from three to four representative sections from each animal (except for the comprehensive liver fibrosis assessment experiment where additional sections will be evaluated). All histological analyses will be performed blinded.

Liver Biopsy

Mice will be anesthetized with isoflurane (2-3%) in 100% oxygen. A small abdominal incision, ~0.5 cm left of midline will be made and the left lateral lobe of the liver will be exposed. A wedge of liver tissue (~50 mg) will be excised from the distal portion of the lobe, immediately placed in a vial, and snap frozen in liquid nitrogen. A wedge of absorbable gelatin sponge (GelFoam, Pfizer, NY) will be inserted into the cut edges of the liver. Once hemostasis is achieved (typically within 1 min) and the gelatin sponge well-adhered to the biopsy site, the liver will be returned to the abdominal cavity, the abdominal wall sutured, and the skin stapled. Mice will receive a single injection of buprenorphine (0.05 mg/kg, subcutaneous) at the time of the surgery to control postoperative pain. Sham operated mice will undergo an identical procedure except no incision made in the liver.

Plasma and Serum Analysis

Plasma glucose, triglycerides, total cholesterol, alanine aminotransferase (ALT), and aspartate aminotransferase (AST) levels will be measured by using an Olympus AU400e Bioanalyzer (Olympus America Diagnostics, Center Valley, PA). Plasma samples will be diluted 1:10 with PBS for measurement of ALT and AST. Total plasma adiponectin and fasting serum insulin will be measured according to the manufacturer's instructions with commercially available electrochemiluminescence kits (Meso Scale Discovery, Gaithersburg, MD).

Quantification of Total Hepatic Lipid and Collagen Content

Total hepatic lipid will be extracted from the liver using a protocol adapted from Folch et al. Frozen liver tissue (~0.3 g) will be homogenized in 10 ml of 2:1 chloroform-methanol solution. The homogenate will be filtered using fat-free filter paper and funneled into a preweighed 15-ml glass vial. An additional 5 ml of 2:1 chloroform-methanol will be added followed by 2.5 ml of 0.9% NaCl. The lipids will be separated by centrifugation at 1,800 g, 10° C. for 5 min, the aqueous layer will be discarded, and the tube will be flushed with nitrogen until the lipid pellet will be dry. The tube containing the lipid pellet will be reweighed, and total lipid extracted per gram of total liver will be calculated. Total collagen content in the liver will be measured by colorimetric determination of hydroxyproline residues by acid hydrolysis of collagen (Quickzyme, Leiden, Netherlands).

Determination of Extractable Collagen-1α1 Protein by Protein Blot

Tissue cores (50-100 mg) will be collected from the left lateral lobe of the liver, snap frozen in liquid nitrogen, and stored at –80° C. until processed. The tissue will be homogenized in lysis buffer containing protease inhibitors. Protein concentration of the cleared supernatant will be measured with a BCA protein assay kit (Pierce, Rockford, IL). Liver tissue lysates (~50 µg) will be separated on reducing 4-12% Nupage gels (Life Technologies, Carlsbad, CA) and transferred to nitrocellulose membranes. Membranes will be cut between the 50- and 60-kDa markers and blocked with 5% Blotto. The upper half will be probed with anti-collagen-1%1 (1:1,000; cat. no. NBP1-30054; Novus Biologicals, Littleton, CO), which detects the COOH-terminal telopeptide portion of the collagen-1%1 protein. For normalization, the lower half will be probed with anti-glyceraldehyde 3-phosphate dehydrogenase (GAPDH, 1:7,500; cat. no. 3683; Cell Signaling Technologies, Danvers, MA). Following incubation with horseradish peroxidase anti-rabbit antibody, protein expression will be detected with enhanced chemiluminescence (Thermo Scientific, Rockford, IL), and densitometry will be performed with a FluorChem System (Cell Biosciences, Santa Clara, CA). Densitometry analysis of collagen-1α1 will include both the 140-kDa mature protein as well as a slightly larger band, corresponding to a glycosylated form or a partially processed collagen-1α1 protein.

Hepatic Gene Expression Changes

Tissue samples from the left lateral lobe of the liver will be harvested with a 6-mm tissue coring tool or by the biopsy method, snap frozen in liquid nitrogen, and stored at –80° C. until processed. Total RNA from liver samples (~50-150 mg) will be extracted by use of TRI Reagent (Life Technologies) and then further purified with a Qiagen RNeasy Plus Mini kit (Qiagen, Valencia, CA). RNA integrity will be determined by using the Agilent 6000 nano kit on a Bioanalyzer 2100 (Agilent Technologies, Santa Clara, CA). cDNA will be prepared by using the High Capacity cDNA Reverse Transcription Kit (Life Technologies). Changes in gene expression will be confirmed by TaqMan gene expression assays-on-demand and Universal Master Mix (Life Technologies) on an ABI Prism 7900HT instrument (Applied Biosystems, Foster City, CA). Change in gene expression will be calculated by the comparative threshold cycle (CT) method with peptidylprolyl isomerase A (Ppia) and Gapdh for normalization. For gene arrays, cDNA samples will be run on Mouse Fibrosis RT2 Profiler PCR Arrays (PAMM-120C, RT2 SYBR Green/ROX qPCR Master Mix; SABiosciences) by using the ABI Prism 7900HT Fast Real-Time PCR System (Applied Biosystems). Changes in gene expression on the array will be calculated by the comparative CT method using DataAssist v3.0 software (Applied Biosystems/Life Technologies). Among the five housekeeping genes included in the Mouse Fibrosis RT2 Profiler PCR Array, hypoxanthine phosphoribosyltransferase 1 (Hprt) and Gapdh have the most stable expression according to the stability scores calculated by DataAssist v3.0 software. The mean of the chosen endogenous control genes will be used as the normalization factor to calculate the relative expression of each gene. To confirm the results obtained by using the fibrosis array, TaqMan Gene expression assays will be conducted for a selection of genes determined by the array to be upregulated, downregulated, or unchanged.

Example 9: Clinical Trial

A multicenter, double-blind, placebo-controlled, parallel group, randomized clinical trial was conducted in patients with non-cirrhotic, non-alcoholic steatohepatitis to assess treatment with obeticholic acid given orally (25 mg daily) or placebo for 72 weeks. Patients were randomly assigned 1:1 using a computer-generated, centrally administered procedure, stratified by clinical center and diabetes status. The primary outcome measure was improvement in centrally scored liver histology defined as a decrease in non-alcoholic fatty liver disease activity score by at least 2 points without worsening of fibrosis from baseline to the end of treatment. Change in alanine aminotransferase at 24 weeks was measured: relative change in alanine aminotransferase –24%, 95% CI –45 to –3.

Study Design and Participants

Patients were enrolled in the study according to the following inclusion criteria: 18 years or older at the time of screening, histological evidence of definite or borderline non-alcoholic steatohepatitis based upon a liver biopsy obtained 90 days or less before randomization, and a histological non-alcoholic fatty liver disease (NAFLD) activity score of 4 or more with a score of 1 or more in each component of the score (steatosis scored 0-3, ballooning 0-2, and lobular inflammation 0-3). Grading and staging of biopsies for the purposes of enrollment were carried out at the site of enrollment. Exclusion criteria include the presence of cirrhosis, other causes of liver disease, substantial alcohol consumption (>20 g/day for women or >30 g/day for men), or other confounding conditions (see below).

Randomization and Masking

Patients meeting eligibility criteria were randomly assigned (1:1) to oral obeticholic acid, 25 mg once-daily, or placebo. Obeticholic acid and placebo were provided as identical tablets in identical containers labelled with code numbers. Patients, investigators, clinical site staff, and pathologists will be masked to treatment assignment.

Procedures

After randomization, patients returned for study visits at weeks 2, 4, and 12, and then every 12 weeks until completion of treatment at week 72, and then 24 weeks later. Blood samples were obtained at these visits for routine biochemical tests and assessment of fasting concentrations of lipids, glucose, and insulin. Body weight, height, and waist and hip circumferences were measured at the initial assessment and designated interim times. All patients received standard recommendations on healthy eating habits, weight reduction, exercise, and the management of hypertension, hypercholesterolemia, and diabetes when indicated.

Baseline and end-of-treatment liver biopsies were centrally assessed as a group for consensus scoring of each component of the NAFLD activity score, determined fibrosis stage, and assigned a diagnosis of non-alcoholic steatohepatitis, borderline non-alcoholic steatohepatitis, or not non-alcoholic steatohepatitis.

Inclusion and Exclusion Criteria

Patients who meet any of the following exclusion criteria were considered ineligible for enrollment: 1) Current or history of significant alcohol consumption for a period of more than 3 consecutive months within 1 year prior to screening (significant alcohol consumption was defined as more than 20 g/day in females and more than 30 g/day in males, on average); 2) Inability to reliably quantify alcohol consumption based upon site investigator's judgment; 3) Use of drugs historically associated with NAFLD for more than 2 weeks in the year prior to randomization; 4) Prior or planned bariatric surgery or procedure; 5) Uncontrolled diabetes defined as HbA1c of 80.3 mmol/mol or higher within 60 days prior to enrollment; 6) Presence of cirrhosis on liver biopsy, 7) Platelet count <100×109/L; 8) Clinical evidence of hepatic decompensation as defined by the presence of any of the following abnormalities: serum albumin less than 32 g/L, INR greater than 1.3, direct bilirubin greater than 22.2 μmol/L, or a history of esophageal varices, ascites, or hepatic encephalopathy; 9) Evidence of other forms of chronic liver disease: hepatitis B as defined by presence of hepatitis B surface antigen (HBsAg), hepatitis C as defined by presence of hepatitis C virus (HCV) RNA or positive hepatitis C antibody (anti-HCV), evidence of ongoing autoimmune liver disease as defined by compatible liver histology, primary biliary cirrhosis as defined by the presence of at least 2 criteria (biochemical evidence of cholestasis based mainly on alkaline phosphatase elevation, presence of anti-mitochondrial antibody [AMA], and histologic evidence of nonsuppurative destructive cholangitis and destruction of interlobular bile ducts), primary sclerosing cholangitis, Wilson's disease as defined by ceruloplasmin below the limits of normal and compatible liver histology, alpha-1-antitrypsin (A1AT) deficiency as defined by diagnostic features in liver histology (confirmed by alpha-1 antitrypsin level less than normal, exclusion at the discretion of the site investigator), history of hemochromatosis or iron overload as defined by presence of 3+ or 4+ stainable iron on liver biopsy, drug-induced liver disease as defined on the basis of typical exposure and history, known bile duct obstruction, suspected or proven liver cancer, or any other type of liver disease other than NASH; 10) Serum alanine aminotransferase (ALT) greater than 300 U/L; 11) Serum creatinine of 176.8 μmol/L or greater; 12) Inability to safely obtain a liver biopsy; 13) History of biliary diversion; 14) Known positivity for Human Immunodeficiency Virus (HIV) infection; 15) Active, serious medical disease with likely life expectancy less than 5 years; 16) Active substance abuse including inhaled or injection drugs in the year prior to screening; 17) Pregnancy, planned pregnancy, potential for pregnancy and unwillingness to use effective birth control during the trial, or breast feeding; 18) Participation in an IND trial in the 30 days before randomization; 19) Any other condition which, in the opinion of the site investigator, would impede compliance or hinder completion of the study; or 20) Failure to give informed consent.

Statistical Analysis

The primary outcome and binary secondary outcomes were analyzed using the Mantel-Haenszel test; continuous secondary outcomes were analyzed using ANCOVA models relating change in the continuous outcome from baseline to 72 weeks to treatment group and to the baseline value of the outcome. Statistical analyses were performed with SAS (SAS Institute 2011, Base SAS 9.3 Procedures Guide) and Stata (StataCorp 2013, Stata Statistical Software: release 13).

Outcomes

The primary outcome measure was improvement in centrally scored liver histology defined as a decrease in NAFLD activity score by at least 2 points without worsening of fibrosis from baseline to the end of treatment. Worsening of fibrosis was defined as any numerical increase in the stage. Secondary histological outcomes include resolution of non-alcoholic steatohepatitis, change in NAFLD activity score, and changes in the individual scores for hepatocellular ballooning, steatosis, lobular and portal inflammation, and fibrosis. Improvement in fibrosis was defined as any numerical decrease in the stage. Fibrosis stages 1a, 1b, and 1c were considered stage 1 for the purposes of analysis. Other secondary outcomes include changes from baseline to 72 weeks in serum aminotransferase and γ-glutamyl transpeptidase concentrations, fasting homoeostasis model of assessment of insulin resistance (HOMA-IR), anthropometric measures (weight, bodymass index, waist-to-hip ratio, waist circumference), and health-related quality-of-life scores.

Example 10: Data Analysis

A subanalysis of the data obtained in Example 9 was performed to assess the effect of statins on low density lipoprotein cholesterol (LDL-C) levels. The aims of these secondary analyses were to determine the effect of OCA versus placebo in the subgroup of patients with more severe NASH and to assess the effects of concomitant statin use on serum LDL cholesterol. Subject data were assessed in three groups as follows:

Group A (n=64, no statin) included subjects in the obeticholic acid (OCA) treatment arm who were not on a statin at baseline (Day 0) and who do not initiate a statin throughout the course of the study up to and including Week 72.

Group B (n=47, baseline statin) included subjects in the OCA treatment arm who were on a statin at baseline and who continued on the statin during the study up to and including Week 72.

Group C (n=23, new statin) included subjects in the OCA treatment arm who were not on a statin at baseline but initiated statin treatment at a time after baseline up to and including Week 72.

The following calculations were performed for OCA treated subjects in Groups A, B, and C.

Mean and median characteristics listed below will be evaluated at baseline and at Week 72.
Laboratory values: LDL-C, high density lipoprotein cholesterol (HDL-C), alanine and aspartate aminotransferase, gamma glutamyl transferase
Age
Gender: percentage male, percentage female
Percentage diabetic
Histology: steatosis, ballooning, inflammation, fibrosis
Mean and median percentage change at Week 72 from baseline of the above characteristics will be evaluated.

Results

Figure 8:
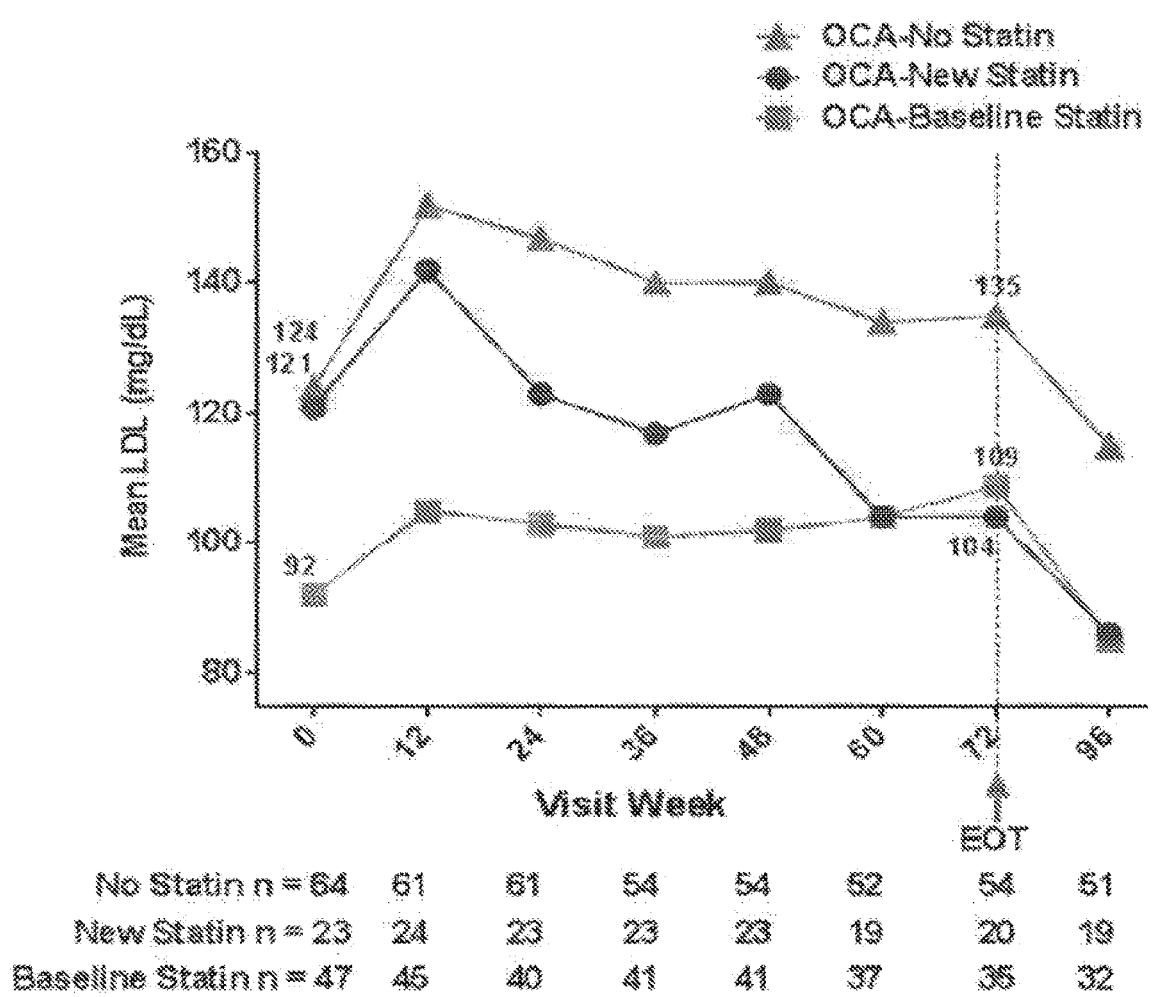
FIG. 8 is a graph showing the effect of OCA and a combination of a statin(s) on LDL cholesterol in humans.

LDL cholesterol increased during OCA treatment in patients on statins at baseline, but levels did not exceed those of Placebo-treated patients not on statins. Statin initiation during OCA treatment reversed LDL to below pre-OCA baseline levels. As shown in FIG. 8, the OCA-related LDL increase appeared to be reversed by initiating statin therapy during OCA treatment.

The invention claimed is:

1. A pharmaceutical composition comprising a combination of a compound of formula (1):

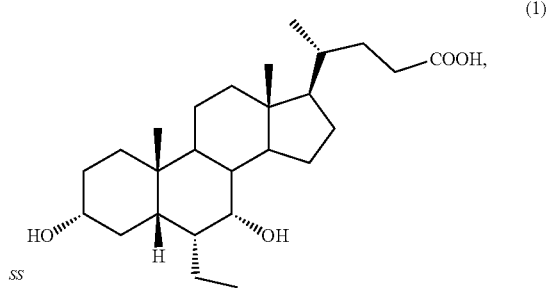 [SMILES: "SS" ; CC[C@H]1[C@@H](O)C2C3CC[C@H]([C@H](C)CCC(=O)O)[C@@]3(C)CCC2[C@@]2(C)CC[C@@H](O)C[C@@H]12]

or a pharmaceutically acceptable salt or amino acid conjugate thereof, and bezafibrate; and optionally one or more pharmaceutically acceptable carriers, wherein bezafibrate is in an amount of 80-400 mg; and
wherein the compound of formula (1) or pharmaceutically acceptable salt or amino acid conjugate thereof is in an amount of about 5 mg or about 10 mg.

2. A pharmaceutical composition comprising a combination of therapeutic agents consisting of a compound of formula (1):

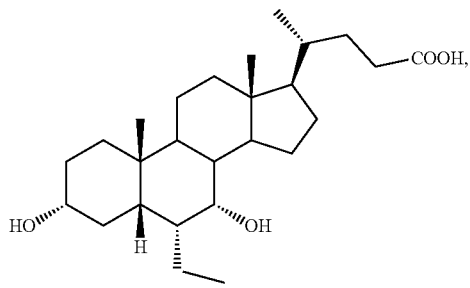

or a pharmaceutically acceptable salt or amino acid conjugate thereof, and bezafibrate; wherein the pharmaceutical composition further optionally comprises one or more pharmaceutically acceptable carriers, wherein bezafibrate is in an amount of 80-400 mg; and
wherein the compound of formula (1) or pharmaceutically acceptable salt or amino acid conjugate thereof is in an amount of about 5 mg or about 10 mg.

3. The pharmaceutical composition of claim 2, wherein bezafibrate is in an amount of 100-300 mg.

4. The pharmaceutical composition of claim 2, wherein bezafibrate is in an amount of 100 mg.

5. The pharmaceutical composition of claim 2, wherein bezafibrate is in an amount of 200 mg.

6. The pharmaceutical composition of claim 2, wherein bezafibrate is in an amount of 400 mg.

7. The pharmaceutical composition of claim 2, wherein the composition is a single unit dosage form.

8. The pharmaceutical composition of claim 7, wherein the single unit dosage form is a tablet or capsule.

9. The pharmaceutical composition of claim 1, wherein bezafibrate is in an amount of 100-300 mg.

10. The pharmaceutical composition of claim 1, wherein bezafibrate is in an amount of 100 mg.

11. The pharmaceutical composition of claim 1, wherein bezafibrate is in an amount of 200 mg.

12. The pharmaceutical composition of claim 1, wherein bezafibrate is in an amount of 400 mg.

13. The pharmaceutical composition of claim 1, wherein the composition is a single unit dosage form.

14. The pharmaceutical composition of claim 13, wherein the single unit dosage form is a tablet or capsule.

15. The pharmaceutical composition of claim 2, wherein the compound of formula (1) or pharmaceutically acceptable salt or amino acid conjugate thereof is in an amount of about 5 mg and bezafibrate is in an amount of 400 mg.

16. The pharmaceutical composition of claim 15, wherein the composition is a single unit dosage form.

17. The pharmaceutical composition of claim 16, wherein the single unit dosage form is a tablet or capsule.

18. The pharmaceutical composition of claim 17, wherein the single unit dosage form is a tablet.

* * * * *